United States Patent
Park et al.

(10) Patent No.: US 11,322,708 B2
(45) Date of Patent: May 3, 2022

(54) ORGANIC LIGHT-EMITTING DIODE HAVING LONG LIFESPAN PROPERTY

(71) Applicant: SFC CO., LTD., Cheongju-si (KR)

(72) Inventors: Young-Hwan Park, Cheongju-si (KR); Seo-Yeon Yoon, Seongnam-si (KR); Chang-Hee Lee, Cheongju-si (KR); So Young Shim, Daejeon (KR)

(73) Assignee: SFC CO., LTD., Cheongju-si (KR)

( * ) Notice: Subject to any disclaimer, the term of this patent is extended or adjusted under 35 U.S.C. 154(b) by 13 days.

(21) Appl. No.: 17/125,024

(22) Filed: Dec. 17, 2020

(65) Prior Publication Data

US 2021/0119167 A1 Apr. 22, 2021

Related U.S. Application Data

(62) Division of application No. 15/772,537, filed as application No. PCT/KR2016/012803 on Nov. 8, 2016, now Pat. No. 10,950,814.

(30) Foreign Application Priority Data

Nov. 18, 2015 (KR) .................. 10-2015-0161980
Sep. 20, 2016 (KR) .................. 10-2016-0120245

(51) Int. Cl.
*H01L 51/50* (2006.01)
*H01L 51/52* (2006.01)
*H01L 51/00* (2006.01)

(52) U.S. Cl.
CPC ........ *H01L 51/5028* (2013.01); *H01L 51/006* (2013.01); *H01L 51/0059* (2013.01); *H01L 51/0061* (2013.01); *H01L 51/0073* (2013.01); *H01L 51/5072* (2013.01); *H01L 51/5092* (2013.01); *H01L 51/5206* (2013.01); *H01L 51/5221* (2013.01); *H01L 51/5004* (2013.01); *H01L 51/5056* (2013.01); *H01L 2227/323* (2013.01)

(58) Field of Classification Search
CPC .............. H01L 51/5028; H01L 51/006; H01L 51/0073; H01L 51/5004; H01L 51/5056
See application file for complete search history.

(56) References Cited

FOREIGN PATENT DOCUMENTS

DE        102012007795 B3 *  2/2013  ........... C07C 211/54
JP        2015201279 A   *  11/2015

OTHER PUBLICATIONS

Fukase et al., JP2015201279 (A), English Machine Translation (Year: 2015).*
Zollner et al., DE102012007795B3, English Machine Translation (Year: 2013).*

* cited by examiner

*Primary Examiner* — Tae-Sik Kang
(74) *Attorney, Agent, or Firm* — STIR Law Group, LLC

(57) ABSTRACT

The present disclosure relates to an organic light-emitting diode: comprising a first electrode; a second electrode facing the first electrode; and a hole transport layer and a light-emitting layer disposed in that order between the first and the second electrode, wherein the light-emitting layer includes a host and a hole assistant material represented by the following Chemical Formula A, the hole assistant material having a highest occupied molecular orbital (HOMO) energy level lower in absolute value than that of the host.

13 Claims, 3 Drawing Sheets

ORGANIC LIGHT-EMITTING DIODE HAVING LONG LIFESPAN PROPERTY

CROSS-REFERENCE TO RELATED APPLICATIONS

This application is a division of application Ser. No. 15/772,537 filed on May 1, 2018, which in turn claims the benefit International Application No. PCT/KR2016/012803 filed on Nov. 8, 2016, which in turn claims the benefit of Korean Patent Application No. 10-2015-0161980 filed on Nov. 18, 2015, and 10-2016-0120245 filed on Sep. 20, 2016, the disclosures of which are incorporated by reference into the present application.

TECHNICAL FIELD

The present disclosure relates to an organic light-emitting diode having a long lifespan characteristic and, more particularly, to an organic light-emitting diode comprising a hole assistant material in a light-emitting layer thereof to supplement the hole mobility of a host material within the light-emitting layer.

BACKGROUND ART

Organic light-emitting diodes (OLEDs), based on self-luminescence, enjoy the advantage of having a wide viewing angle and being able to be made thinner and lighter than liquid crystal displays. In addition, an OLED display exhibits a very fast response time. Accordingly, OLEDs find applications in the full color display field or the illumination field.

In general, the term "organic light-emitting phenomenon" refers to a phenomenon in which electrical energy is converted to light energy by means of an organic material. An OLED using the organic light phenomenon has a structure usually comprising an anode, a cathode, and an organic material layer interposed therebetween. In this regard, the organic material layer may be, for the most part, of a multilayer structure consisting of different materials, for example, a hole injection layer, a hole transport layer, a light-emitting layer, an electron transport layer, and an electron injection layer, in order to improve the efficiency and stability of the organic light-emitting diode.

In the organic light-emitting diode having such a structure, when a voltage is applied between the two electrodes, a hole injected from the anode migrates to the organic layer while an electron is released from the cathode and moves toward the organic layer. In the luminescence zone, the hole and the electron recombine to produce an exciton. When the exciton returns to the ground state from the excited state, the molecule of the organic layer emits light. Such an organic light-emitting diode is known to have characteristics such as self-luminescence, high luminescence, high efficiency, a low driving voltage, a wide viewing angle, high contrast, and high-speed response.

Materials used as the organic layers in OLEDs may be divided into luminescent materials and charge transport materials, for example, a hole injection material, a hole transport material, an electron injection material, and an electron transport material. As for the luminescent materials, there are two main families of OLED: those based on small molecules and those employing polymers. The light-emitting mechanism forms the basis for classification of the luminescent materials as fluorescent or phosphorescent materials, which use excitons in singlet and triplet states, respectively.

Meanwhile, when a single material is employed as the luminescent material, intermolecular actions cause the wavelength of maximum luminescence to shift toward a longer wavelength, decreasing color purity or attenuating light with the consequent reduction in efficiency of the diode. In this regard, a host-dopant system may be used as a luminescent material so as to increase the color purity and the light emission efficiency through energy transfer.

This is based on the principle whereby, when a dopant is smaller in energy band gap than a host accounting for the light-emitting layer, the addition of a small amount of the dopant to the host generates excitons from the light-emitting layer so that the excitons are transported to the dopant, emitting light at high efficiency. Here, light of desired wavelengths can be obtained depending on the kinds of dopant because the wavelength of the host moves to the wavelength range of the dopant.

When a luminescent zone of a light-emitting layer in which carriers recombine is formed near an interface between a hole injection layer and the light-emitting layer, the organic light-emitting diodes including hosts and dopants according to conventional techniques can improve in luminous efficiency, but decreases in lifespan due to the local formation of the luminescent zone.

In order to solve this problem, Korean Patent No. 10-2013-0074129 (Jul. 4, 2013) discloses an organic light-emitting diode in which an electron trap material including a cyclic aromatic derivative such as pyrene, phenanthrene, anthracene, etc. is introduced to a light-emitting layer to allow electrons to easily stay within the light-emitting layer, whereby the organic light-emitting diode can be improve in luminous efficiency and lifespan thereof can be prolonged.

However, the patent is directed to an aromatic polycyclic derivative for use as the electron trap material, which seems to focus simply on the function of blocking the movement of electrons, but does not include the function of aiding the movement of holes.

There is therefore still the continued need to develop an organic light-emitting diode having a novel structure in which a luminescent zone is not formed locally at an interface between a hole injection layer and a light-emitting layer, but widely across the light-emitting layer and which can supplement the hole mobility of a host material.

DETAILED DESCRIPTION OF THE INVENTION

Technical Problem

Accordingly, a purpose to be achieved by the present disclosure is to provide an organic light-emitting diode which additionally includes within a light-emitting layer thereof a material serving as a hole assistant which acts in combination with a host in the light-emitting layer to supplement the hole mobility of the host.

Technical Solution

In order to accomplish the purpose, the present disclosure provides an organic light-emitting diode: comprising a first electrode; a second electrode facing the first electrode; and a hole transport layer and a light-emitting layer disposed in that order between the first and the second electrode, wherein the light-emitting layer includes a hole assistant material represented by the following Chemical Formula A and an anthracene-based host represented by the following Chemical Formula H, the hole assistant material having a highest occupied molecular orbital (HOMO) energy level lower in absolute value than that of the host:

[Chemical Formula A]

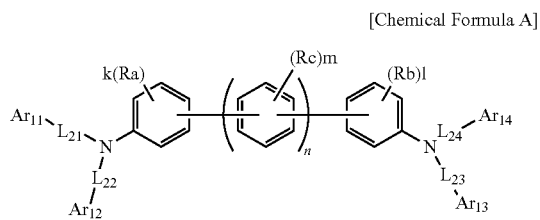

wherein, substituents $Ar_{11}$ to $Ar_{14}$ may be the same or different and are each independently a substituted or unsubstituted aryl of 6 to 50 carbon atoms, or a substituted or unsubstituted heteroaryl of 2 to 50 carbon atoms, linkers $L_{21}$ to $L_{24}$ may be the same or different and are each independently a single bond or a substituted or unsubstituted arylene of 6 to 50 carbon atoms, Ra, Rb, and Rc may be the same or different and are each independently one selected from among a hydrogen atom, a deuterium atom, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted aryl of 6 to 50 carbon atoms, a substituted or unsubstituted heteroaryl of 2 to 50 carbon atoms bearing O, N, or S as a heteroatom, a cyano, a nitro, a halogen, and a substituted or unsubstituted silyl of 1 to 30 carbon atoms, k, l, and m may be the same or different and are each an integer of 1 to 4, with the proviso that when k, l, and m are each an integer of 2 or greater, the corresponding plural Ra's Rb's, or Rc's may be the same or different, n is an integer of 0 to 2, with the proviso that when n is 2, the corresponding two ring moieties, each having (Rc)m, may be the same or different; and

[Chemical Formula H]

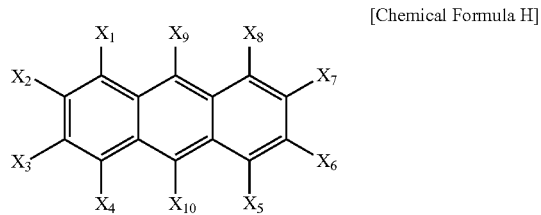

wherein, $X_1$ to $X_{10}$ may be the same or different and are each independently one selected from the group consisting of a hydrogen atom, a deuterium atom, a substituted or unsubstituted alkyl of 1 to 30 carbon atoms, a substituted or unsubstituted alkenyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted aryl of 6 to 50 carbon atoms, a substituted or unsubstituted heteroaryl of 2 to 50 carbon atoms bearing O, N, or S as a heteroatom, a substituted or unsubstituted silicon, a substituted or unsubstituted boron, a substituted or unsubstituted silane, a carbonyl, a phosphoryl, an amino, a nitrile, a hydroxyl, a nitro, a halogen, an amide, and an ester, with the proviso that adjacent radicals may form an aliphatic, aromatic, heteroaliphatic, or heteroaromatic fused ring, wherein the term "substituted" in the expression "substituted or unsubstituted" used for Chemical Formulas A and H means having at least one substituent selected from the group consisting of a deuterium atom, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a heteroarylamino of 1 to 24 carbon atoms, an alkylsilyl of 1 to 24 carbon atoms, an arylsilyl of 6 to 24 carbon atoms, and an aryloxy of 6 to 24 carbon atoms.

Advantageous Effects

Designed to facilitate the hole mobility of a host within a light-emitting layer and to disperse a luminescent zone widely across the light-emitting layer, but not locally at an interface between hole injection layer and the light-emitting layer, the organic light-emitting diose has an prolonged lifespan and an additional advantage in that the driving voltage is somewhat lowered thanks to a decreased hole injection barrier.

MODE FOR CARRYING OUT THE INVENTION

Figure 1:
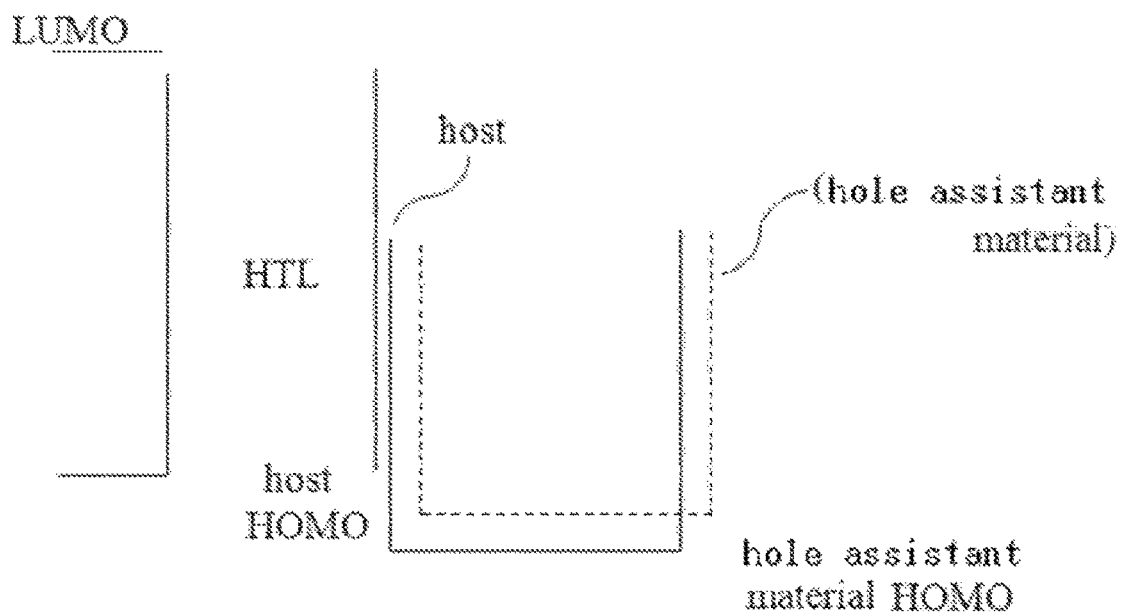
FIG. 1 is a schematic view showing HOMO energy levels of a host and a hole assistant material in an organic light-emitting diode according to an embodiment of the present disclosure.

Hereinafter, some embodiments which can be easily performed by those skilled in the art will be described with reference to the accompanying drawings. In the drawings of the disclosure, sizes and dimensions of structures are illustrated by enlarging or reducing as compared with the actual sizes and dimensions to clarify the disclosure, the known configurations are not illustrated to exhibit characteristic configurations, and the disclosure is not limited to the drawings.

When describing the principle of the embodiments of the present disclosure in detail, details of well-known functions and features may be omitted to avoid unnecessarily obscuring the presented embodiments.

In addition, the size and thickness of each configuration illustrated in the drawings are arbitrarily illustrated for the sake of convenience of explanation, and thus the present disclosure may not be necessarily limited to the illustration. Further, in the drawings, the thickness of layers and regions are illustrated in enlargement for clarity. For the sake of explanation, thicknesses of certain layers and regions are exaggerated.

Throughout the specification, when a portion may "include" a certain constituent element, unless explicitly described to the contrary, it may not be construed to exclude another constituent element but may be construed to further include other constituent elements. Further, throughout the specification, the word "on" means positioning on or below the object portion, but does not essentially mean positioning on the lower side of the object portion based on a gravity direction.

The present disclosure provides an organic light-emitting diode: comprising a first electrode; a second electrode facing the first electrode; and a hole transport layer and a light-emitting layer disposed in that order between the first and the second electrode, wherein the light-emitting layer includes a hole assistant material represented by the following Chemical Formula A and an anthracene-based host represented by the following Chemical Formula H, the hole assistant material having a highest occupied molecular orbital (HOMO) energy level lower in absolute value than that of the host:

[Chemical Formula A]

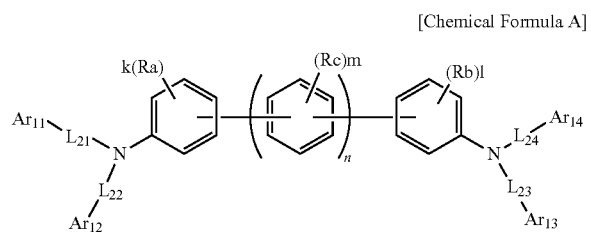

wherein, substituents $Ar_{11}$ to $Ar_{14}$ may be the same or different and are each independently a substituted or unsubstituted aryl of 6 to 50 carbon atoms, or a substituted or unsubstituted heteroaryl of 2 to 50 carbon atoms, linkers $L_{21}$ to $L_{24}$ may be the same or different and are each independently a single bond or a substituted or unsubstituted arylene of 6 to 50 carbon atoms, Ra, Rb, and Rc may be the same or different and are each independently one selected from among a hydrogen atom, a deuterium atom, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted aryl of 6 to 50 carbon atoms, a substituted or unsubstituted heteroaryl of 2 to 50 carbon atoms bearing O, N, or S as a heteroatom, a cyano, a nitro, a halogen, and a substituted or unsubstituted silyl of 1 to 30 carbon atoms, k, l, and m may be the same or different and are each an integer of 1 to 4, with the proviso that when k, l, and m are each an integer of 2 or greater, the corresponding plural Ra's Rb's, or Rc's may be the same or different, n is an integer of 0 to 2, with the proviso that when n is 2, the corresponding two ring moieties, each having (Rc)m, may be the same or different; and

[Chemical Formula H]

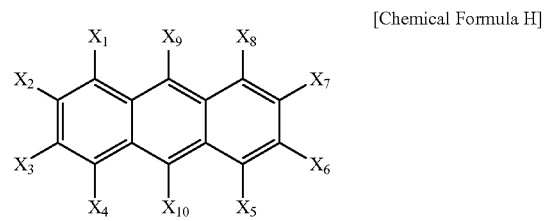

wherein, $X_1$ to $X_{10}$ may be the same or different and are each independently one selected from the group consisting of a hydrogen atom, a deuterium atom, a substituted or unsubstituted alkyl of 1 to 30 carbon atoms, a substituted or unsubstituted alkenyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted aryl of 6 to 50 carbon atoms, a substituted or unsubstituted heteroaryl of 2 to 50 carbon atoms bearing O, N, or S as a heteroatom, a substituted or unsubstituted silicon, a substituted or unsubstituted boron, a substituted or unsubstituted silane, a carbonyl, a phosphoryl, an amino, a nitrile, a hydroxyl, a nitro, a halogen, an amide, and an ester, with the proviso that adjacent radicals may form an aliphatic, aromatic, heteroaliphatic, or heteroaromatic fused ring, wherein the term "substituted" in the expression "substituted or unsubstituted" used for Chemical Formulas A and H means having at least one substituent selected from the group consisting of a deuterium atom, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a heteroarylamino of 1 to 24 carbon atoms, an alkylsilyl of 1 to 24 carbon atoms, an arylsilyl of 6 to 24 carbon atoms, and an aryloxy of 6 to 24 carbon atoms.

The expression indicating the number of carbon atoms, such as "a substituted or unsubstituted alkyl of 1 to 24 carbon atoms", "a substituted or unsubstituted aryl of 6 to 24 carbon atoms", etc. means the total number of carbon atoms of, for example, the alkyl or aryl radical or moiety alone, exclusive of the number of carbon atoms of substituents attached thereto. For instance, a phenyl group with a butyl at the para position falls within the scope of an aryl of 6 carbon atoms, even though it is substituted with a butyl radical of 4 carbon atoms.

As used herein, the term "aryl" as a substituent used in the compounds of the present disclosure means an organic radical derived from an aromatic hydrocarbon by removing a hydrogen atom and may further include a fused ring that is formed by adjacent substituents on the organic radical.

Concrete examples of the aryl include phenyl, o-biphenyl, m-biphenyl, p-biphenyl, o-terphenyl, m-terphenyl, p-terphenyl, naphthyl, anthryl, phenanthryl, pyrenyl, indenyl, fluorenyl, tetrahydronaphthyl, perylenyl, chrysenyl, naphthacenyl, and fluoranthenyl, at least one hydrogen atom of which may be substituted by a deuterium atom, a halogen atom, a hydroxy, a nitro, a cyano, a silyl, an amino (—$NH_2$, —NH(R), or —N(R')(R") wherein R' and R" are each independently an alkyl of 1 to 10 carbon atoms, in this case, called "alkylamino"), an amidino, a hydrazine, a hydrazone, a carboxyl, a sulfonic acid, a phosphoric acid, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 6 to 24 carbon atoms, a heteroaryl of 2 to 24 carbon atoms, or a heteroarylalkyl of 2 to 24 carbon atoms.

The substituent heteroaryl used in the compound of the present disclosure refers to a cyclic aromatic system of 2 to 24 carbon atoms bearing one to three heteroatoms selected from among N, O, P, and S. In the aromatic system, two or more rings may be fused. One or more hydrogen atoms on the heteroaryl may be substituted with the same substituents as in the aryl.

Examples of the substituent alkyl useful in the present disclosure include methyl, ethyl, propyl, isobutyl, sec-butyl, tert-butyl, pentyl, iso-amyl, and hexyl. At least one hydrogen atom of the alkyl may be substituted by the same substituent as in the aryl.

Examples of the substituent alkoxy useful in the present disclosure include methoxy, ethoxy, propoxy, isobutyloxy, sec-butyloxy, pentyloxy, iso-amyloxy, and hexyloxy. At least one hydrogen atom of the alkoxy may be substituted with the same substituent as in the aryl.

Representative among examples of the substituent silyl useful in the present disclosure are trimethylsilyl, triethylsilyl, triphenylsilyl, trimethoxysilyl, dimethoxyphenylsilyl, diphenylmethylsilyl, diphenylvinylsilyl, methylcyclobutylsilyl, and dimethylfurylsilyl. One or more hydrogen atoms of the silyl may be substituted by the same substituent as in the aryl.

The present disclosure is characterized in that a hole assistant material represented by Chemical Formula A and an anthracene-based host represented by Chemical Formula H are included within a light-emitting layer which may further include a dopant.

Here, the present disclosure is further characterized in that the hole assistant material, as shown in Chemical Formula A, has two or four substituted or unsubstituted phenylene moieties connected in series with an aryl or heteroaryl radical-containing diamine attached to each of the opposite terminal phenylene moieties and an anthracene-based compound is used as a host, with the proviso that the hole assistant material has a highest occupied molecular orbital (HOMO) energy level lower in absolute value than that of the host.

FIG. 1 is a schematic view showing HOMO energy levels of a host and a hole assistant material in an organic light-emitting diode according to an embodiment of the present disclosure.

With circumstantial reference to FIG. 1, the HOMO energy level of the hole assistant material according to the present disclosure is lower in absolute value than that of the host. When the HOMO energy level of a hole assistant compound is lower in absolute value than that of a host, a luminescent zone can be widely disposed across the light-emitting layer, but not locally at an interface between the hole injection layer and the light-emitting layer, whereby the diode can be improved in lifespan and the driving voltage is somewhat decreased thanks to the effect of lowering a hole injection barrier.

When used as a hole assistant material, the compound represented by Chemical Formula A according to the present disclosure may have a hole mobility greater than that of a host material.

According to an embodiment of the present disclosure, substituents $Ar_{11}$ to $Ar_{14}$ may be the same or different and are each independently a substituted or unsubstituted aryl of 6 to 50 carbon atoms, and n is 0 or 1 in Chemical Formula A.

In Chemical Formula A, in greater detail, Ra, Rb, and Rc may be the same or different and are each independently selected among a hydrogen atom, a deuterium atom, a substituted or unsubstituted alkyl of 1 to 10 carbon atoms, and a substituted or unsubstituted aryl of 6 to 20 carbon atoms, and linkers $L_{21}$ to $L_{24}$ may be the same or different and are each independently selected from among a single bond and a substituted or unsubstituted aryl of 6 to 20 carbon atoms.

Concrete examples of the hole assistant material represented by Chemical Formula in accordance with the present disclosure include, but are not limited to, the following [Compound 101] to [Compound 142]:

<Compound 101>

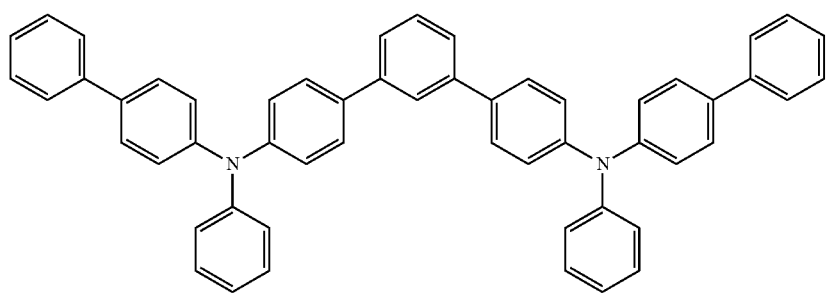

-continued
<Compound 102>
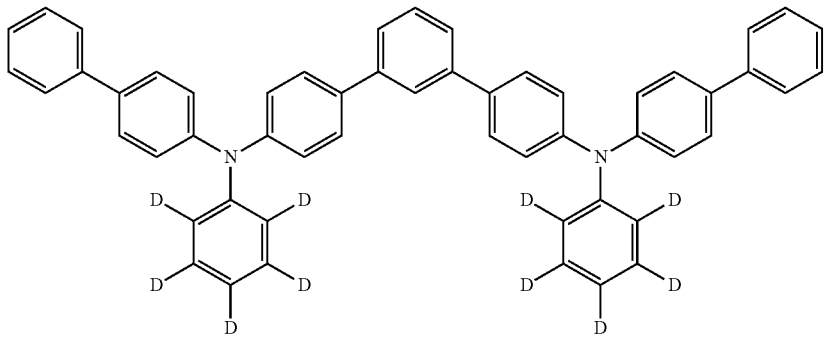
<Compound 103>
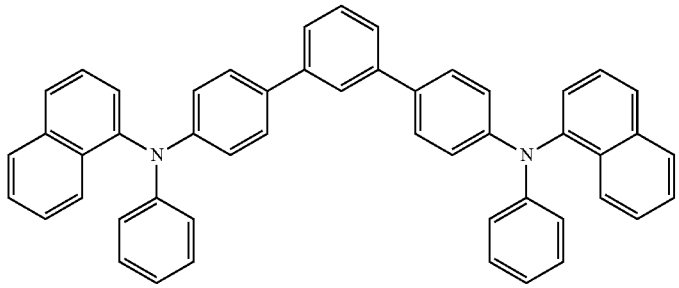
<Compound 104>
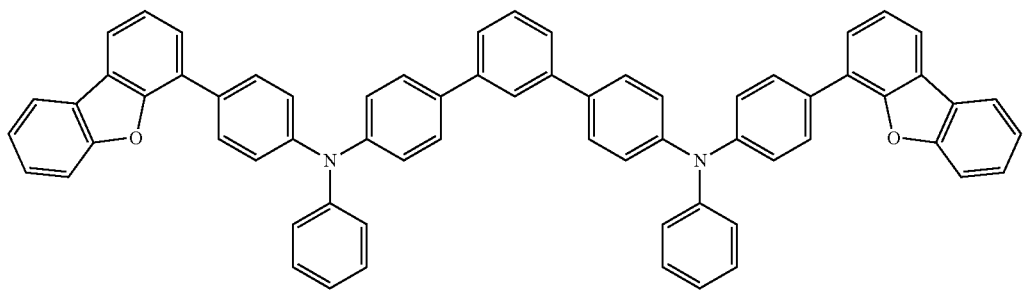
<Compound 105>
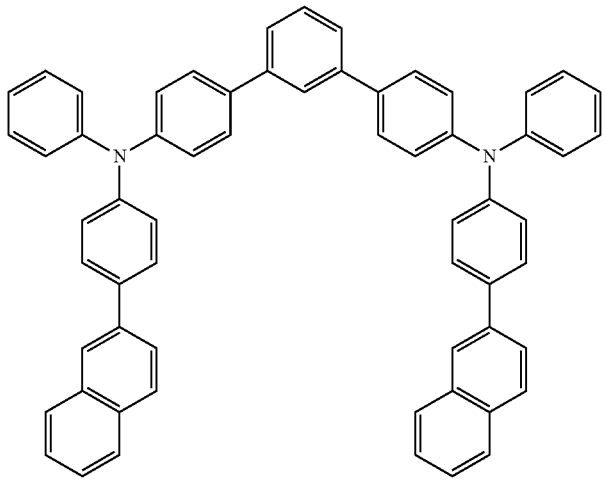

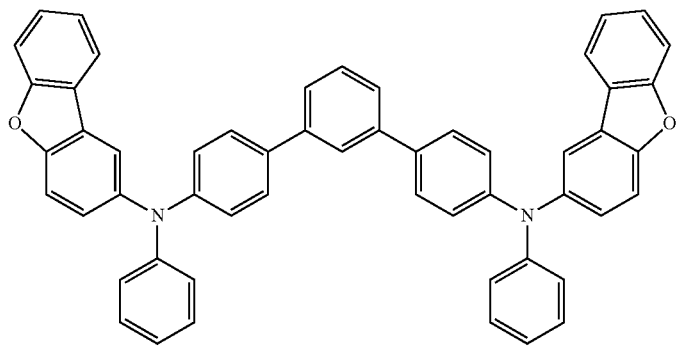
<Compound 106>
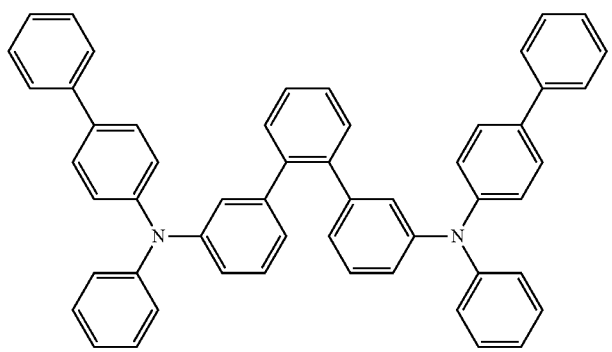
<Compound 107>
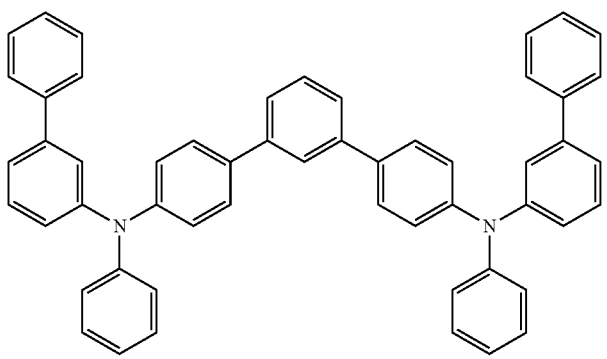
<Compound 108>
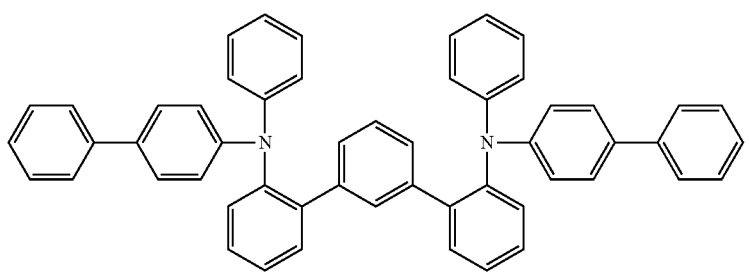
<Compound 109>

-continued
<Compound 110>
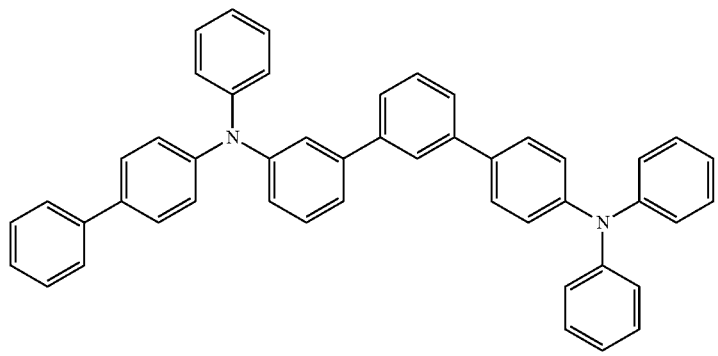
<Compound 111>
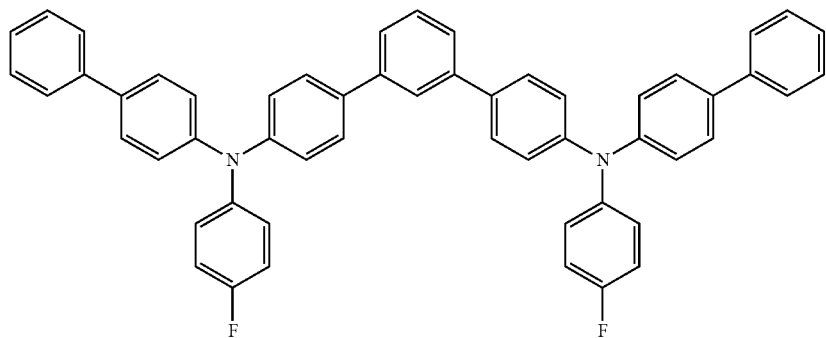
<Compound 112>
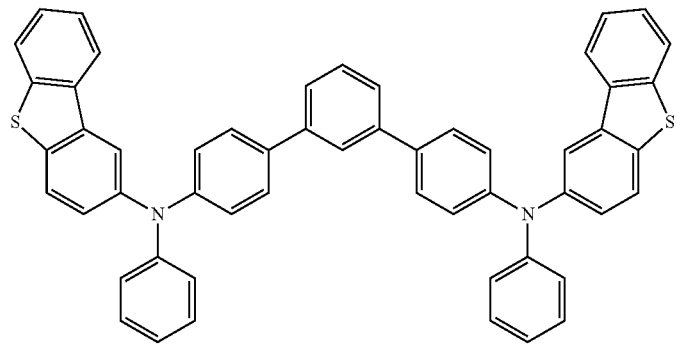
<Compound 113>
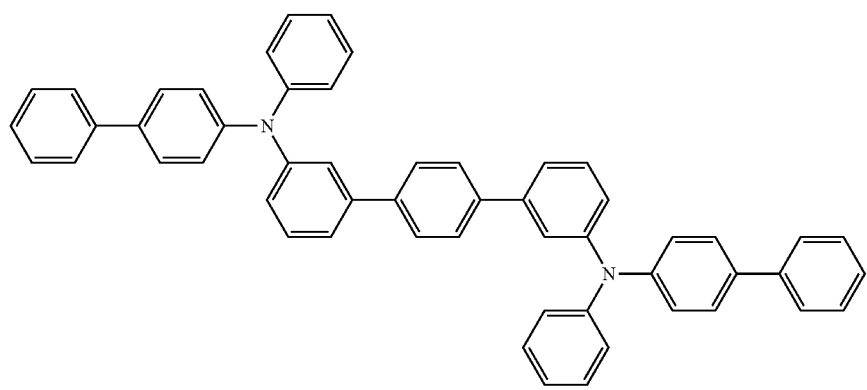

<Compound 114>
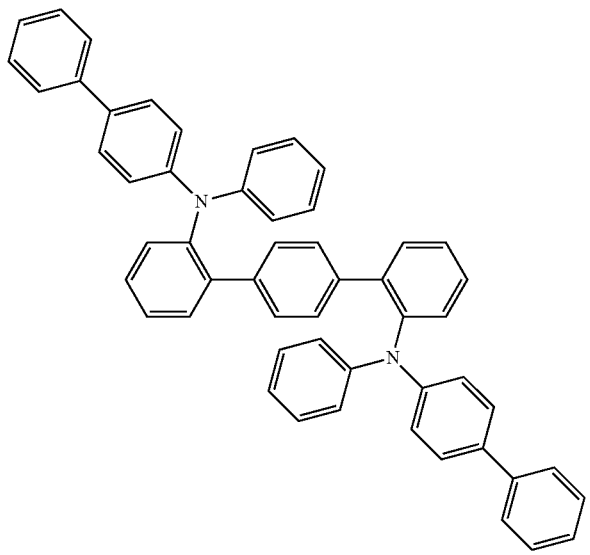
<Compound 115>
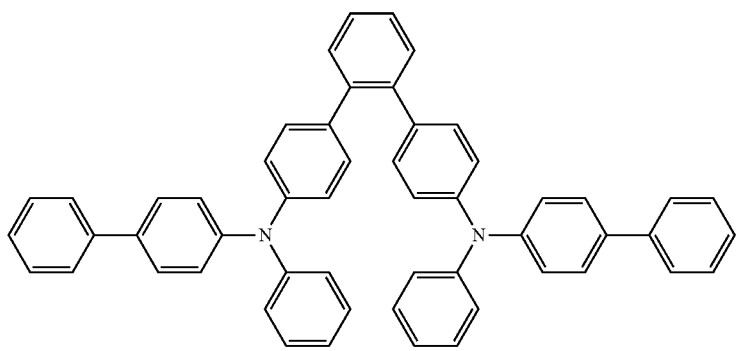
<Compound 116>
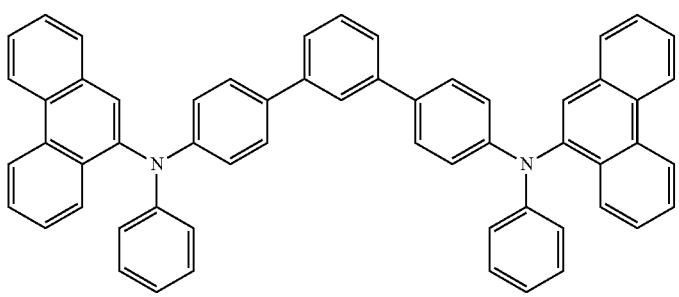
<Compound 117>
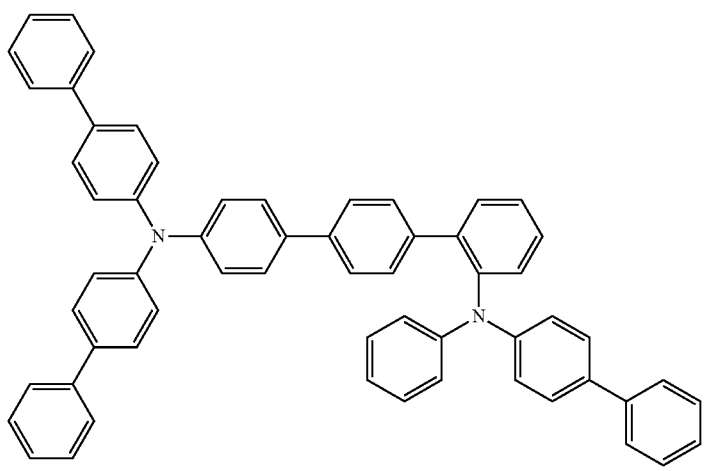

-continued
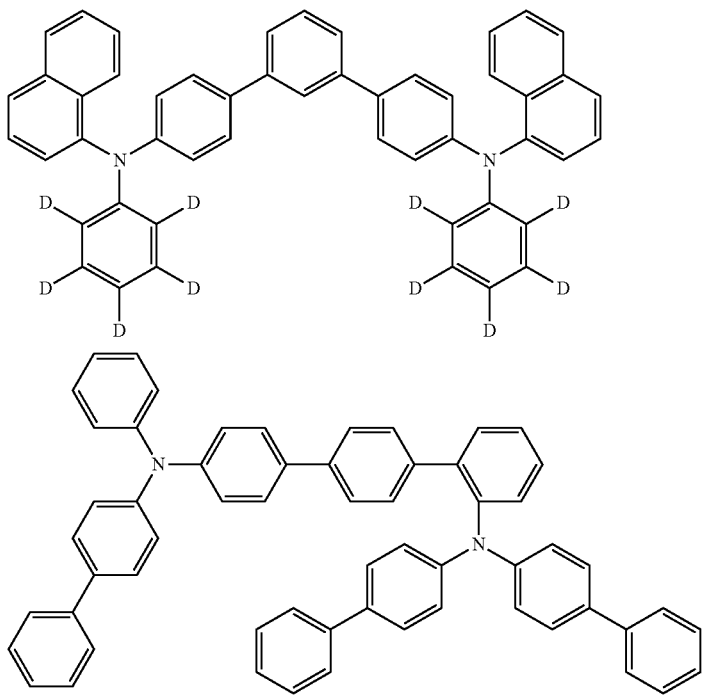
<Compound 118>
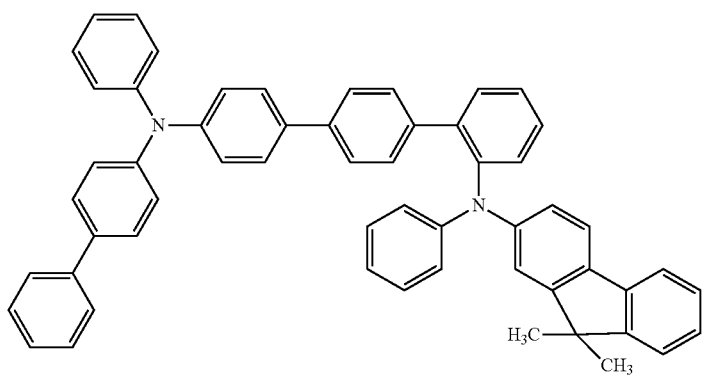
<Compound 120>
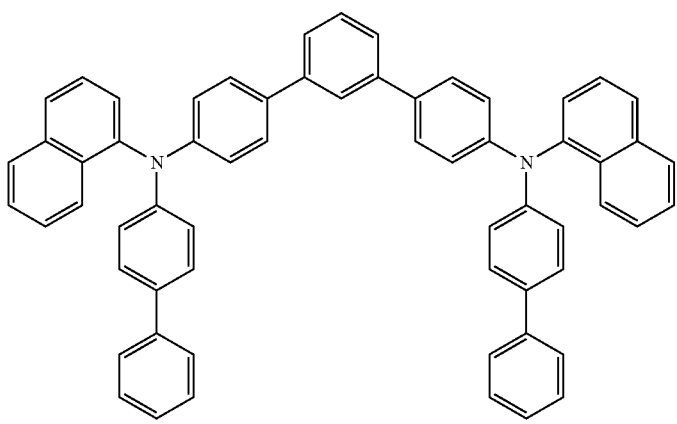
<Compound 121>

-continued
<Compound 122>
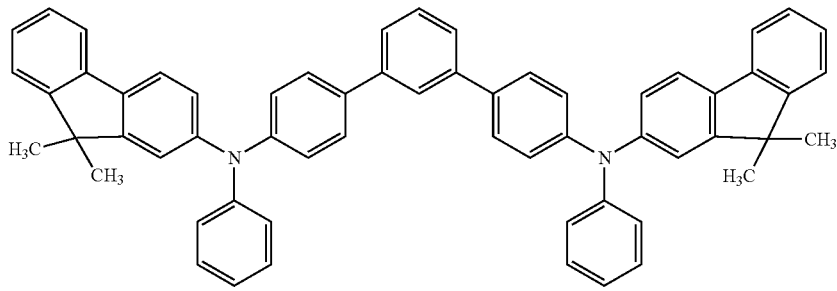
<Compound 123>
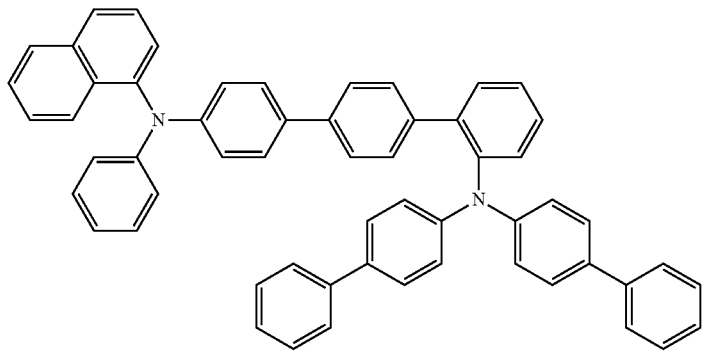
<Compound 124>
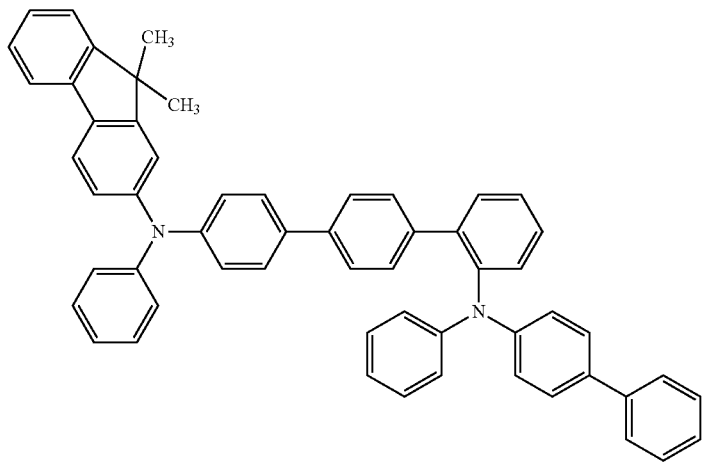
<Compound 125>
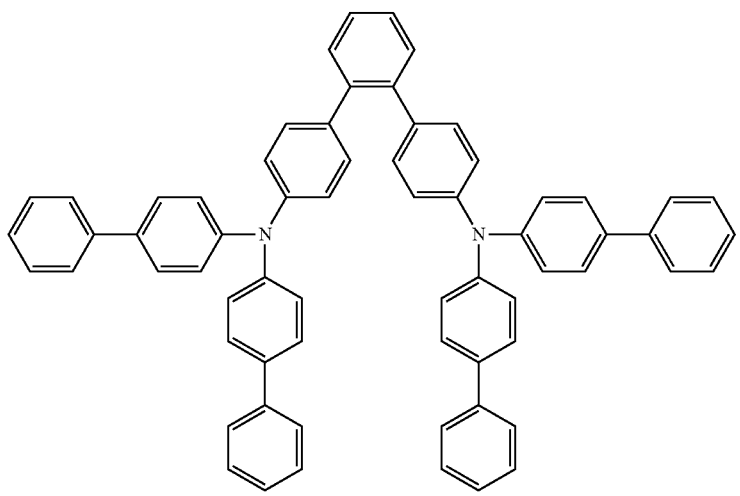

<Compound 126>
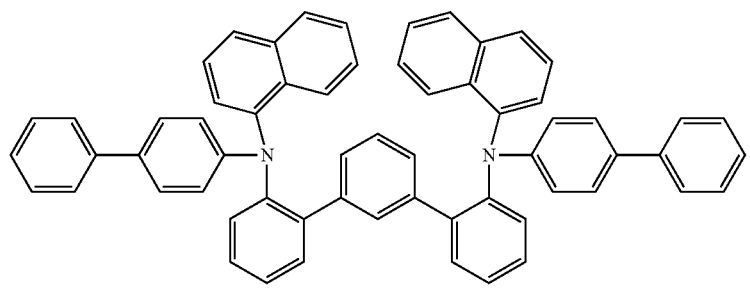
<Compound 127>
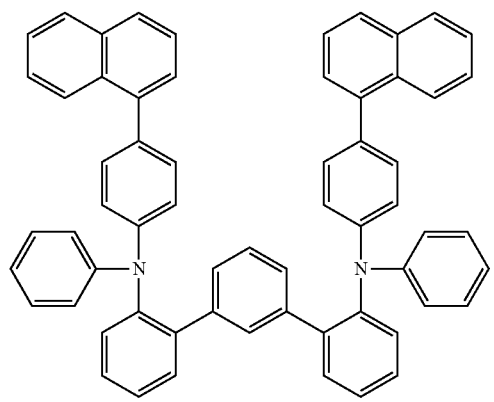
<Compound 128>
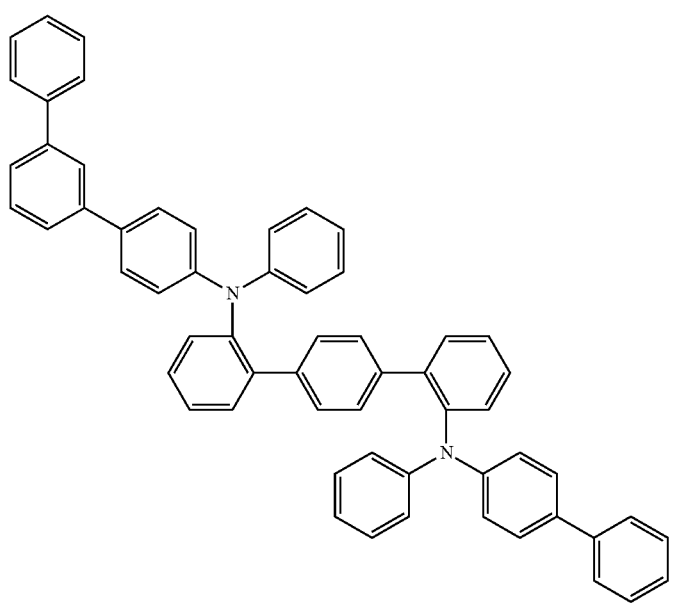

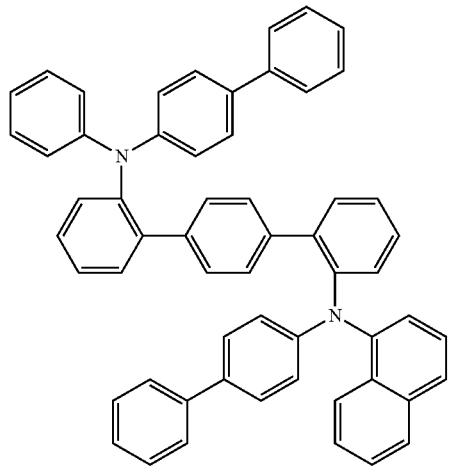
<Compound 129>
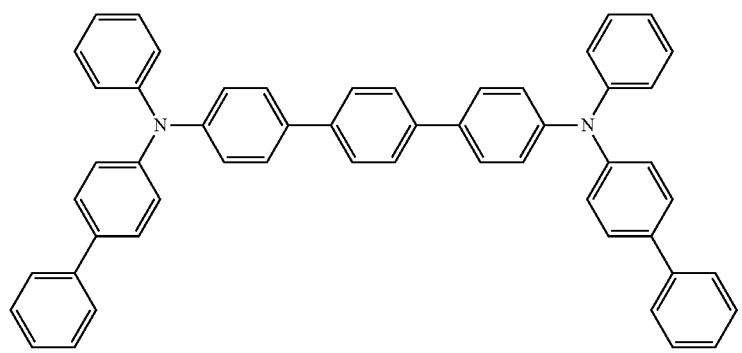
<Compound 130>
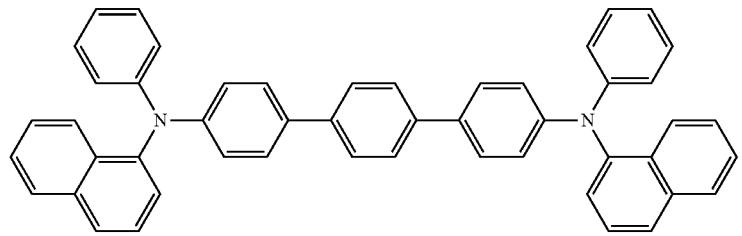
<Compound 131>
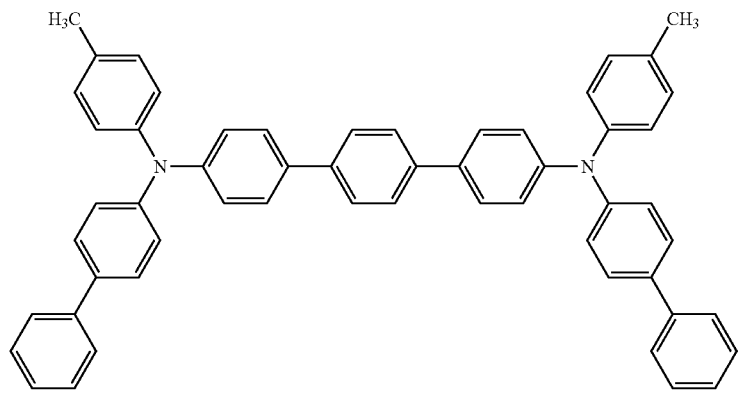
<Compound 132>

-continued
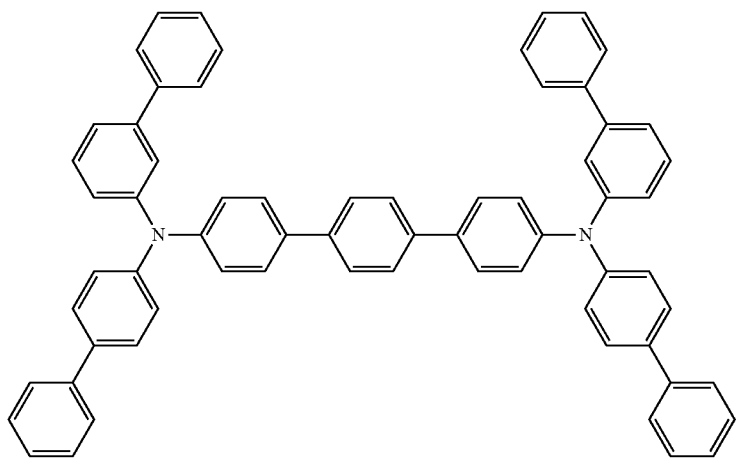
<Compound 133>
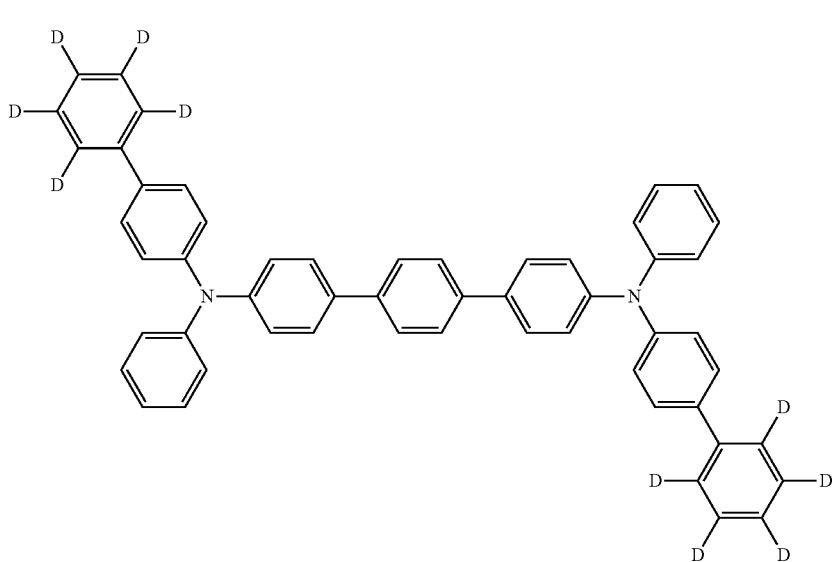
<Compound 134>
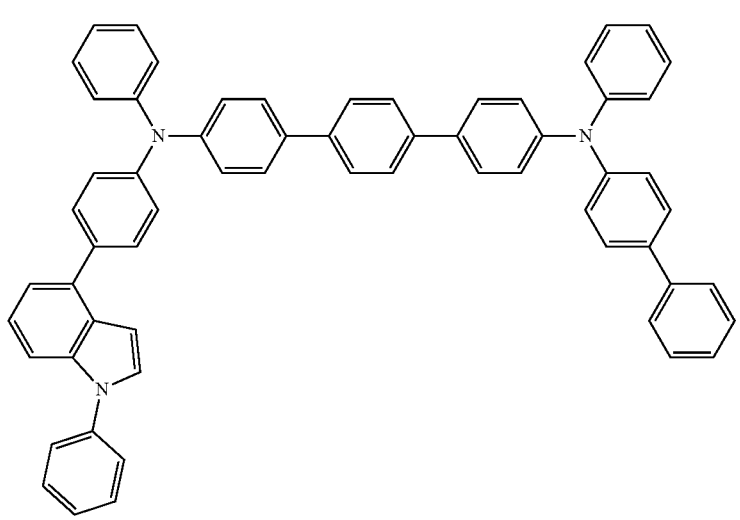
<Compound 135>

<Compound 136>
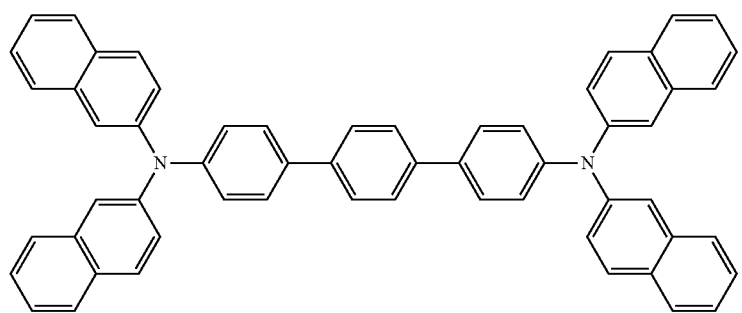
<Compound 137>
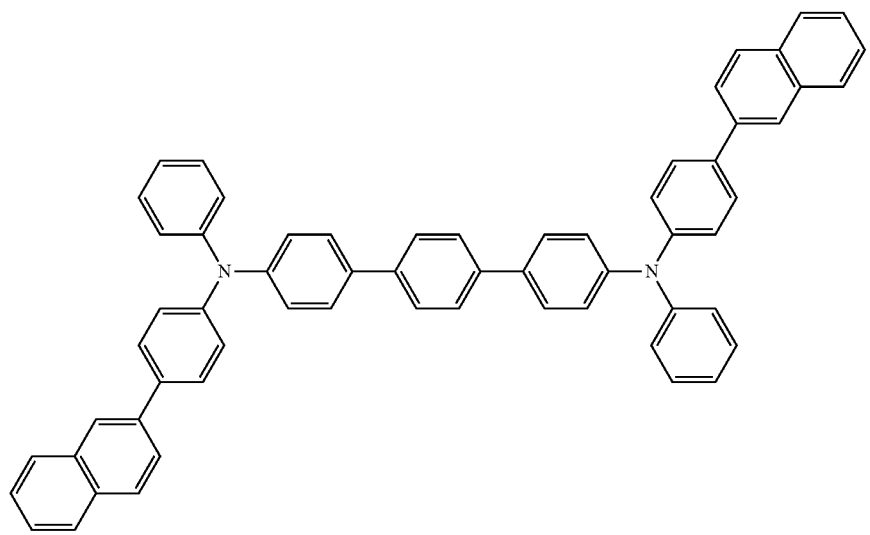
<Compound 138>
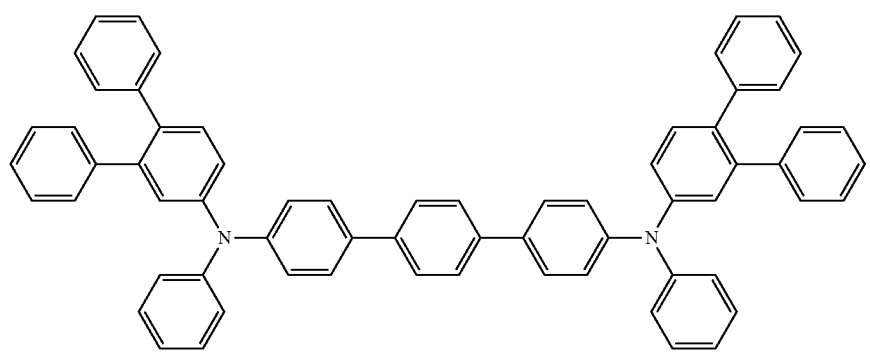

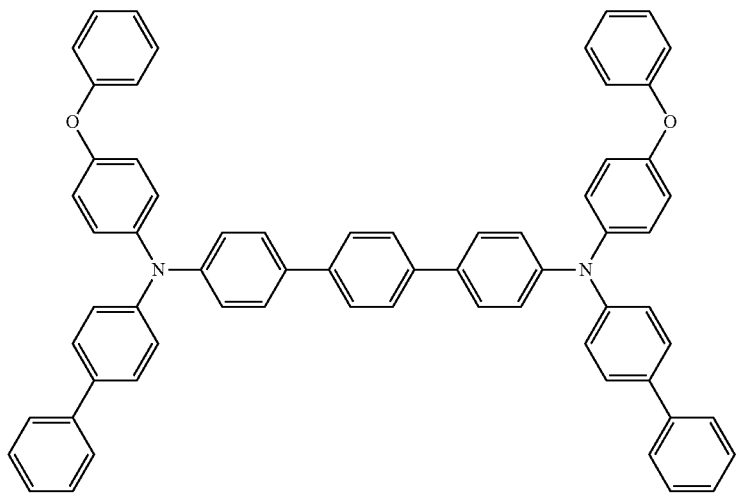
<Compound 139>
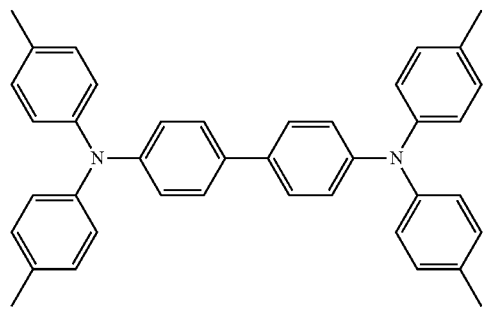
<Compound 140>
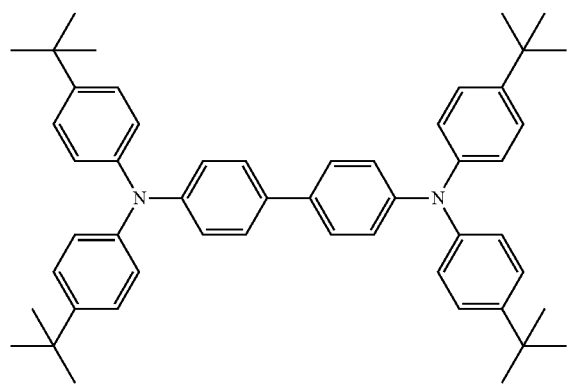
<Compound 141>

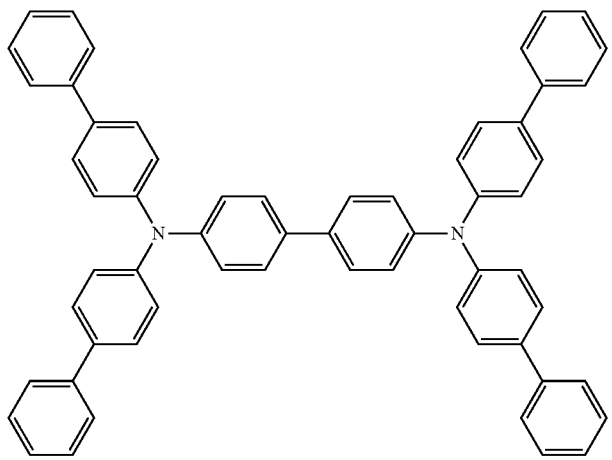

<Compound 142>

When operated, the organic light-emitting diode employing the hole assistant material within the light-emitting layer thereof aids to facilitate the hole mobility of a host in the light-emitting layer such that a luminescent zone is dispersed widely across the light-emitting layer, but not locally at an interface between the hole injection layer and the light-emitting layer, whereby the organic light-emitting diode has a prolonged lifespan and a somewhat decreased driving voltage attributable to a lowered hole injection barrier.

Meanwhile, the host of the light-emitting layer in the organic light-emitting diode of the present disclosure may be an anthracene compound represented by the following Chemical Formula H and may further include various host materials:

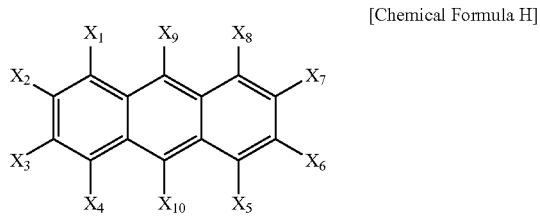

[Chemical Formula H]

wherein, $X_1$ to $X_{10}$ may be the same and are each independently one selected from the group consisting of a hydrogen atom, a deuterium atom, a substituted or unsubstituted alkyl of 1 to 30 carbon atoms, a substituted or unsubstituted alkenyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted aryl of 6 to 50 carbon atoms, a substituted or unsubstituted heteroaryl of 3 to 50 carbon atoms bearing O, N, or S as a heteroatom, a substituted or unsubstituted silicone, a substituted or unsubstituted boron, a substituted or unsubstituted silane, a carbonyl, a phosphoryl, an amino, a nitrile, a hydroxyl, a nitro, a halogen, an amide, and an ester, with the proviso that adjacent radicals may form an aliphatic, aromatic, heteroaliphatic, or heteroaromatic fused ring, wherein the term "substituted" in the expression "substituted or unsubstituted" used for Chemical Formula H means having at least one substituent selected from the group consisting of a deuterium atom, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 6 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a heteroarylamino of 1 to 24 carbon atoms, an alkylsilyl of 1 to 24 carbon atoms, an arylsilyl of 6 to 24 carbon atoms, and an aryloxy of 6 to 24 carbon atoms.

Concrete examples of the host include, but are not limited to, the compounds represented by the following Chemical Formulas 1 to 60:

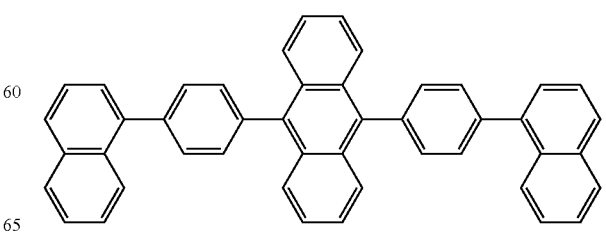

<Chemical Formula 1>

<Chemical Formula 2>
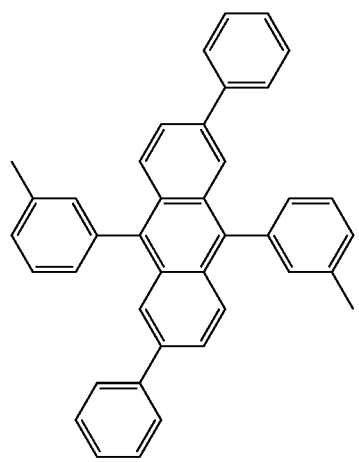
<Chemical Formula 3>
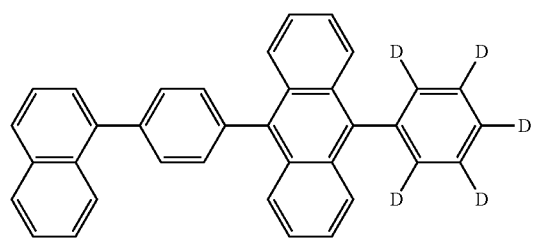
<Chemical Formula 4>
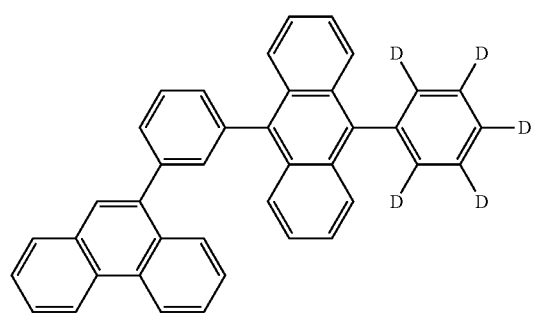
<Chemical Formula 5>
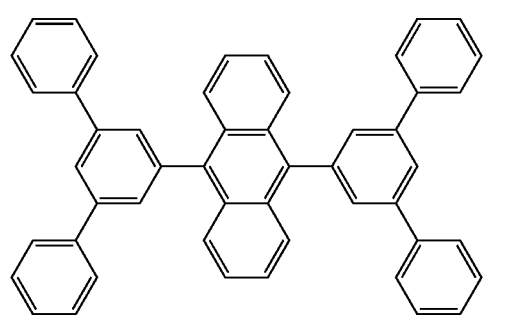
<Chemical Formula 6>
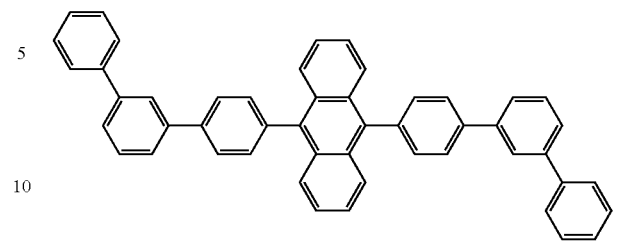
<Chemical Formula 7>
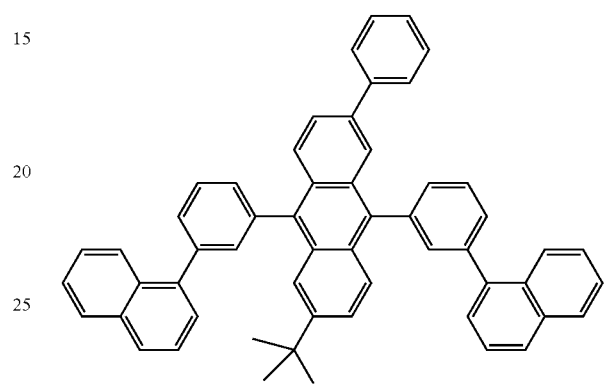
<Chemical Formula 8>
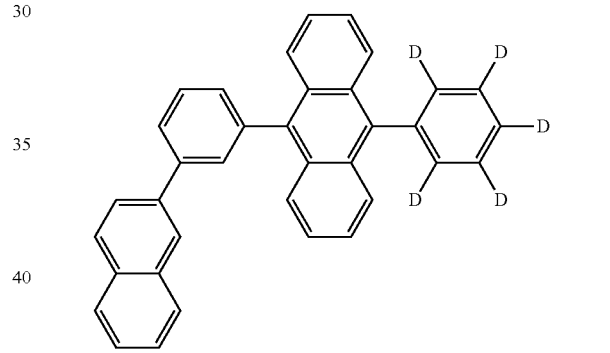
<Chemical Formula 9>
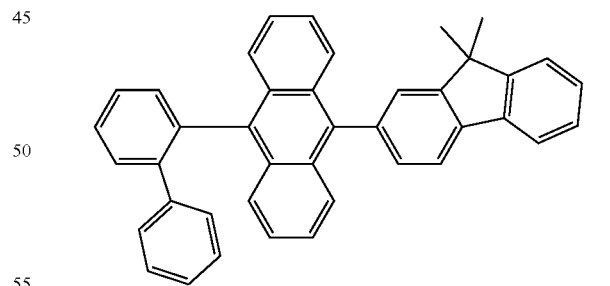
<Chemical Formula 10>
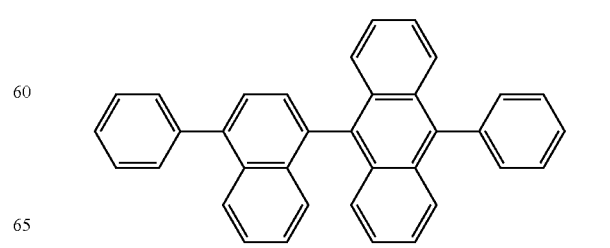

<Chemical Formula 11>
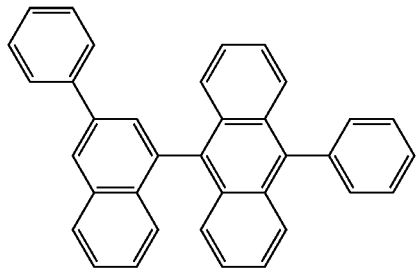
<Chemical Formula 12>
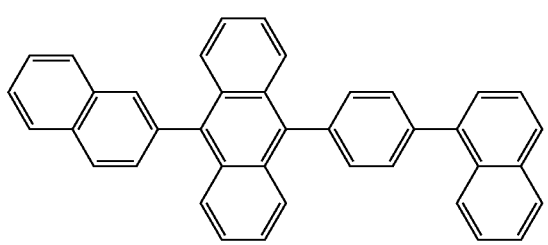
<Chemical Formula 13>
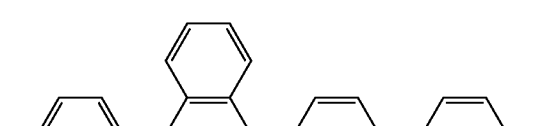
<Chemical Formula 14>
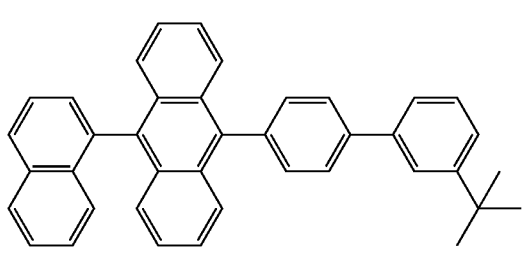
<Chemical Formula 15>
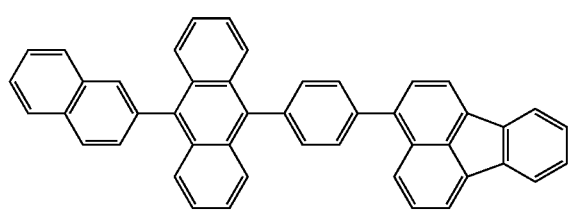
<Chemical Formula 16>
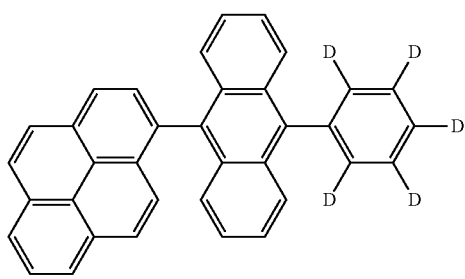
<Chemical Formula 17>
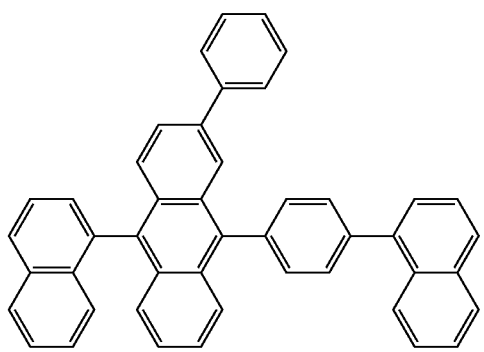
<Chemical Formula 18>
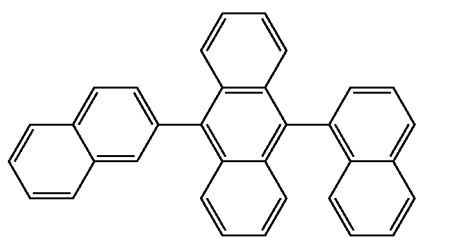
<Chemical Formula 19>
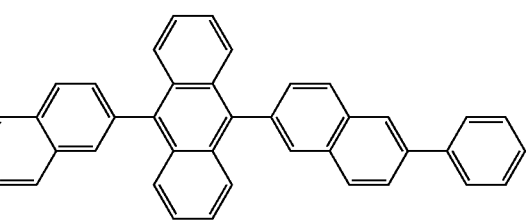
<Chemical Formula 20>
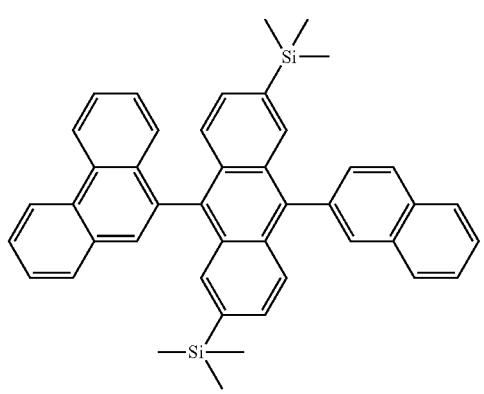
<Chemical Formula 21>
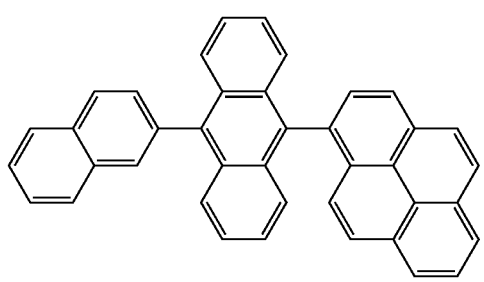

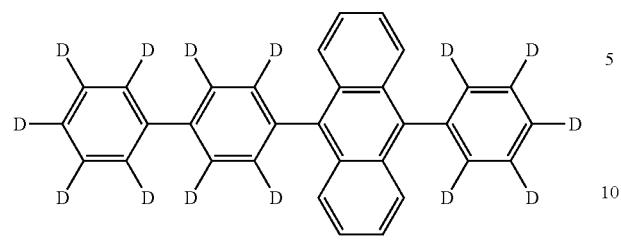

<Chemical Formula 30>
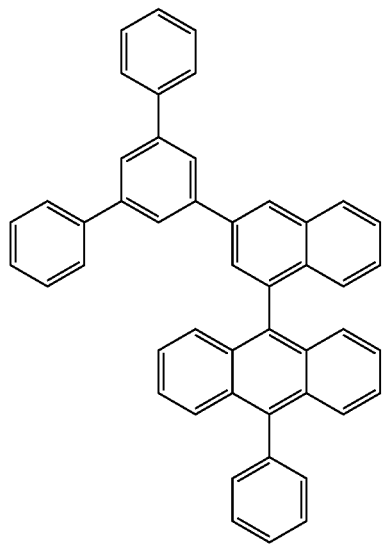
<Chemical Formula 31>
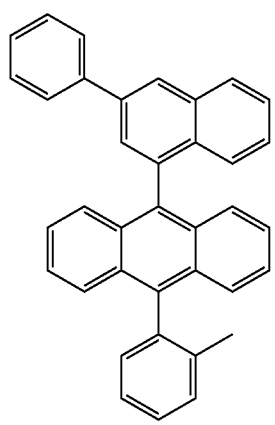
<Chemical Formula 32>
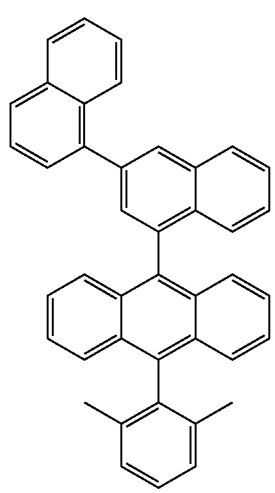
<Chemical Formula 33>
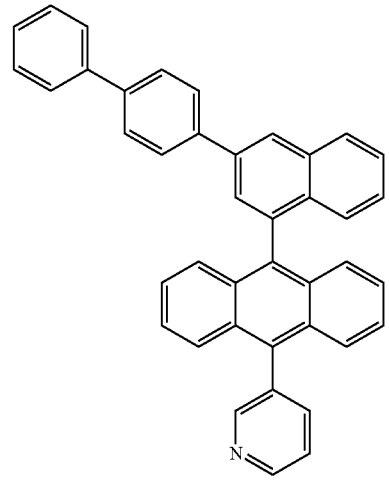
<Chemical Formula 34>
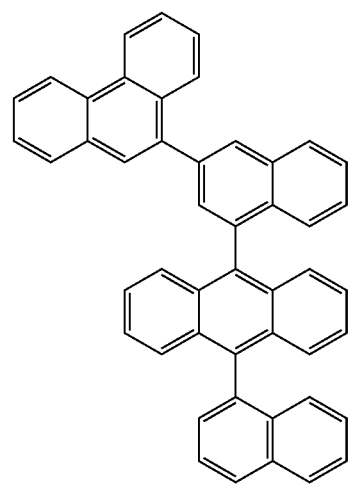
<Chemical Formula 35>
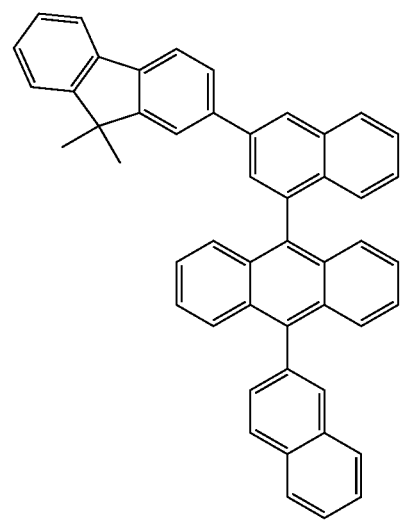

<Chemical Formula 36>
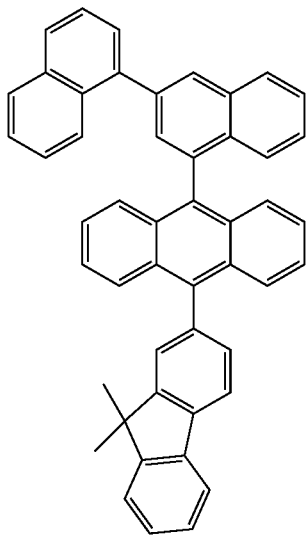
<Chemical Formula 37>
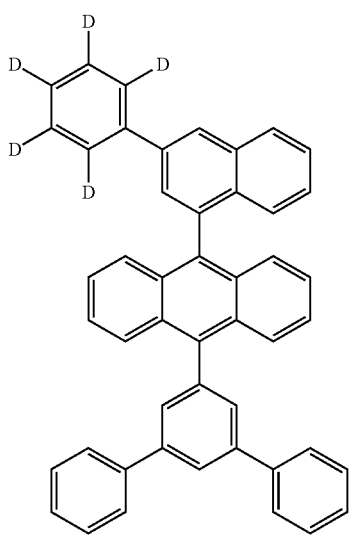
<Chemical Formula 38>
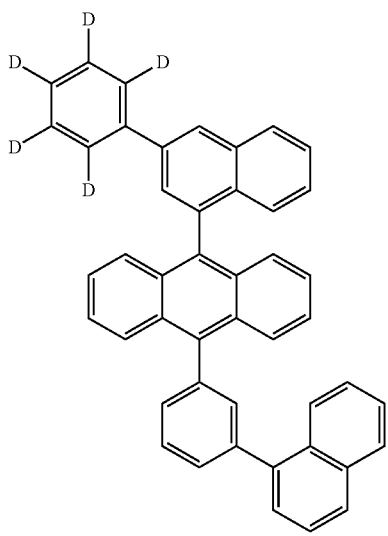
<Chemical Formula 39>
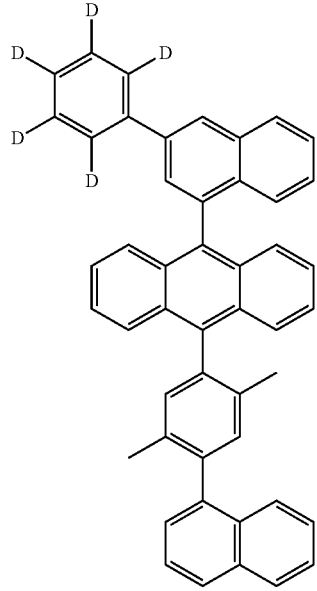
<Chemical Formula 40>
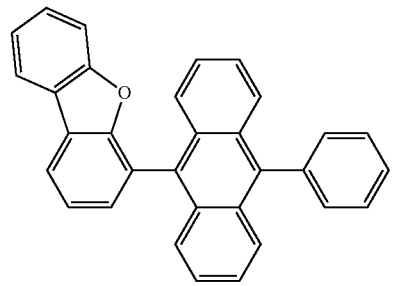
<Chemical Formula 41>
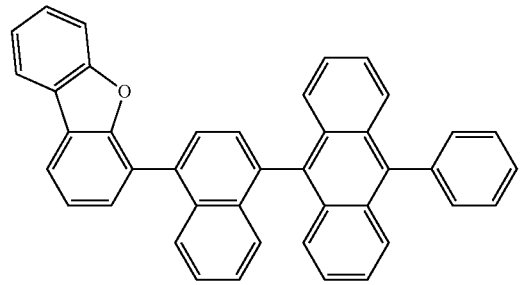
<Chemical Formula 42>
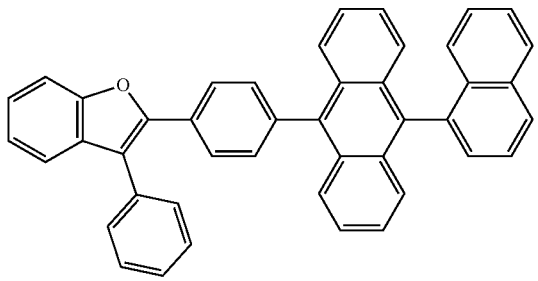

<Chemical Formula 43>
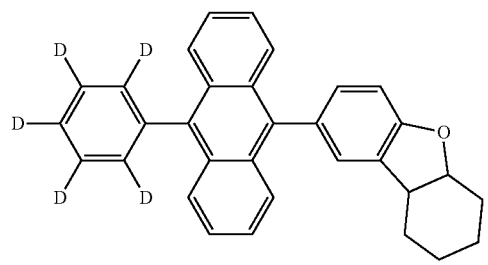
<Chemical Formula 44>
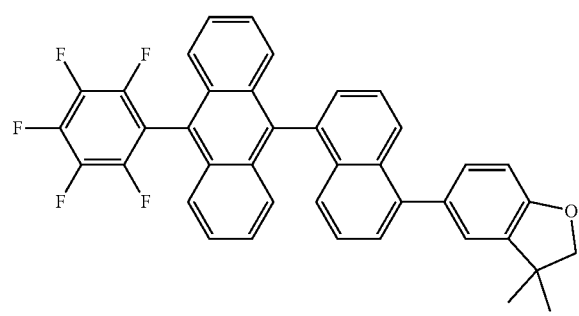
<Chemical Formula 45>
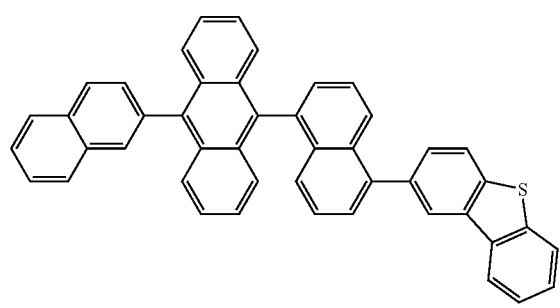
<Chemical Formula 46>
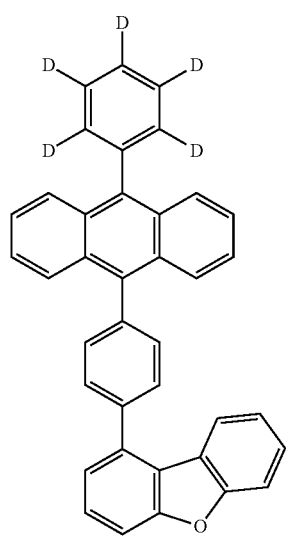
<Chemical Formula 47>
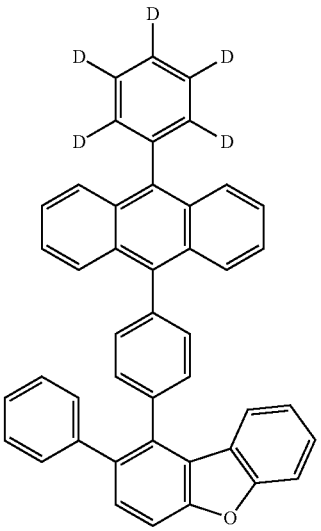
<Chemical Formula 48>
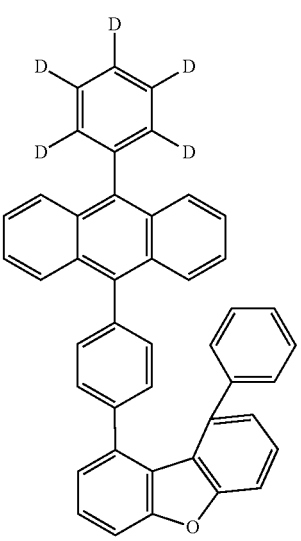
<Chemical Formula 49>
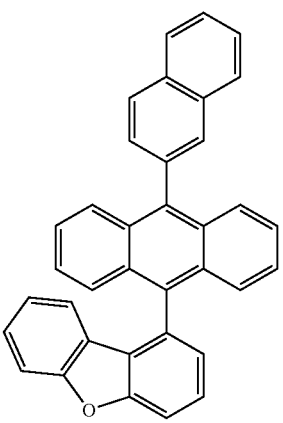

<Chemical Formula 50>
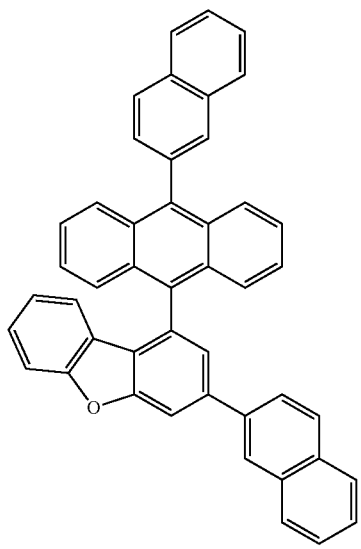
<Chemical Formula 51>
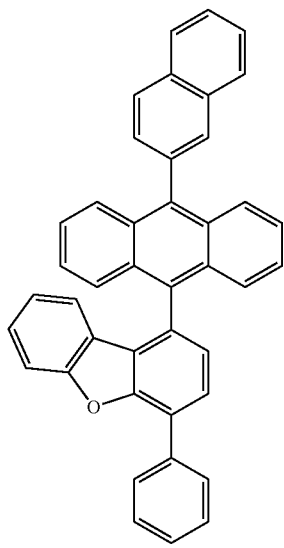
<Chemical Formula 52>
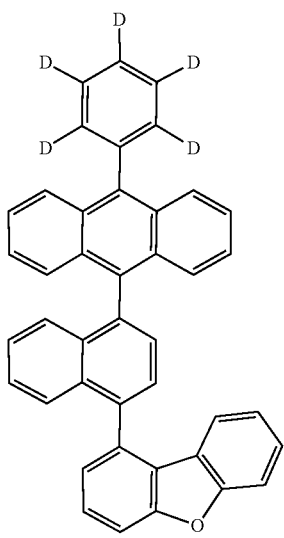
<Chemical Formula 53>
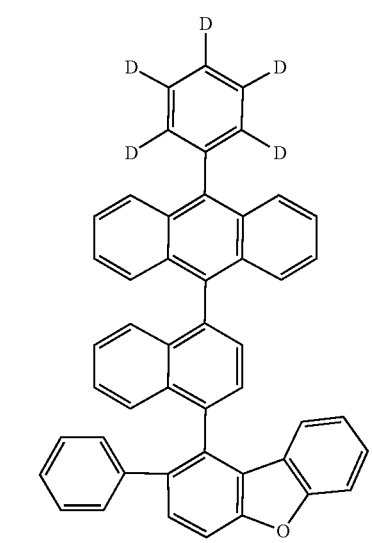
<Chemical Formula 54>
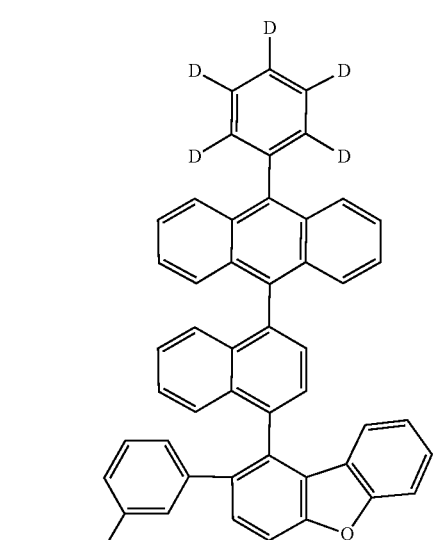
<Chemical Formula 55>
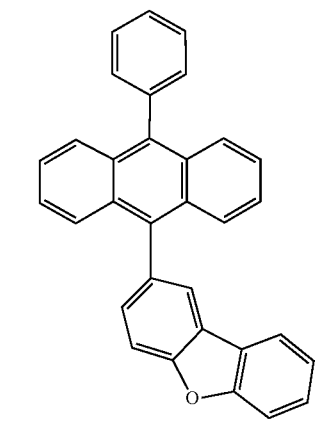

<Chemical Formula 56>
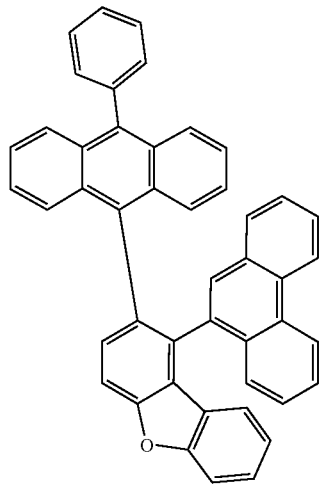
<Chemical Formula 57>
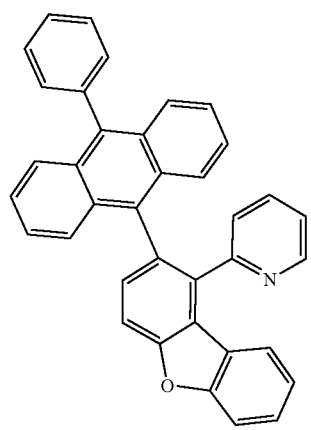
<Chemical Formula 58>
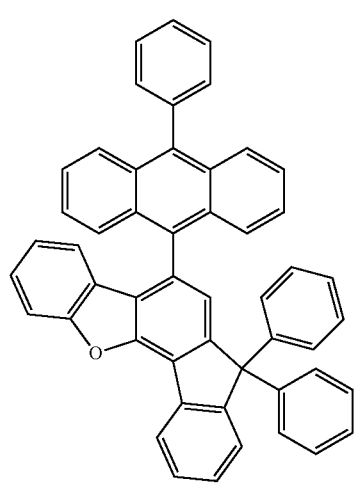
<Chemical Formula 59>
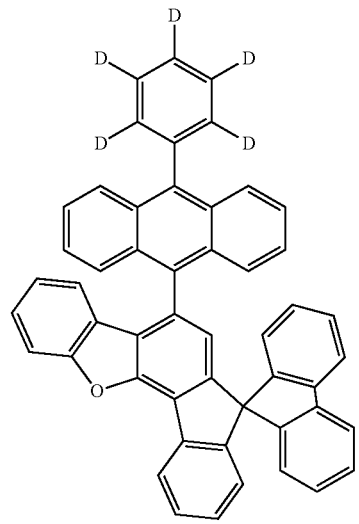
<Chemical Formula 60>
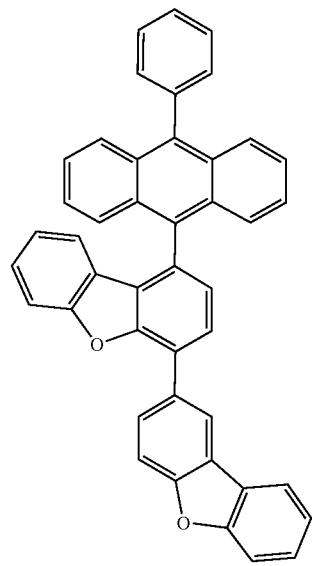
<Chemical Formula 61>
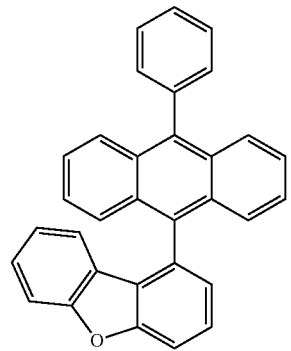

<Chemical Formula 62>

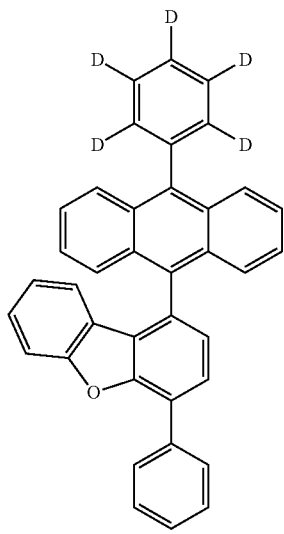

<Chemical Formula 63>

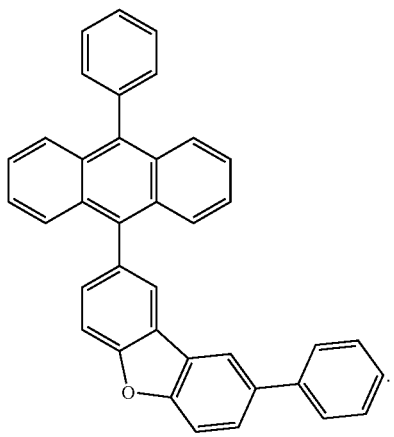

The light-emitting layer of the present disclosure includes a dopant which may be an amine compound represented by the following Chemical Formula B or C, or an amine compound represented by the following Chemical Formula D1 or D2. Preferable is an amine compound represented by the following Chemical Formula B or C:

[Chemical Formula B]

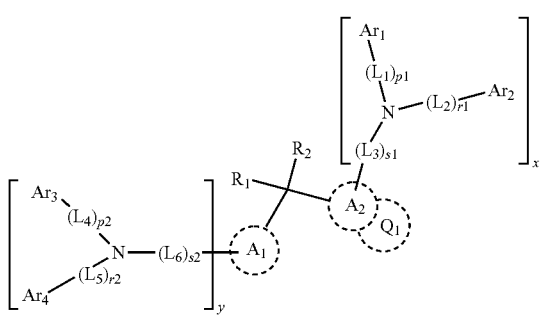

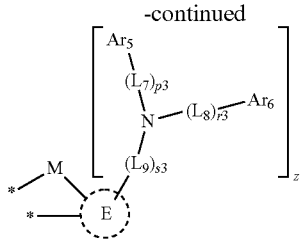

[Chemical Formula C]

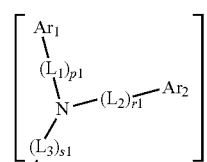

wherein, $A_1$, $A_2$, E, and F may be the same or different and are each independently a substituted or unsubstituted aromatic hydrocarbon ring of 6 to 50 carbon atoms or a substituted or unsubstituted heteroaromatic ring of 2 to 40 carbon atoms wherein two adjacent carbon atoms of the aromatic ring $A_1$ and two adjacent carbon atoms of the aromatic ring $A_2$ form a 5-membered fused ring with a carbon atom connected to both substituents $R_1$ and $R_2$;

linkers $L_1$ to $L_{12}$ may be the same or different, and are each independently selected from among a direct bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

M is any one selected from among N—$R_3$, $CR_4R_5$, $SiR_6R_7$, $GeR_8R_9$, O, S, and Se;

$R_1$ to $R_9$, and $Ar_1$ to $Ar_8$ may be the same or different, and are each independently any one selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a substituted or unsubstituted alkylgermanium of 1 to 30 carbon atoms, a substituted or unsubstituted arylgermanium of 6 to 30 carbon atoms, a cyano, a nitro, and a halogen, with the proviso that $R_1$ and $R_2$ may be bonded to each other to form a mono- or polycyclic aliphatic or aromatic ring, which may be a heterocyclic ring containing a heteroatom selected from among N, O, P, Si, S, Ge, Se, and Te as a ring member;

p1 to p4, $r_1$ to $r_4$, and s1 to s4 are each independently an integer of 1 to 3, with the proviso that when any of them is 2 or greater, the corresponding linkers L1's and L12's may be individually the same or different, x is an integer of 1 or 2, and y and z may be the same or different and are each independently an integer of 0 to 3; and a ring may be formed between $Ar_4$ and $Ar_2$, between $Ar_3$ and $Ar_4$, between $Ar_5$ and $Ar_6$, and between $Ar_7$ and $Ar_8$, two adjacent carbon atoms of the $A_2$ ring moiety of Chemical Formula B may occupy respective positions * of Structural Formula $Q_1$ to form a fused ring, and two adjacent carbon atoms of the $A_1$ ring moiety of Chemical Formula C may occupy respective positions * of structural Formula $Q_2$ to form a fused ring, and two adjacent carbon atoms of the $A_2$ ring moiety of Chemical Formula C may occupy respective positions * of Structural Formula $Q_4$ to form a fused ring, wherein the term 'substituted' in the expression 'substituted or unsubstituted' used in Chemical Formulas A and B means having at least one substituent selected from the group consisting of a deuterium atom, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 6 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a heteroarylamino of 1 to 24 carbon atoms, an alkylsilyl of 1 to 24 carbon atoms, an arylsilyl of 6 to 24 carbon atoms, and an aryloxy of 6 to 24 carbon atoms; and

[Chemical Formula D1]

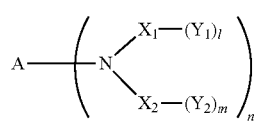

[Chemical Formula D2]

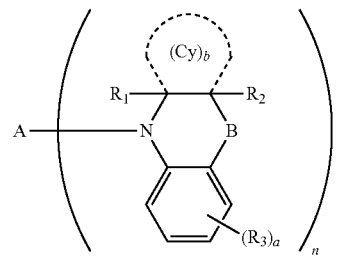

wherein,

A may be any one selected from among a substituted or unsubstituted aryl of 6 to 50 carbon atoms, a substituted or unsubstituted heteroaryl of 2 to 50 carbon atoms bearing O, N, or S as a heteroatom, a substituted or unsubstituted arylene of 6 to 60 carbon atoms, and a substituted or unsubstituted heteroarylene of 2 to 50 carbon atoms bearing O, N, or S as a heteroatom.

In greater detail, A may be a substituted or unsubstituted arylene of 6 to 60 carbon atoms, or a single bond, particularly any one selected from among anthracene, pyrene, phenanthrene, indenophenanthrene, chrysene, naphthacene, pycene, triphenylene, perylene, and pentacene, and more particularly a substituent represented by the following Chemical Formula s A1 to A10:

[Chemical Formula A1]

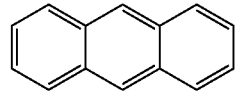

[Chemical Formula A2]

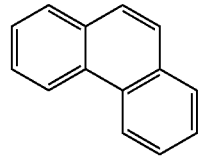

[Chemical Formula A3]

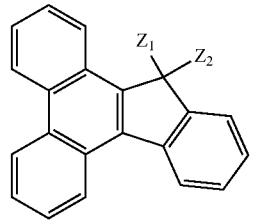

[Chemical Formula A4]

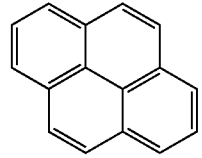

[Chemical Formula A5]

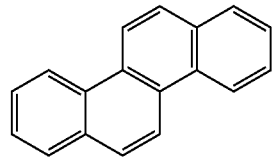

-continued

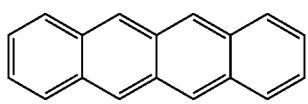
[Chemical Formula A6]

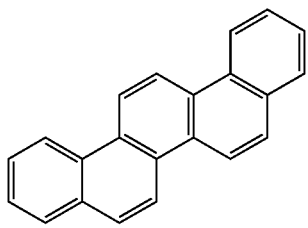
[Chemical Formula A7]

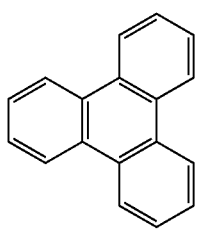
[Chemical Formula A8]

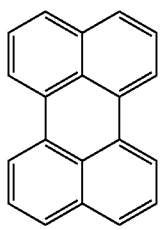
[Chemical Formula A9]

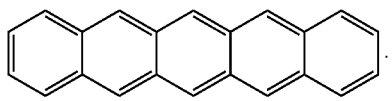
[Chemical Formula A10]

In Chemical Formula A3, $Z_1$ and $Z_2$ may be the same or different and are each independently selected from the group consisting of a hydrogen atom, a deuterium atom, a substituted or unsubstituted alkyl of 1 to 60 carbon atoms, a substituted or unsubstituted alkenyl of 2 to 60 carbon atoms, a substituted or unsubstituted alkynyl of 2 to 60 carbon atoms, a substituted or unsubstituted alkoxy of 1 to 60 carbon atoms, a substituted or unsubstituted alkylthio of 1 to 60 carbon atoms, a substituted or unsubstituted cycloalkyl of 3 to 60 carbon atoms, a substituted or unsubstituted aryl of 6 to 60 carbon atoms, a substituted or unsubstituted aryloxy of 6 to 60 carbon atoms, a substituted or unsubstituted arylthio of 6 to 60 carbon atoms, a substituted or unsubstituted heteroaryl of 2 to 60 carbon atoms, a substituted or unsubstituted (alkyl)amino of 1 to 60 carbon atoms, a di(substituted or unsubstituted alkyl)amino of 1 to 60 carbon atoms or a (substituted or unsubstituted aryl)amino of 6 to 60 carbon atoms, and a di(substituted or unsubstituted aryl) amino of 6 to 60 carbon atom, with the proviso that $Z_1$ and $Z_2$ may each form a fused ring with an adjacent radical.

In Chemical Formula D1, $X_1$ and $X_2$ may each be independently a substituted or unsubstituted arylene of 6 to 30 carbon atoms or a single bond, with the proviso that $X_1$ and $X_2$ may bond to each other, $Y_1$ and $Y_2$ may be the same or different and are each independently selected from the group consisting of a substituted or unsubstituted aryl of 6 to 24 carbon atoms, a substituted or unsubstituted a heteroaryl of 2 to 24 carbon atoms, a substituted or unsubstituted alkyl of 1 to 24 carbon atoms, a substituted or unsubstituted a heteroalkyl of 1 to 24 carbon atoms, a substituted or unsubstituted cycloalkyl of 3 to 24 carbon atoms, a substituted or unsubstituted alkoxy of 1 to 24 carbon atoms, a cyano, a halogen, a substituted or unsubstituted aryloxy of 6 to 24 carbon atoms, a substituted or unsubstituted alkylsilyl of 1 to 40 carbon atoms, a substituted or unsubstituted arylsilyl of 6 to 30 carbon atoms, a germanium, a phosphorus, a boron, a deuterium, and a hydrogen, with the proviso that $Y_1$ and $Y_2$ may be the same or different and may each form with an aliphatic, aromatic, heteroaliphatic or heteroaromatic fused ring with an adjacent radical, l and m are each an integer of 1 to 20, and n is an integer of 1 to 4.

In Chemical Formula D2, $C_y$ is a substituted or unsubstituted cycloalkyl of 3 to 8 carbon atoms and b is an integer of 1 to 4, with the proviso that when b is 2 or greater, the corresponding cycloalkanes may be the same or different and may be in a fused form having a deuterium or an alkyl as a substituent.

B is a single bond or —$[C(R_5)(R_6)]_p$— wherein p is an integer of 1 to 3, with the proviso that when p is 2 or greater, the corresponding $R_5$'s and $R_6$'s are individually the same or different;

$R_1$, $R_2$, $R_3$, $R_5$, and $R_6$ may each be independently selected from among a hydrogen atom, a deuterium atom, a halogen atom, a hydroxyl, a cyano, a nitro, an amino, an amidino, a hydrazine, a hydrazone, a carboxyl or a salt thereof, a sulfonic acid or a salt thereof, a phosphoric acid or a salt thereof, a substituted or unsubstituted alkyl of 1 to 60 carbon atoms, a substituted or unsubstituted alkenyl of 2 to 60 carbon atoms, a substituted or unsubstituted alkynyl of 2 to 60 carbon atoms, a substituted or unsubstituted alkoxy of 1 to 60 carbon atoms, a substituted or unsubstituted alkylthio of 1 to 60 carbon atoms (alkylthio), a substituted or unsubstituted cycloalkyl of 3 to 60 carbon atoms, a substituted or unsubstituted aryl of 6 to 60 carbon atoms, a substituted or unsubstituted aryloxy of 6 to 60 carbon atoms, a substituted or unsubstituted arylthio of 6 to 60 carbon atoms, a substituted or unsubstituted heteroaryl of 2 to 60 carbon atoms, a substituted or unsubstituted (alkyl)amino of 1 to 60 carbon atoms, a di(substituted or unsubstituted alkyl)amino of 1 to 60 carbon atoms or a (substituted or unsubstituted aryl)amino of 6 to 60 carbon atoms, and a di(substituted or unsubstituted aryl)amino of 6 to 60 carbon atoms, a substituted or unsubstituted alkylsilyl of 1 to 40 carbon atoms, a substituted or unsubstituted arylsilyl of 6 to 30 carbon atoms, a germanium, a phosphorus, and a boron, and a is an integer of 1 to 4, with the proviso that a is 2 or greater, the corresponding plural $R_3$'s may be the same or different and may be individually in a fused form, and n is an integer of 1 to 4.

According to a particular embodiment of the present disclosure, $A_1$, $A_2$, E, and F ring moieties in Chemical Formula B or C may be the same or different and are each independently substituted or unsubstituted aromatic hydrocarbon rings of 6 to 50 carbon atoms. In this regard, the substituted or unsubstituted aromatic hydrocarbon rings of 6 to 50 carbon atoms may be the same or different and each be independently selected from among compounds represented by Structural Formulas 10 to 21:

[Structural Formula 10]

[Structural Formula 11]

[Structural Formula 12]

[Structural Formula 13]

[Structural Formula 14]

[Structural Formula 15]

[Structural Formula 16]

[Structural Formula 17]

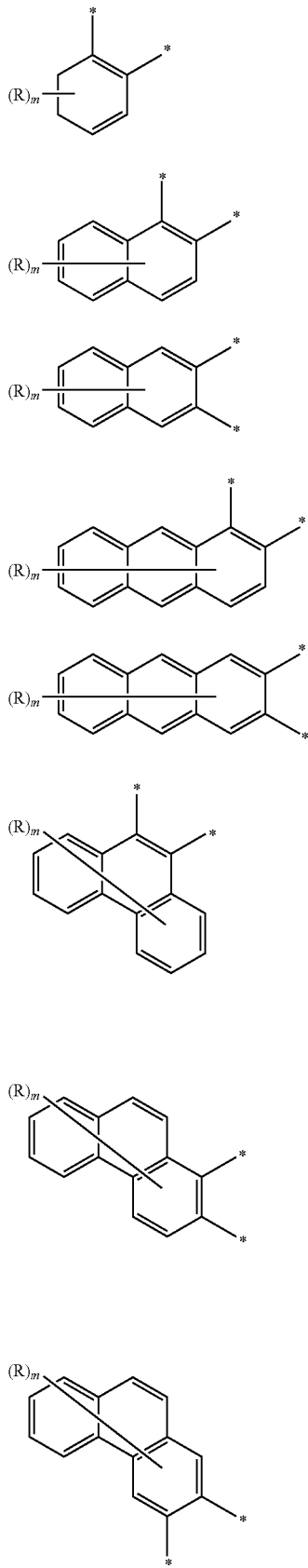

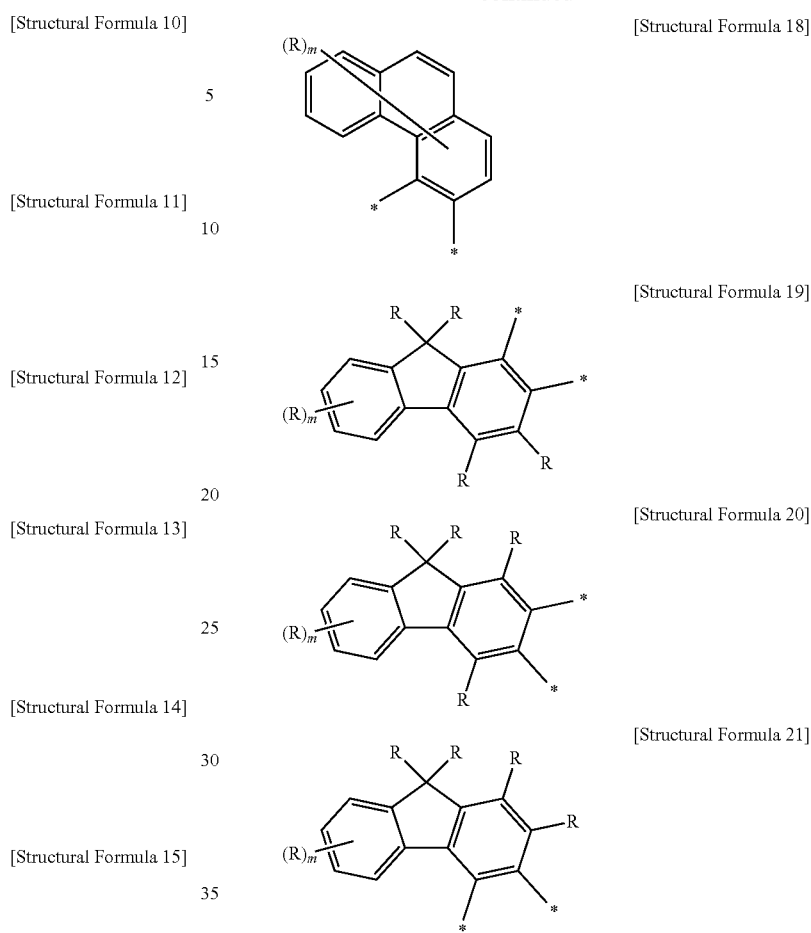

[Structural Formula 18]

[Structural Formula 19]

[Structural Formula 20]

[Structural Formula 21]

wherein,

"-*" denotes a bonding site for forming a 5-membered ring bearing the carbon atom connected to the substituents $R_1$ and $R_2$ or a bonding site for forming a 5-membered ring bearing M of Structural Formulas $Q_1$ and $Q_2$;

when one of the aromatic hydrocarbon rings of [Structural Formula 10] to [Structural Formula 21] for $A_1$ or $A_2$ is bonded to Structural Formula $Q_1$ or $Q_2$, two adjacent carbon atoms of the aromatic hydrocarbon ring occupy respective positions * of Structural Formula $Q_1$ or $Q_2$ to form a fused ring;

R's are the same as defined above for $R_1$ and $R_2$, and m is an integer of 1 to 8, with the proviso that when m is 2 or greater or two or more R's exist, the corresponding R's may be the same or different.

According to one embodiment of the present disclosure, the linkers $L_1$ to $L_{12}$ in Chemical Formula B or C may be a single bond or one selected from among a substituted or unsubstituted arylene of 6 to 20 carbon atoms, and a substituted or unsubstituted heteroarylene of 2 to 20 carbon atoms, and particularly may be a single bond or one selected from among compound represented by the following Structural Formulas 22 to 30 and in this case, p1 to p4, r1 to r4, and s1 to s4 in Chemical Formula B or C may each be 1 or 2 and x may be 1:

[Structural Formula 22]
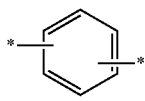

[Structural Formula 23]
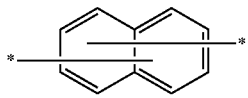

[Structural Formula 24]
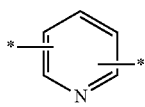

[Structural Formula 25]
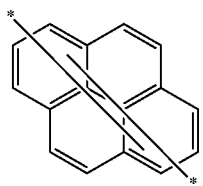

[Structural Formula 26]
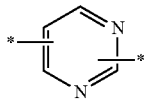

[Structural Formula 27]
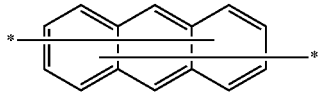

[Structural Formula 28]
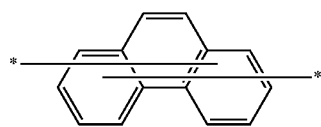

[Structural Formula 29]
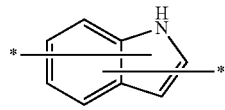

[Structural Formula 30]
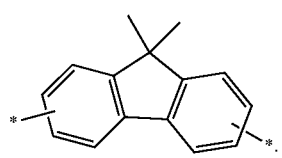

In the linkers, each of the unsubstituted carbon atoms of the aromatic ring moiety is bound with a hydrogen atom or a deuterium atom.

Preferable is a compound of Chemical Formula B or C in which y is 1 and z is zero. In addition, the substituents $R_1$ and $R_2$, which may be the same or different, are each independently a substituted or unsubstituted and may be connected to form a ring or may not.

In the amine compound of Chemical Formula B or C according to some embodiments of the present disclosure, $A_1$, $A_2$, E, F, $Ar_1$ to $Ar_8$, $L_1$ to $L_{12}$, and $R_1$ to $R_9$ may have as a substituent any one selected from the group consisting of a cyano, a halogen, an alkyl of 1 to 6 carbon atoms, an aryl of 6 to 18 carbon atoms, an arylalkyl of 6 to 18 carbon atoms, a heteroaryl of 3 to 18 carbon atoms, an alkylsilyl of 1 to 12 carbon atoms, and an arylsilyl of 6 to 18 carbon atoms.

The compound represented by Chemical Formula B or C may be concretely exemplified by the compounds of the following Chemical Formulas 101 to 339, but is not limited thereto:

<Chemical Formula 101>
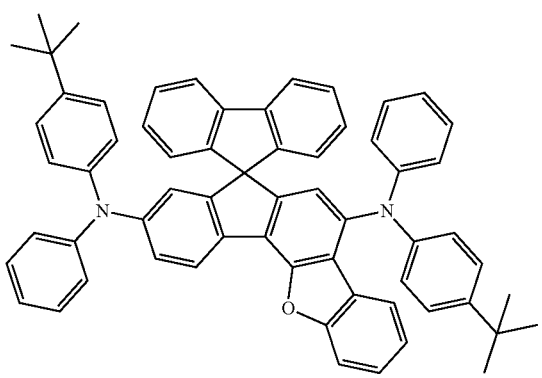

<Chemical Formula 102>
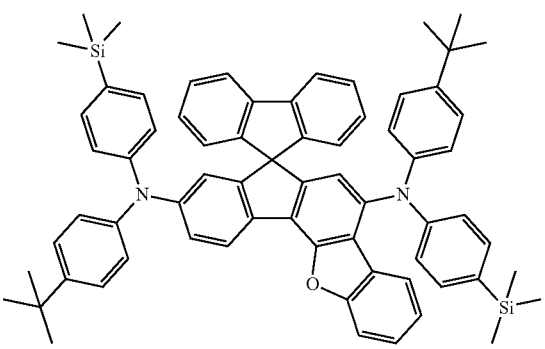

-continued
<Chemical Formula 103>
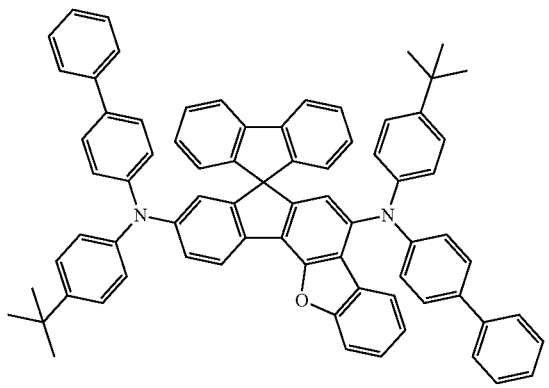
<Chemical Formula 104>
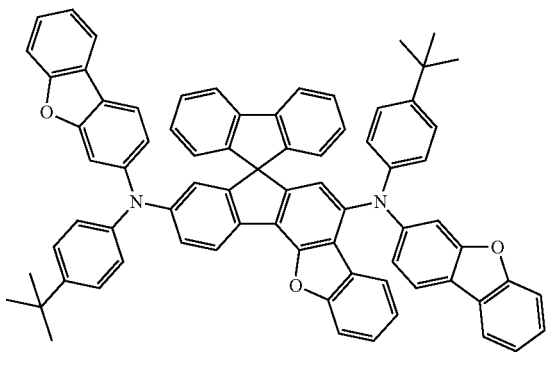
<Chemical Formula 105>
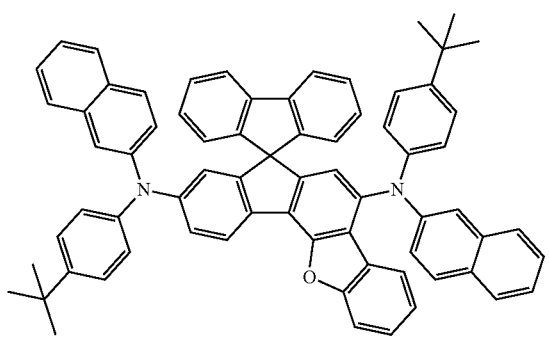
<Chemical Formula 106>
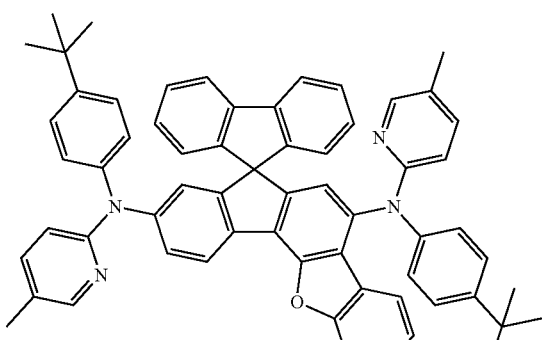
<Chemical Formula 107>
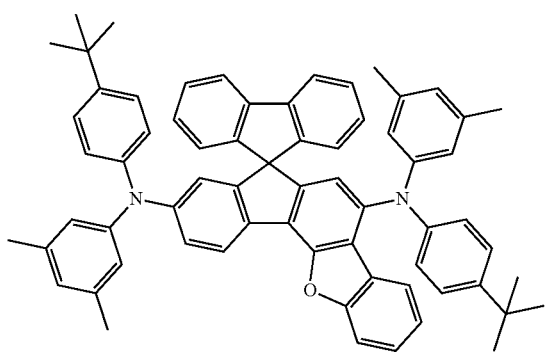
<Chemical Formula 108>
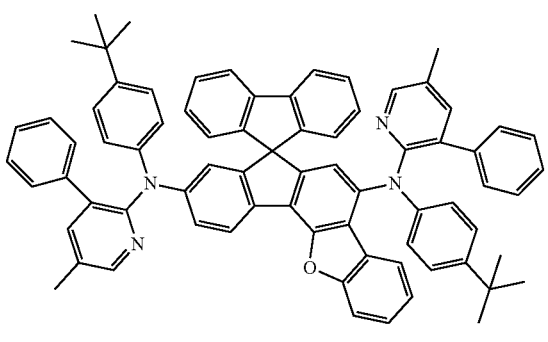
<Chemical Formula 109>
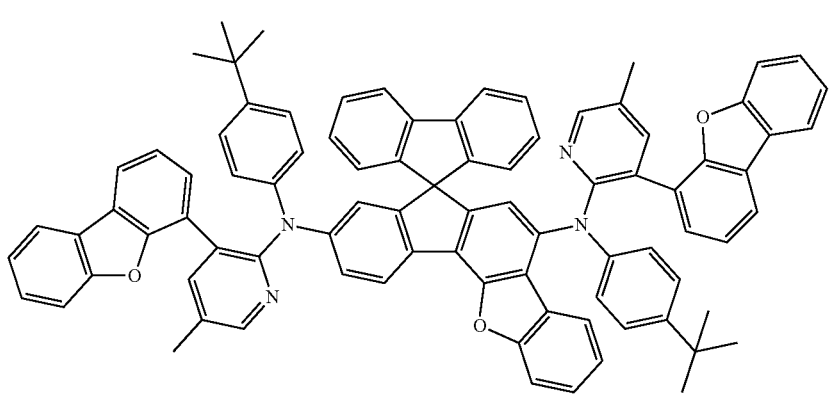

-continued
<Chemical Formula 110>
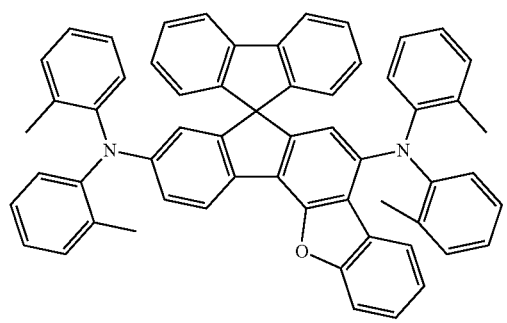
<Chemical Formula 111>
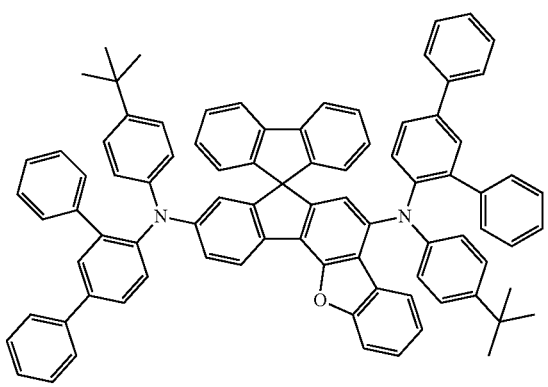
<Chemical Formula 112>
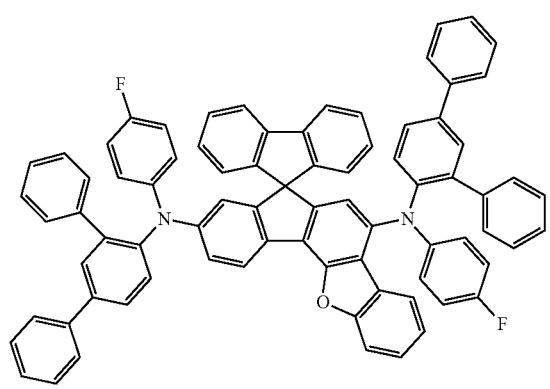
<Chemical Formula 113>
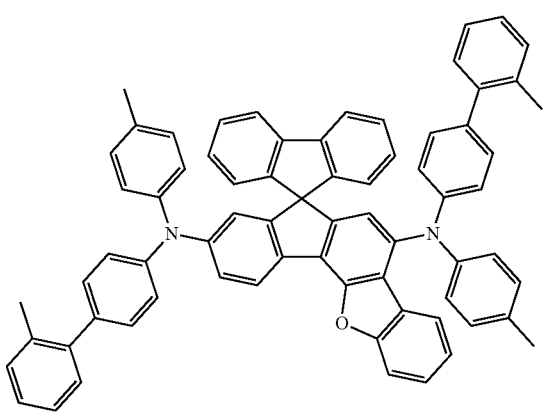
<Chemical Formula 114>
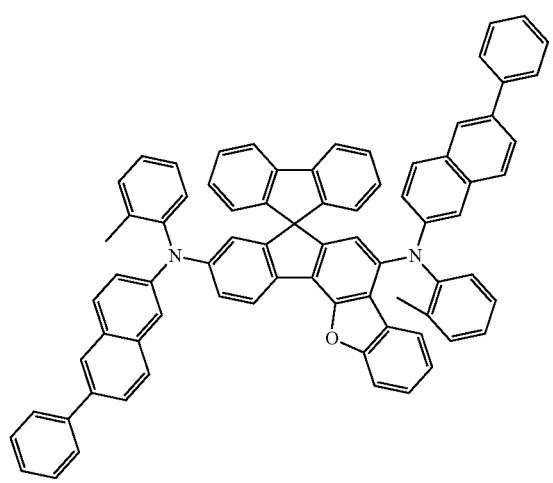
<Chemical Formula 115>
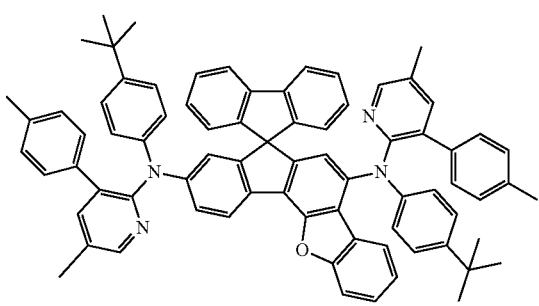

-continued
<Chemical Formula 116>
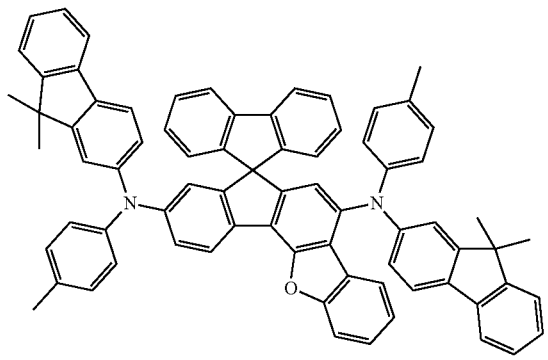
<Chemical Formula 117>
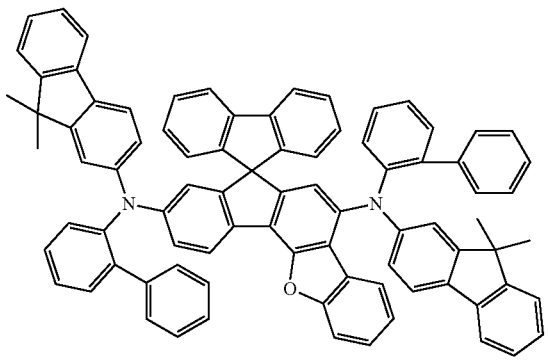
<Chemical Formula 118>
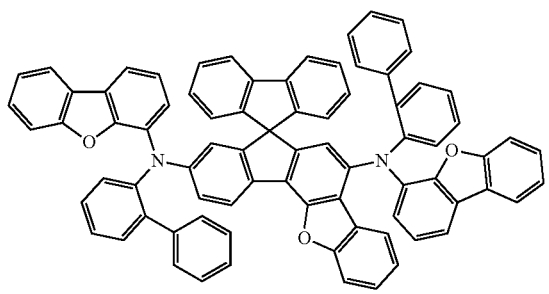
<Chemical Formula 119>
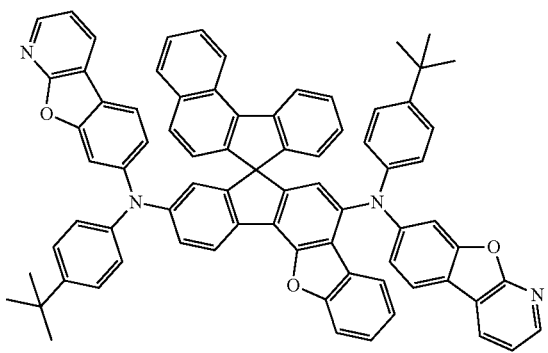
<Chemical Formula 120>
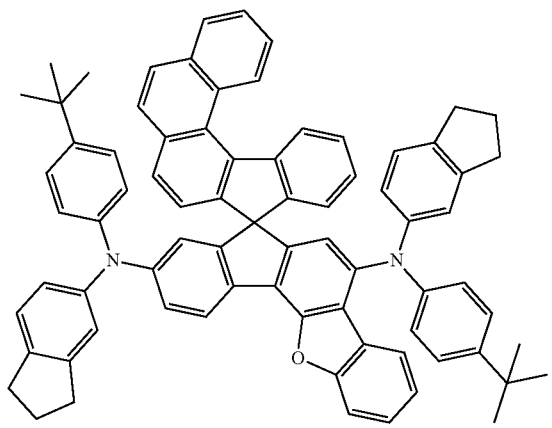
<Chemical Formula 121>
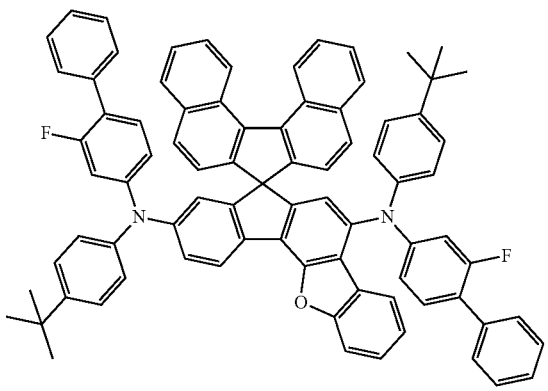
<Chemical Formula 122>
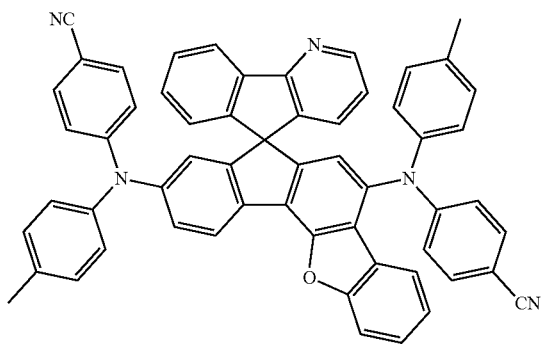
<Chemical Formula 123>
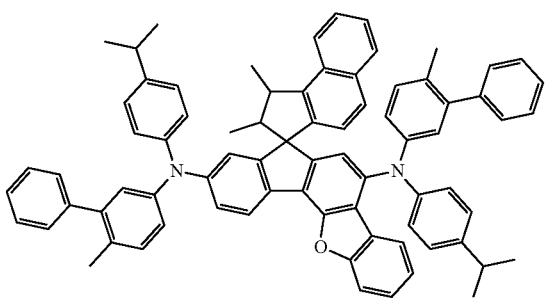

-continued
<Chemical Formula 124>
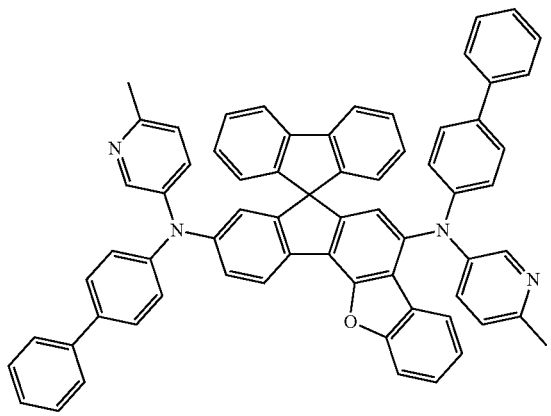
<Chemical Formula 125>
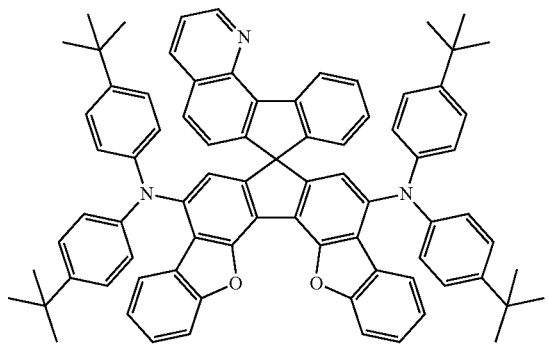
<Chemical Formula 126>
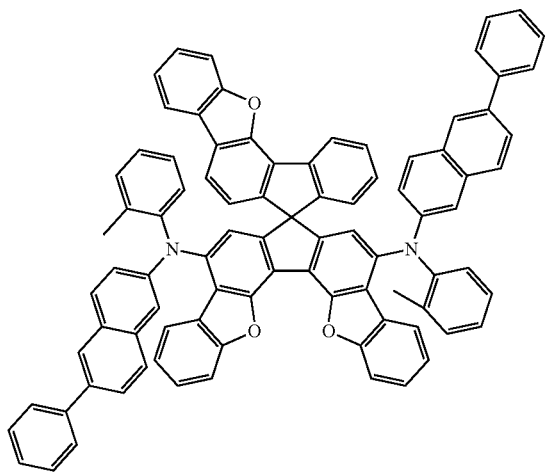
<Chemical Formula 127>
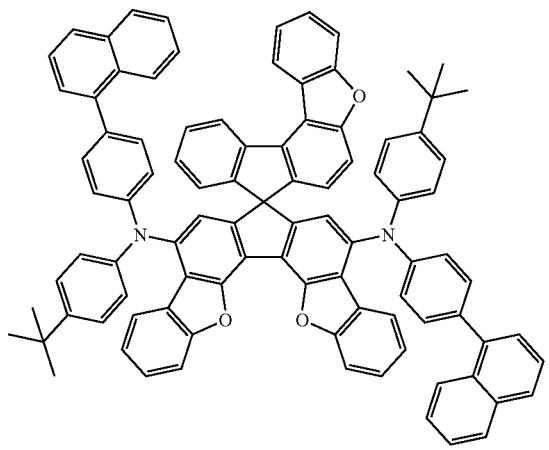
<Chemical Formula 128>
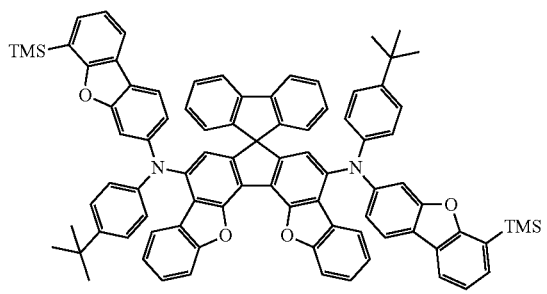
<Chemical Formula 129>
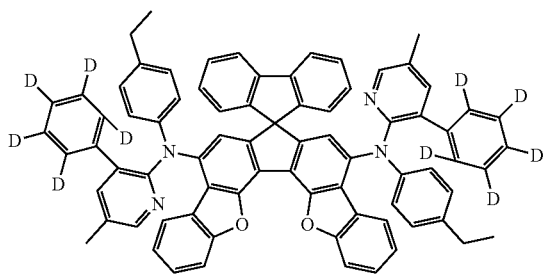
<Chemical Formula 130>
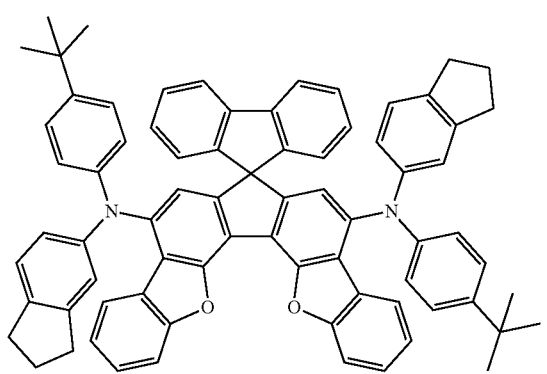
<Chemical Formula 131>
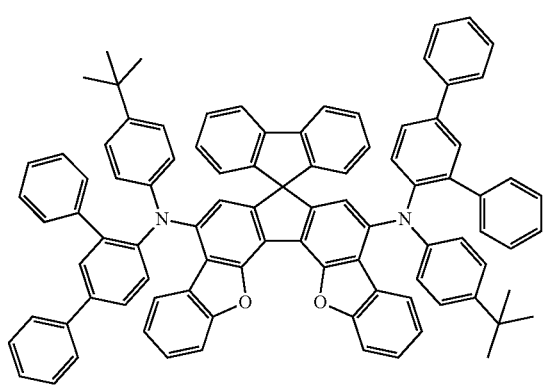

<Chemical Formula 132>
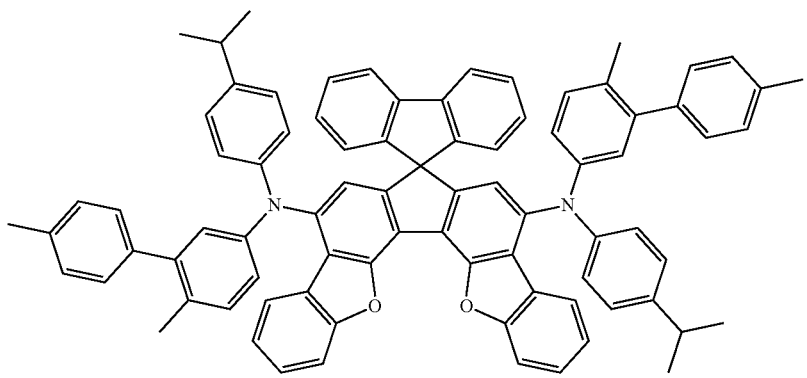
<Chemical Formula 133>
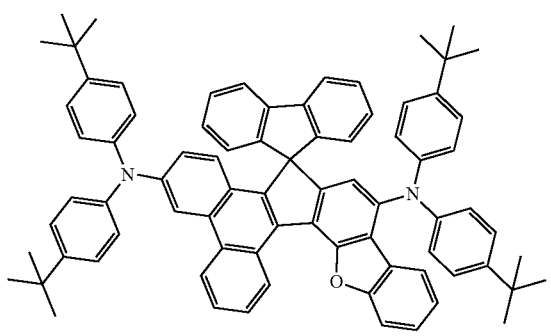
<Chemical Formula 134>
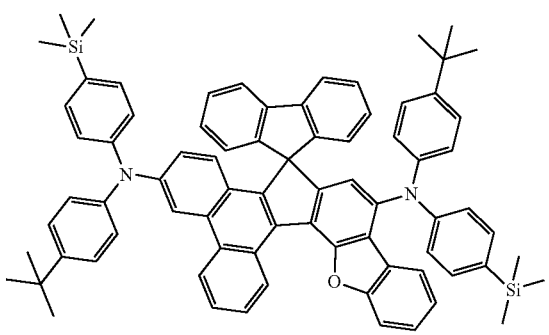
<Chemical Formula 135>
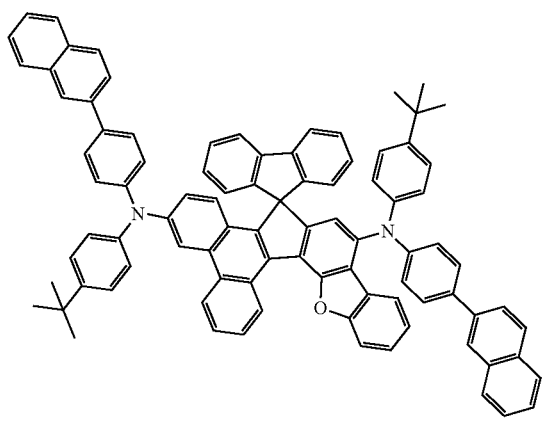
<Chemical Formula 136>
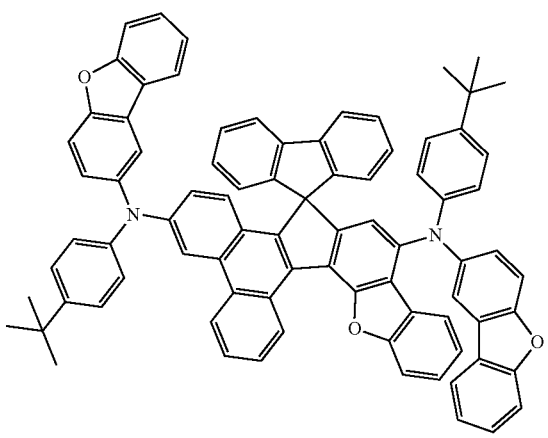
<Chemical Formula 137>
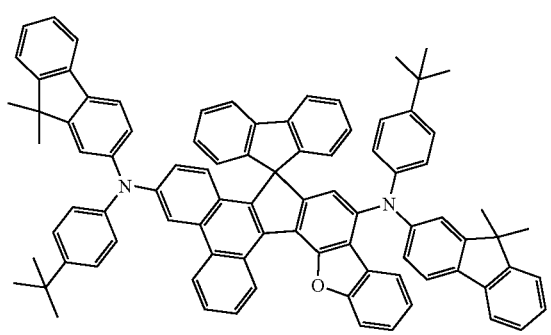
<Chemical Formula 138>
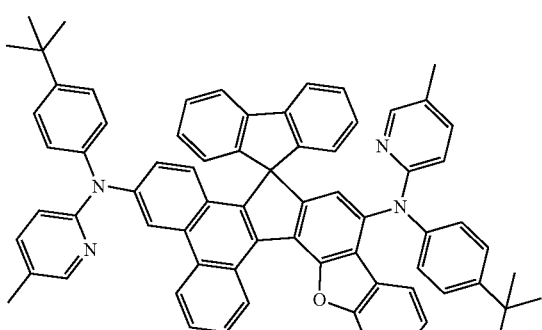

-continued
<Chemical Formula 139>
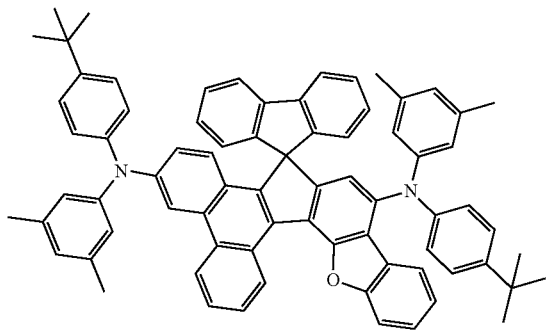
<Chemical Formula 140>
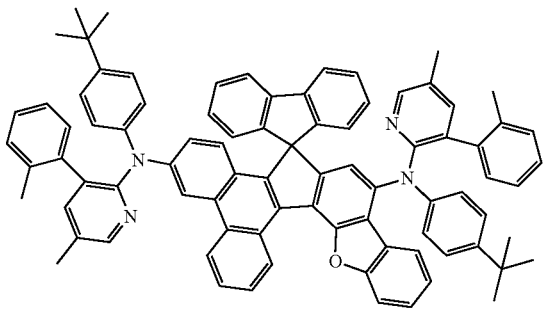
<Chemical Formula 141>
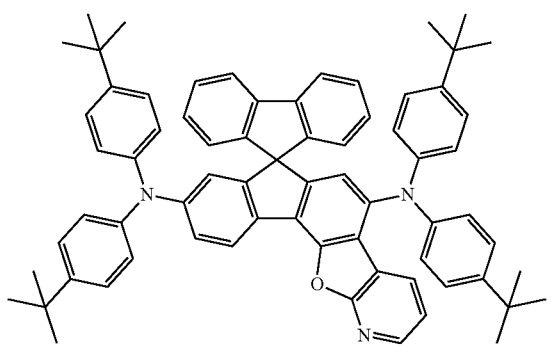
<Chemical Formula 142>
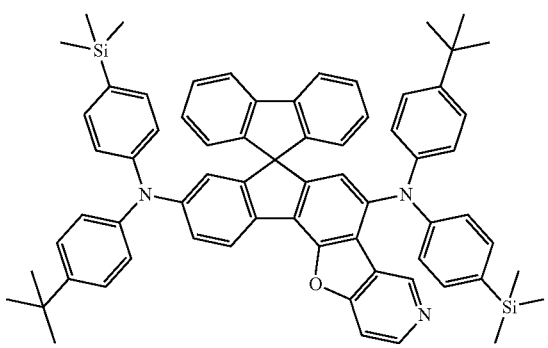
<Chemical Formula 143>
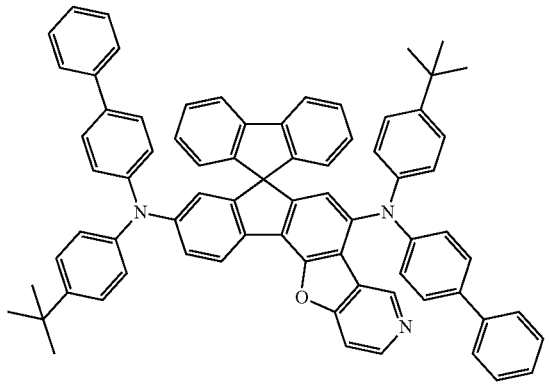
<Chemical Formula 144>
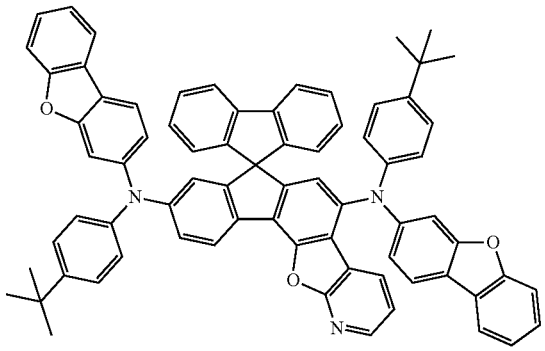
<Chemical Formula 145>
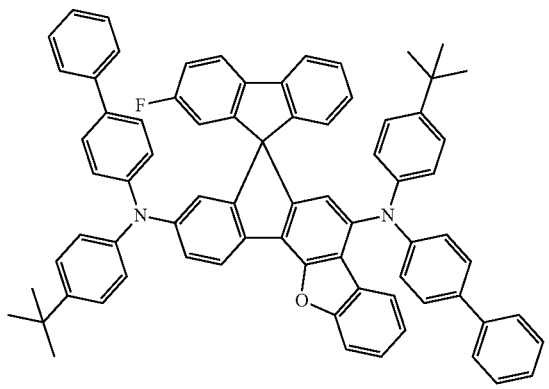
<Chemical Formula 146>
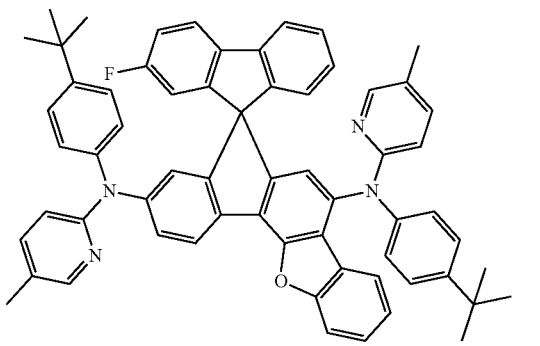

-continued
<Chemical Formula 147>
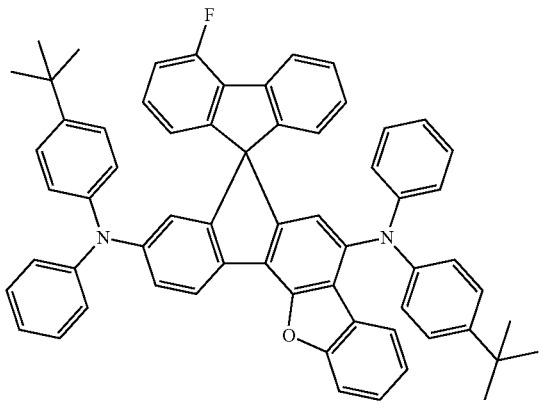
<Chemical Formula 148>
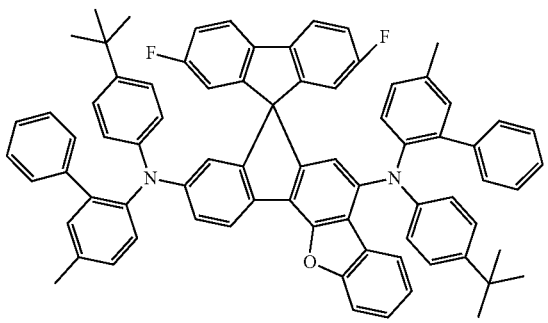
<Chemical Formula 149>
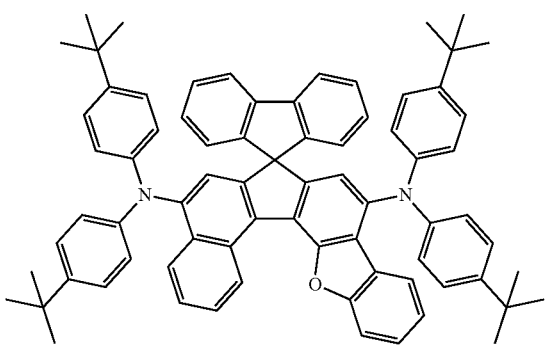
<Chemical Formula 150>
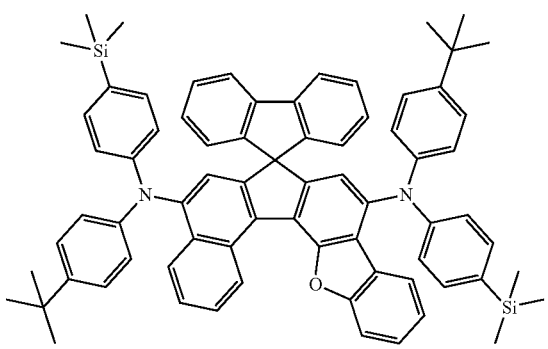
<Chemical Formula 151>
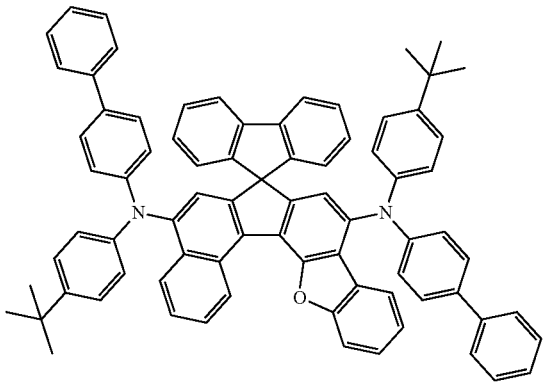
<Chemical Formula 152>
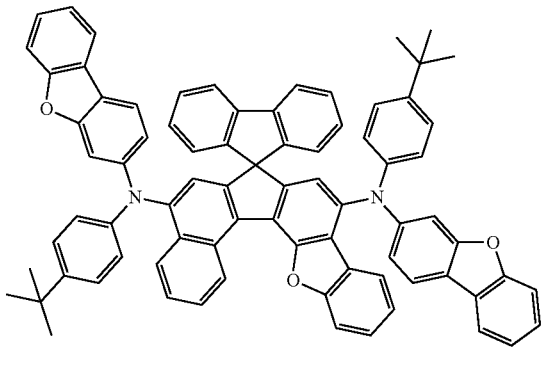
<Chemical Formula 153>
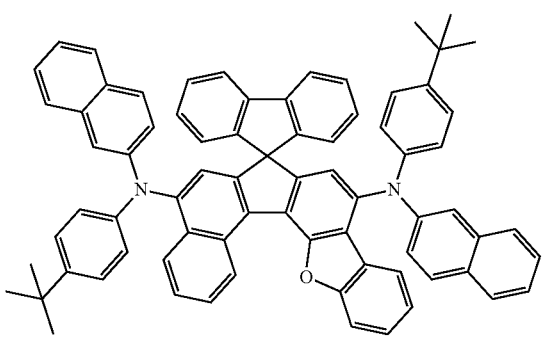
<Chemical Formula 154>
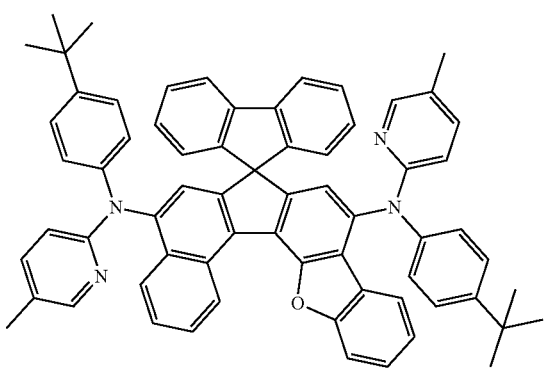

<Chemical Formula 155>
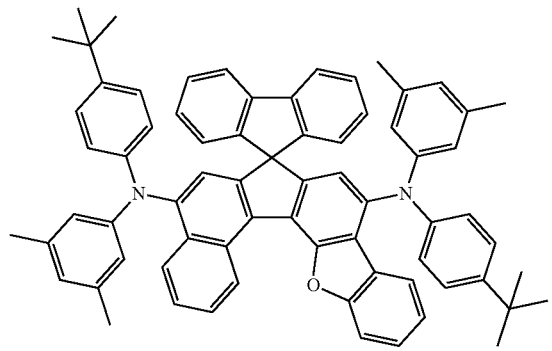
<Chemical Formula 156>
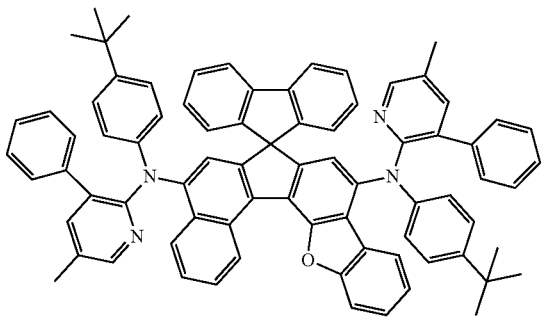
<Chemical Formula 157>
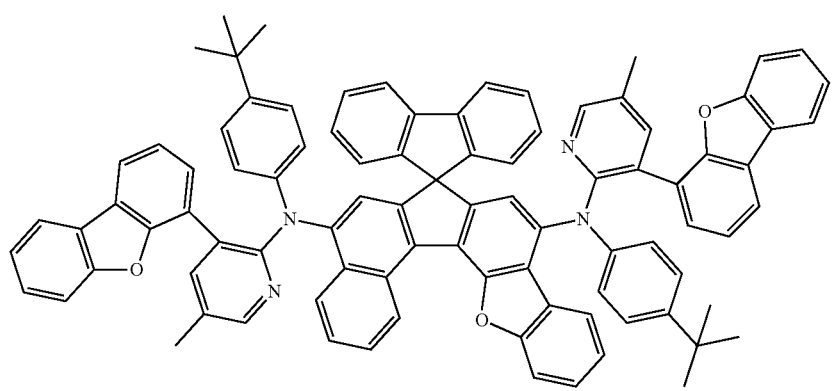
<Chemical Formula 158>
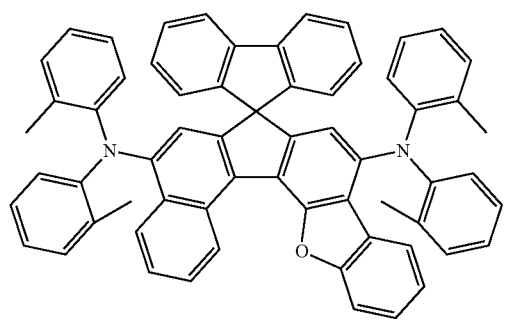
<Chemical Formula 159>
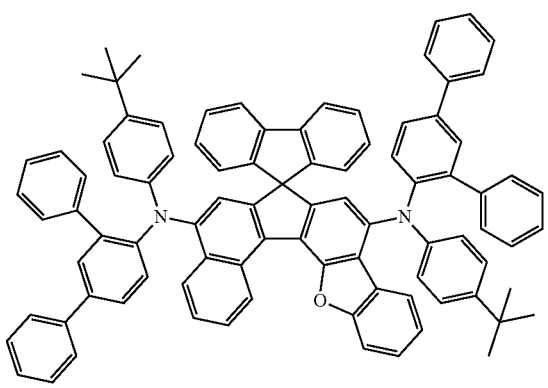
<Chemical Formula 160>
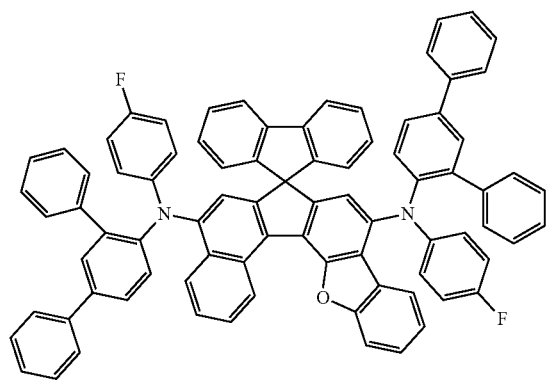
<Chemical Formula 161>
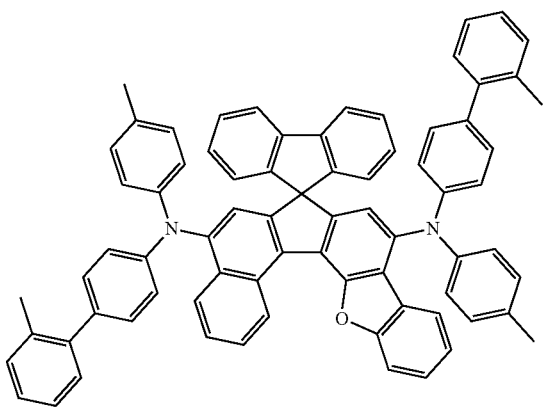

-continued
<Chemical Formula 162>
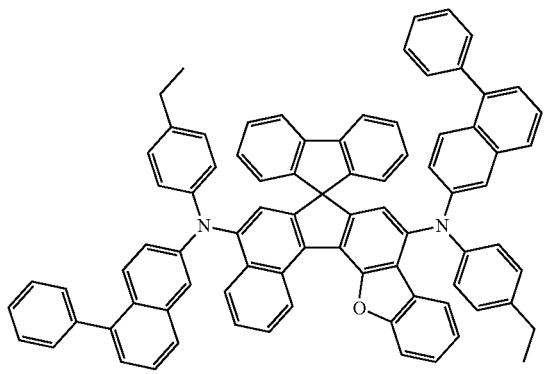
<Chemical Formula 163>
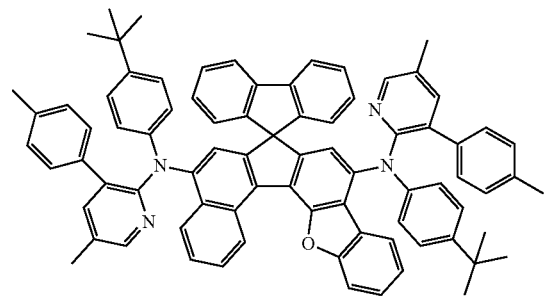
<Chemical Formula 164>
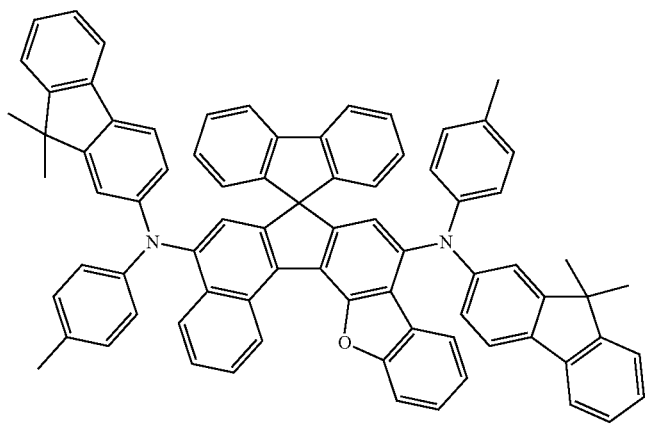
<Chemical Formula 165>
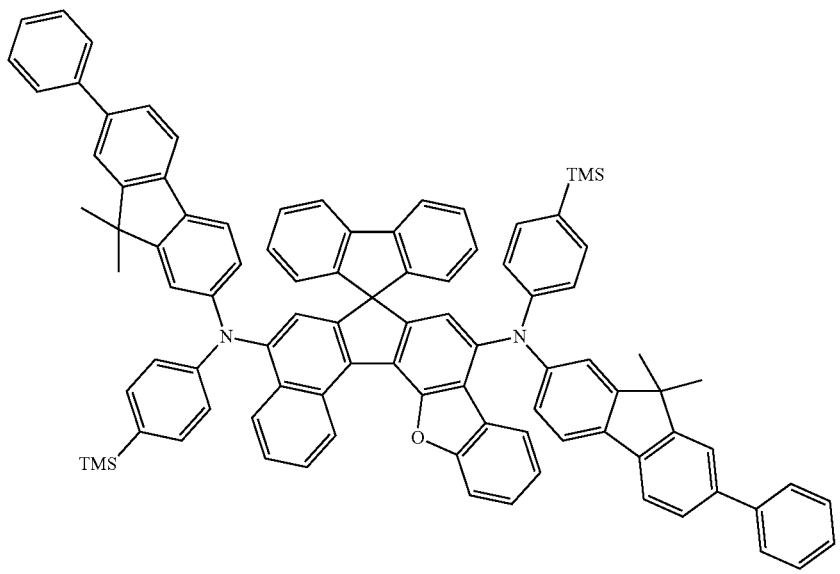

<Chemical Formula 166>
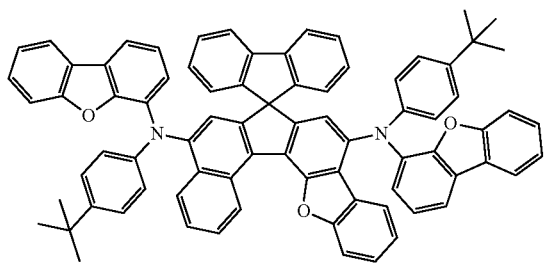
<Chemical Formula 167>
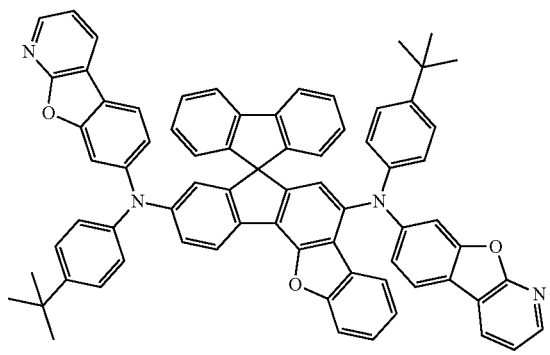
<Chemical Formula 168>
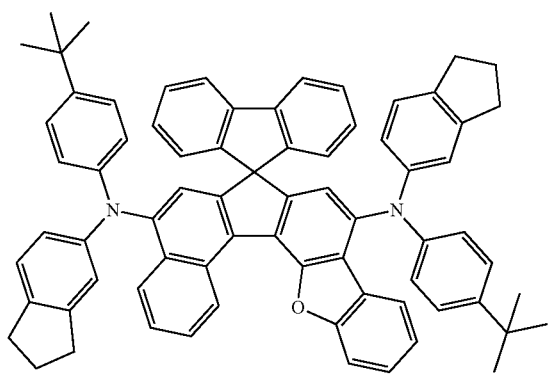
<Chemical Formula 169>
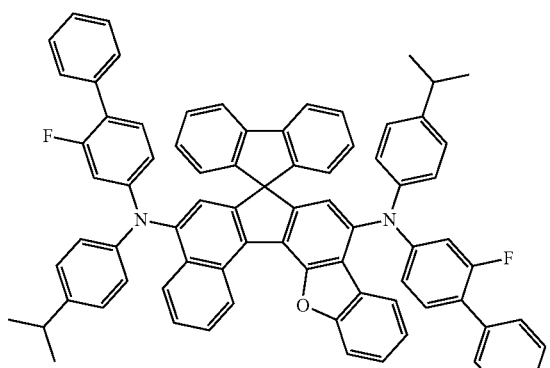
<Chemical Formula 170>
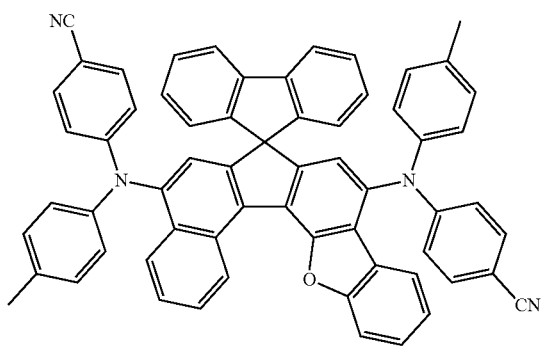
<Chemical Formula 171>
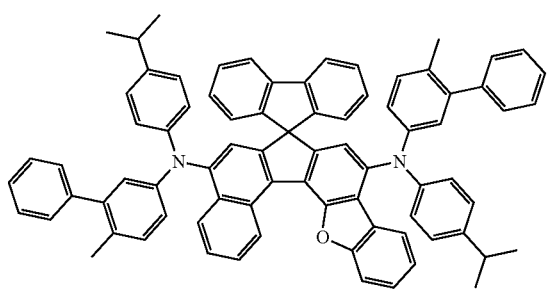
<Chemical Formula 172>
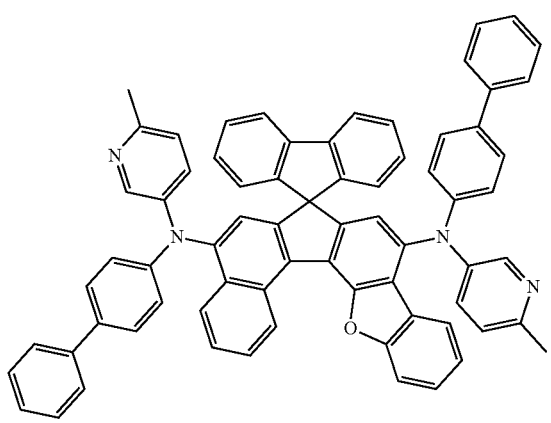
<Chemical Formula 173>
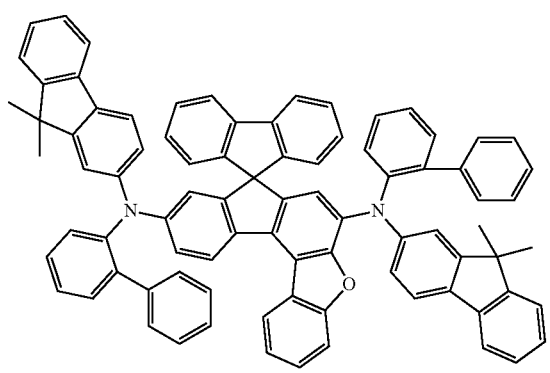

-continued
<Chemical Formula 174>
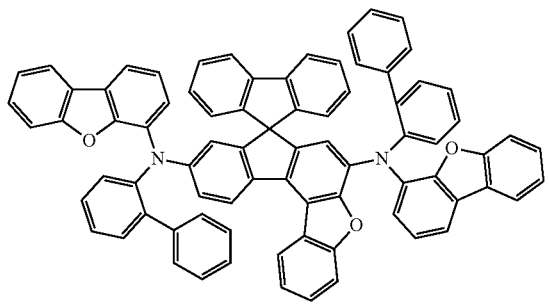
<Chemical Formula 175>
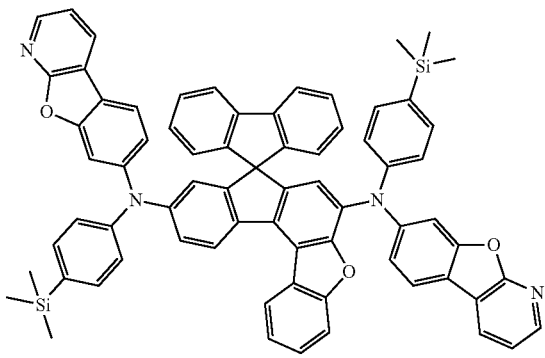
<Chemical Formula 176>
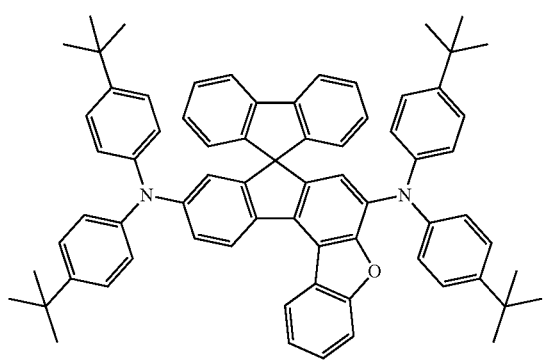
<Chemical Formula 177>
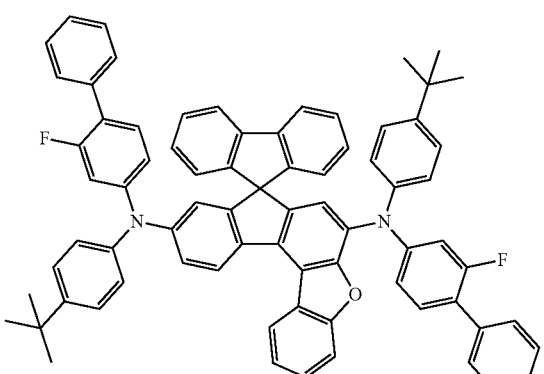
<Chemical Formula 178>
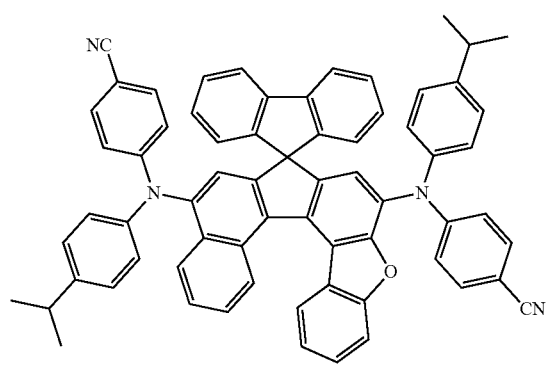
<Chemical Formula 179>
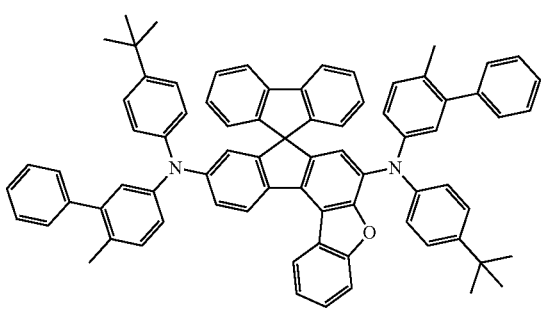
<Chemical Formula 180>
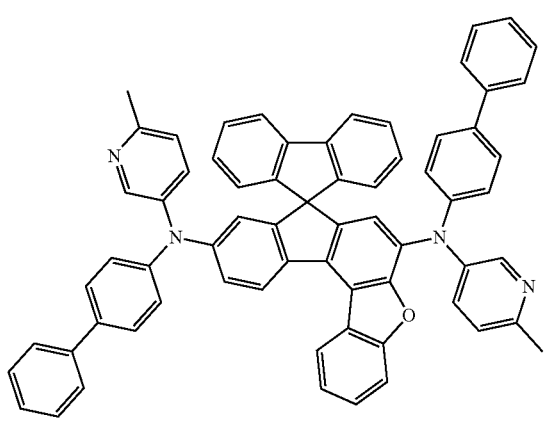
<Chemical Formula 181>
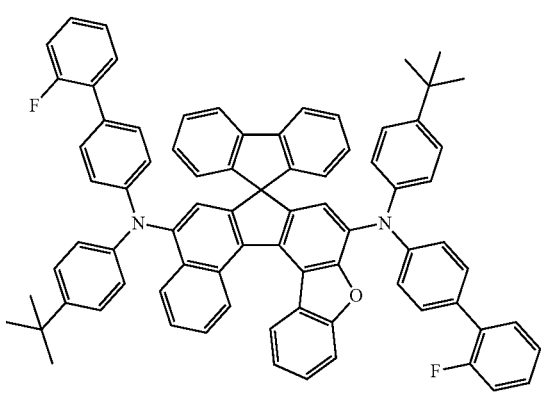

-continued
<Chemical Formula 182>
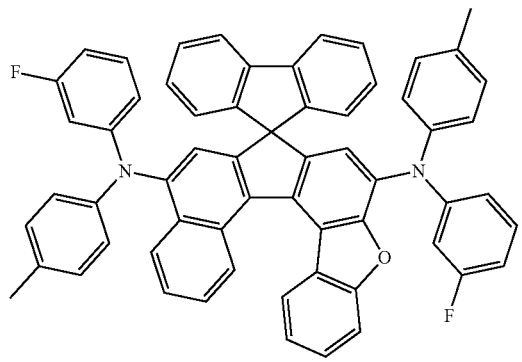
<Chemical Formula 183>
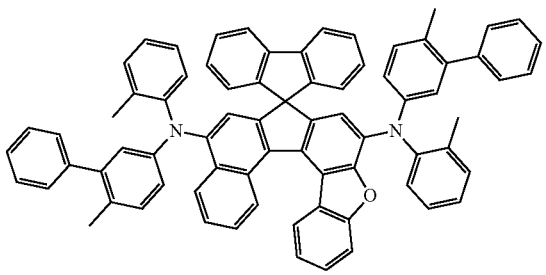
<Chemical Formula 184>
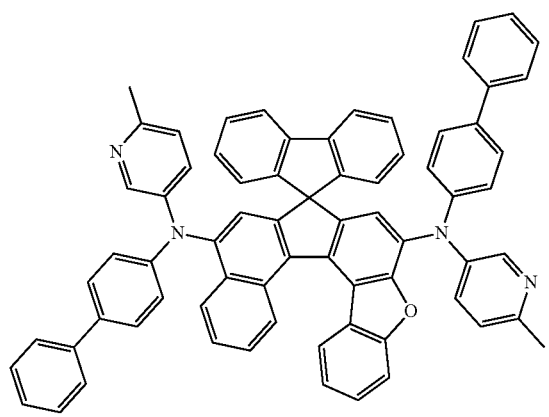
<Chemical Formula 185>
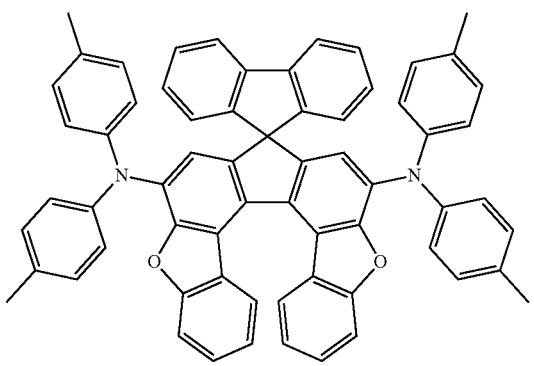
<Chemical Formula 186>
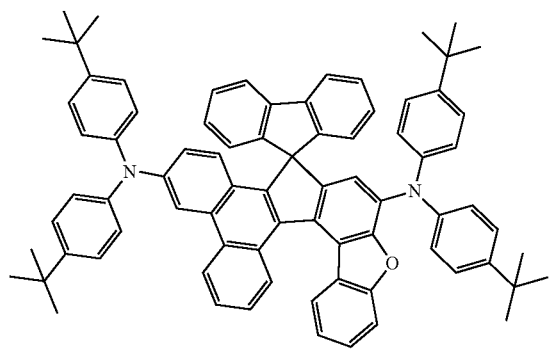
<Chemical Formula 187>
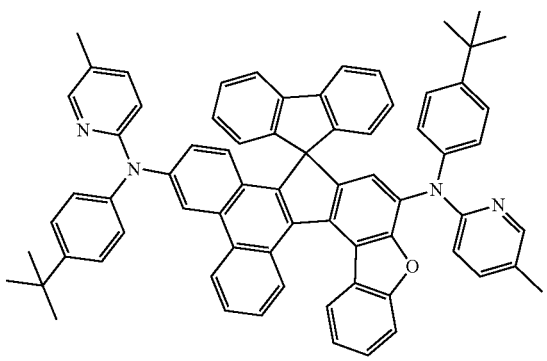
<Chemical Formula 188>
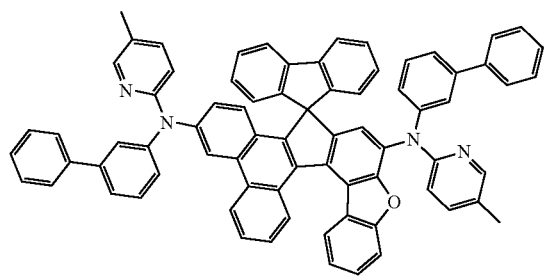
<Chemical Formula 189>
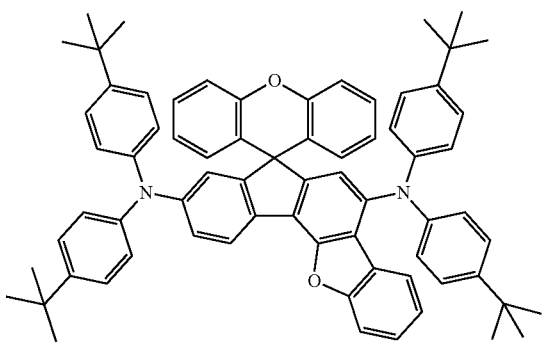

-continued
<Chemical Formula 190>
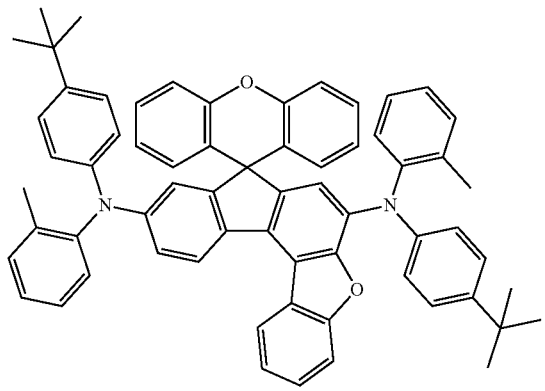
<Chemical Formula 191>
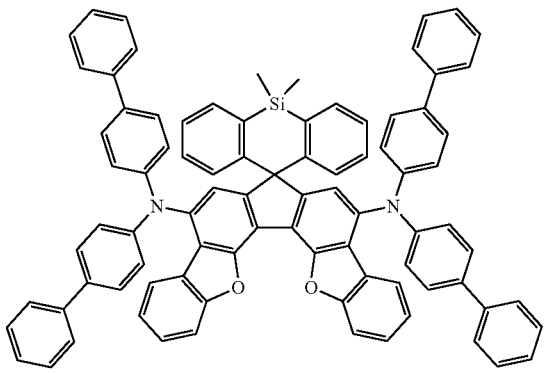
<Chemical Formula 192>
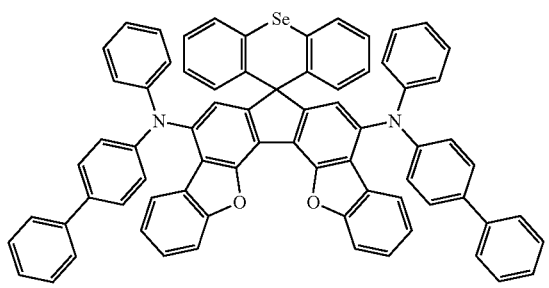
<Chemical Formula 193>
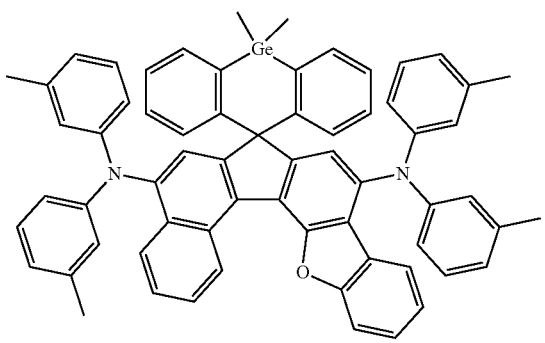
<Chemical Formula 194>
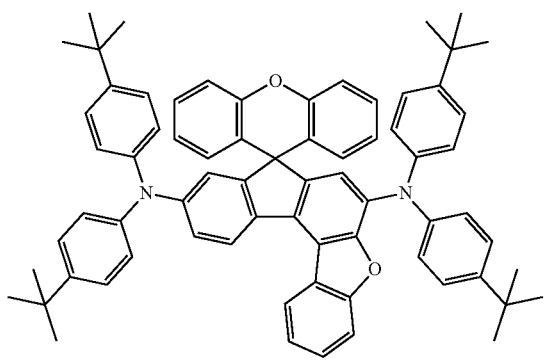
<Chemical Formula 195>
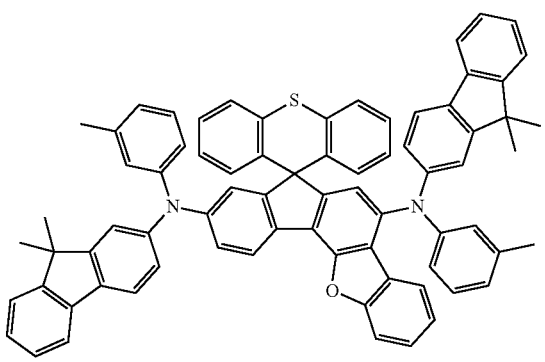

<Chemical Formula 196>
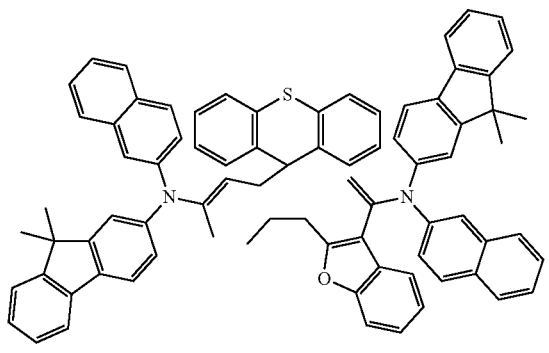
<Chemical Formula 197>
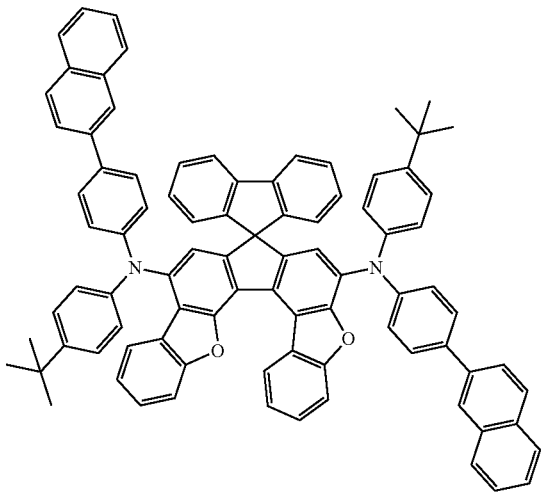
<Chemical Formula 198>
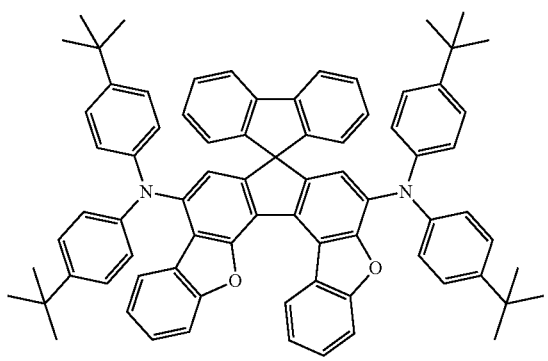
<Chemical Formula 199>
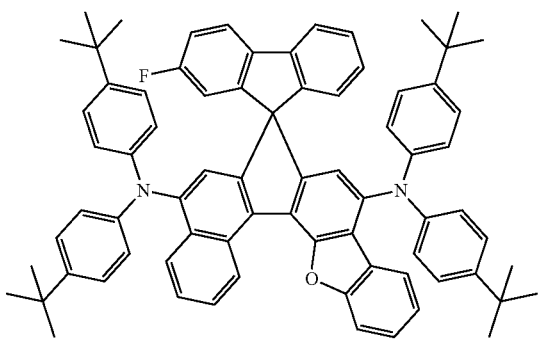
<Chemical Formula 200>
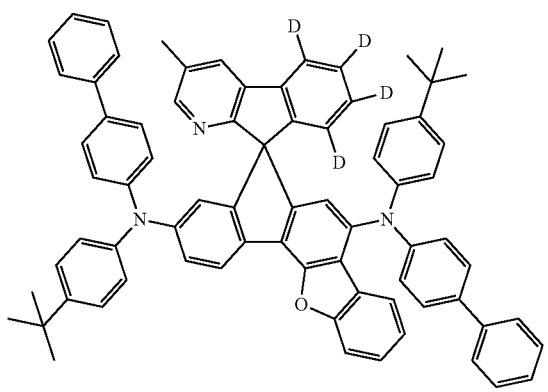
<Chemical Formula 201>
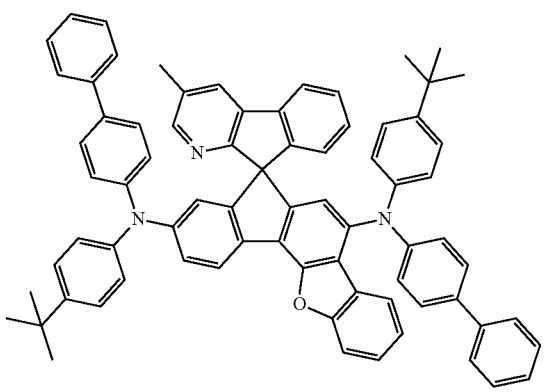

<Chemical Formula 202>
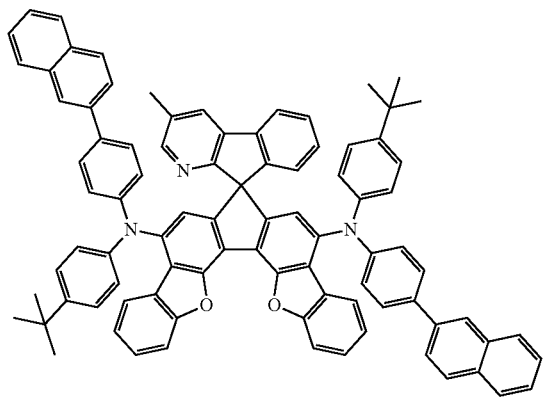
<Chemical Formula 203>
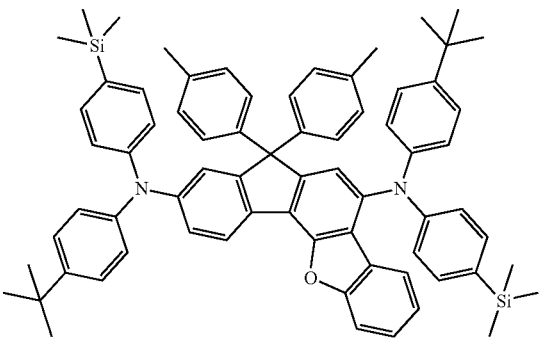
<Chemical Formula 204>
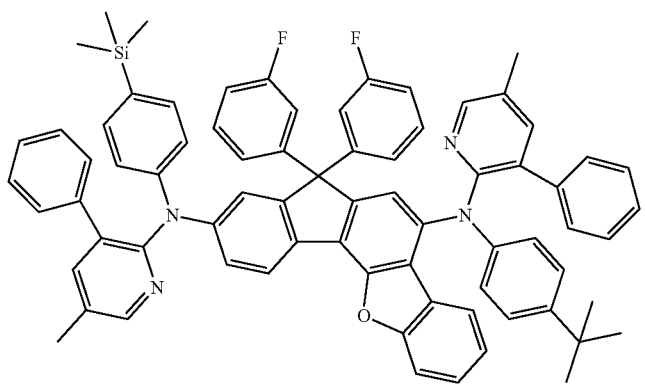
<Chemical Formula 205>
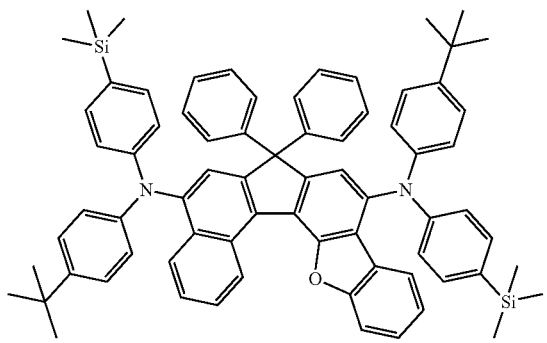
<Chemical Formula 206>
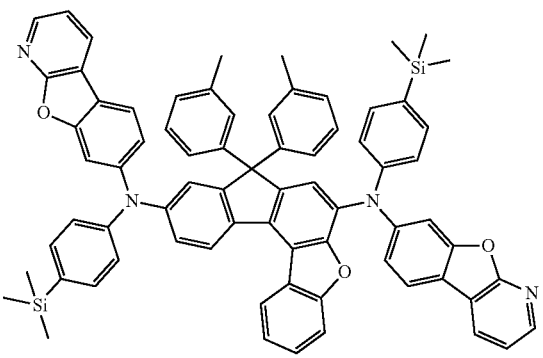
<Chemical Formula 207>
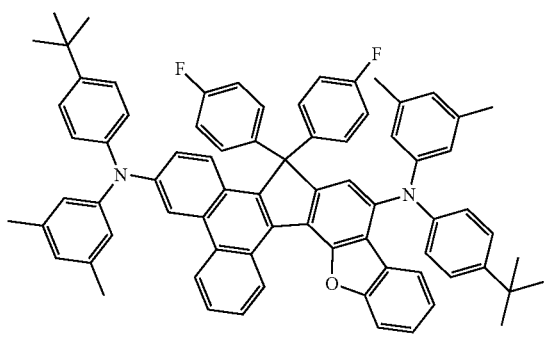
<Chemical Formula 208>
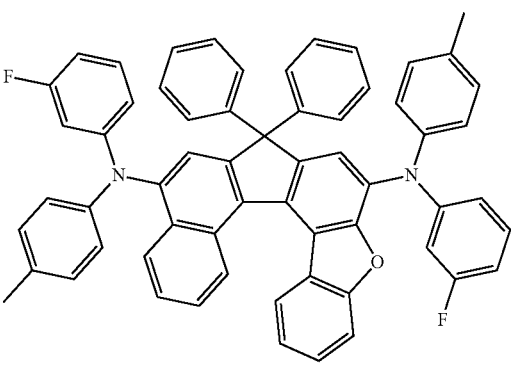

<Chemical Formula 209>
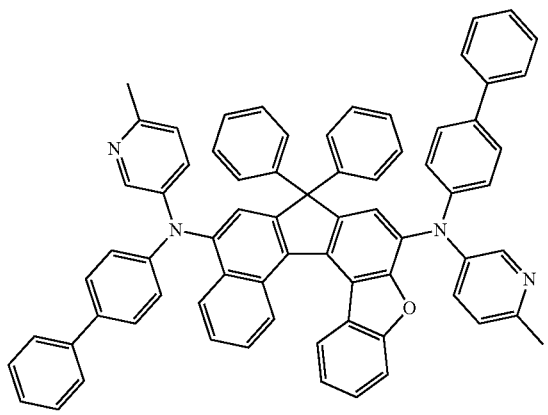
<Chemical Formula 210>
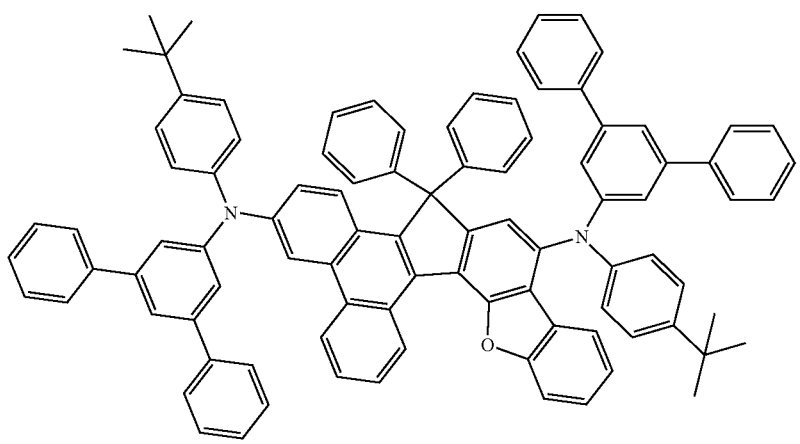
<Chemical Formula 211>
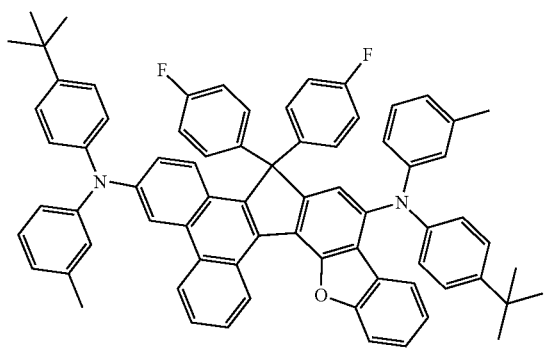
<Chemical Formula 212>
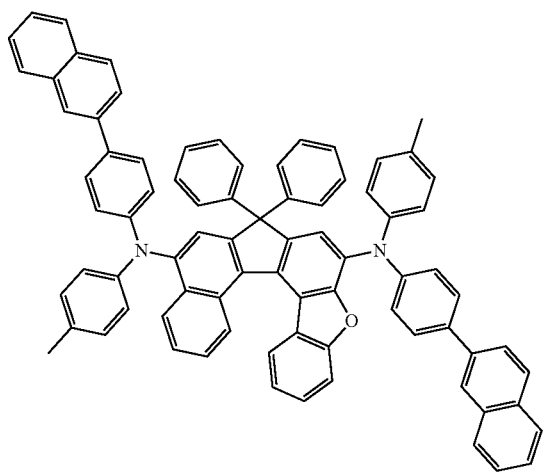

<Chemical Formula 213>
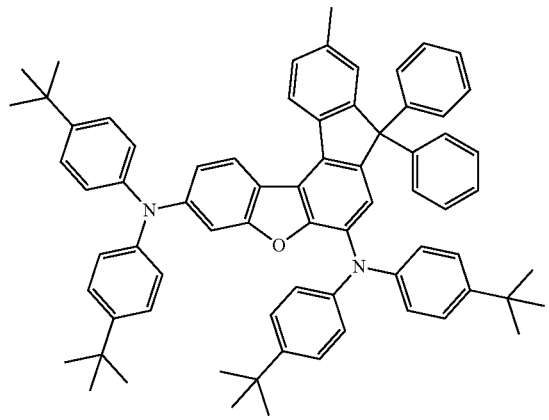
<Chemical Formula 214>
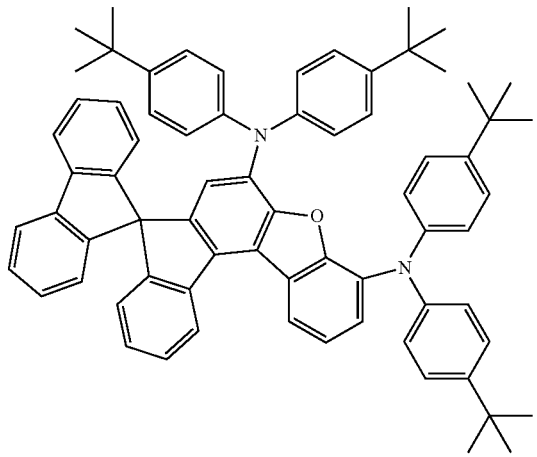
[Chemical Formula 215]
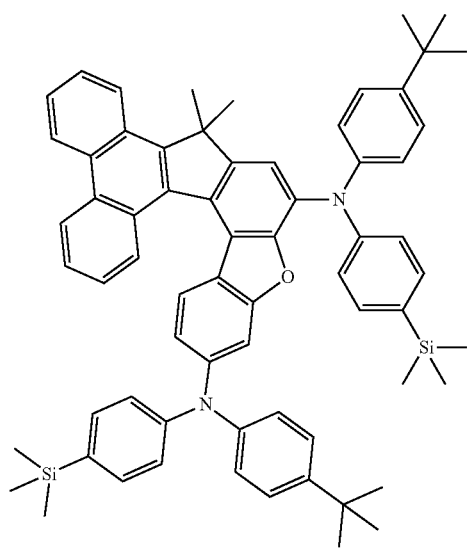
[Chemical Formula 216]
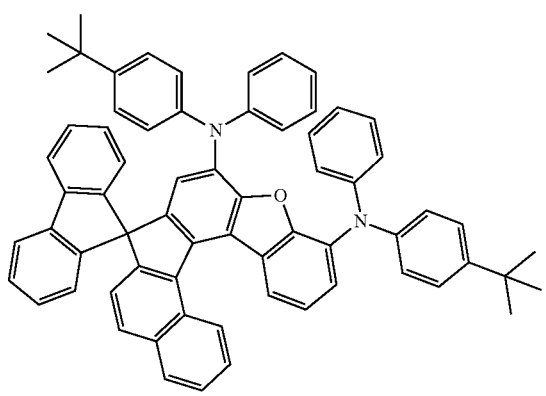
[Chemical Formula 217]
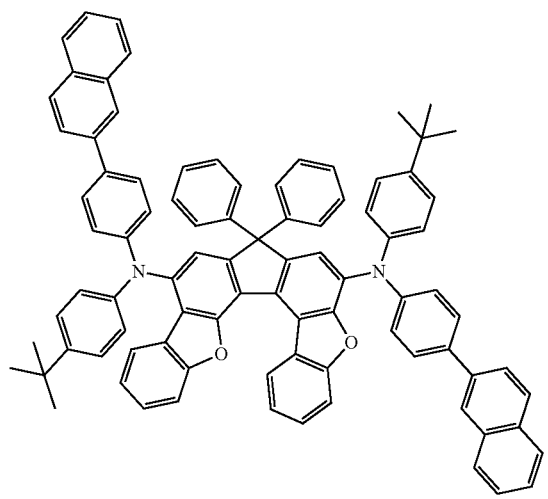
[Chemical Formula 218]
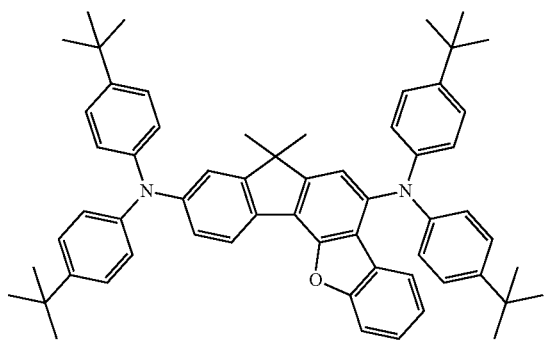

-continued
[Chemical Formula 219]
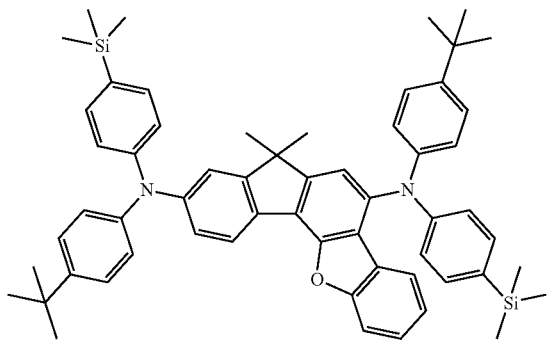
[Chemical Formula 220]
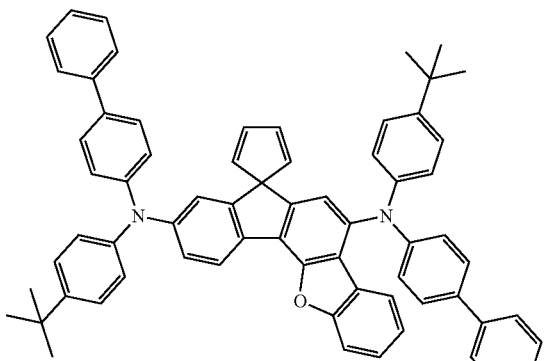
<Chemical Formula 221>
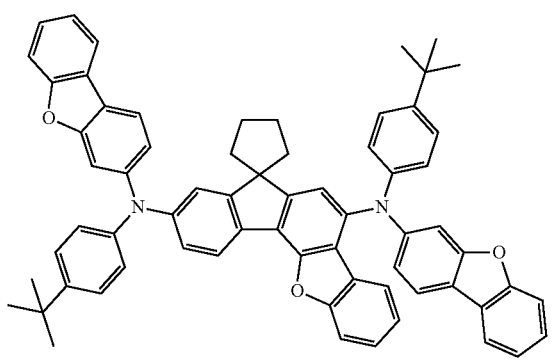
<Chemical Formula 222>
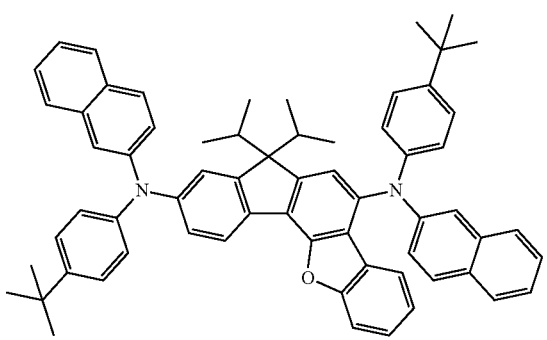
<Chemical Formula 223>
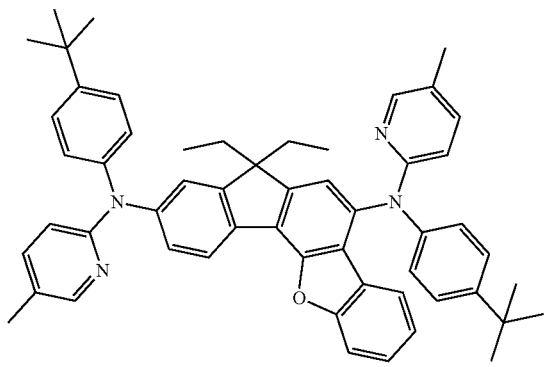
<Chemical Formula 224>
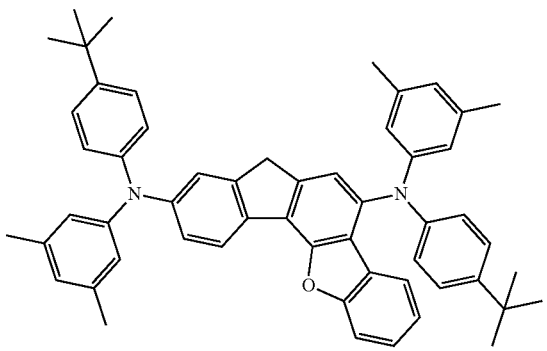
<Chemical Formula 225>
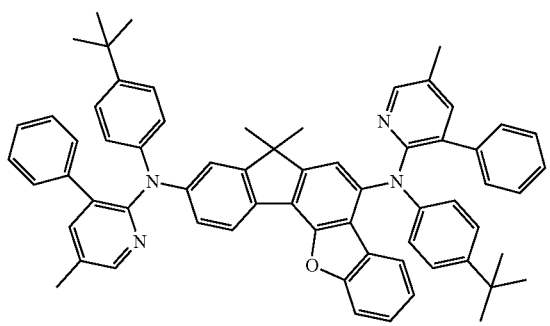

<Chemical Formula 226>
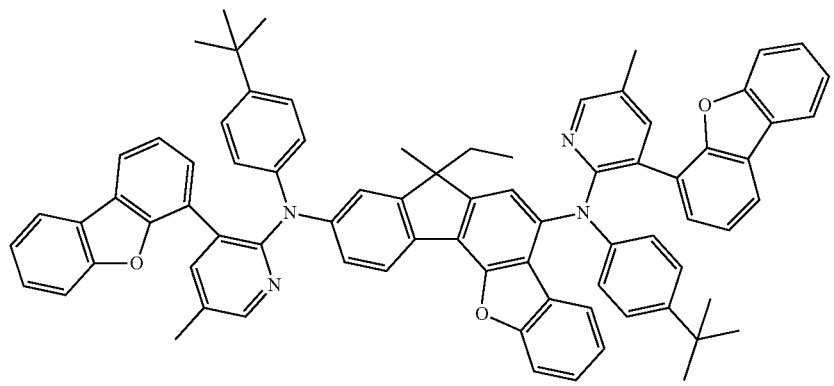
<Chemical Formula 227>
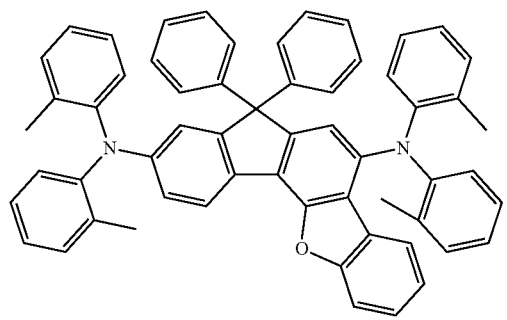
<Chemical Formula 228>
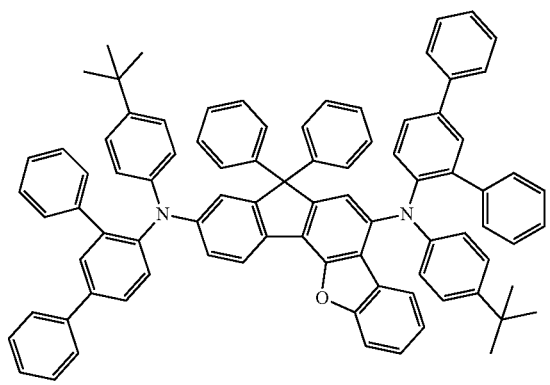
<Chemical Formula 229>
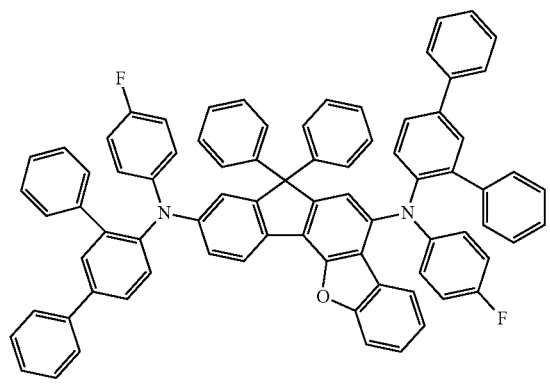
<Chemical Formula 230>
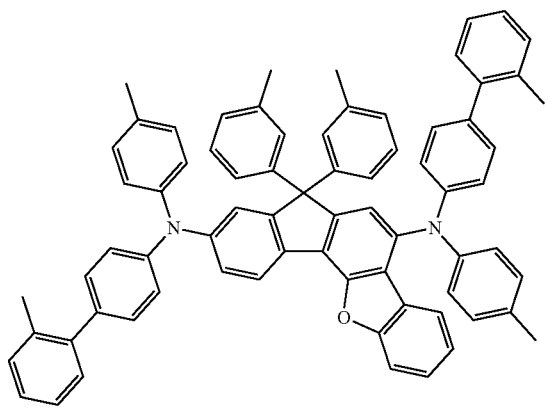

-continued
<Chemical Formula 231>
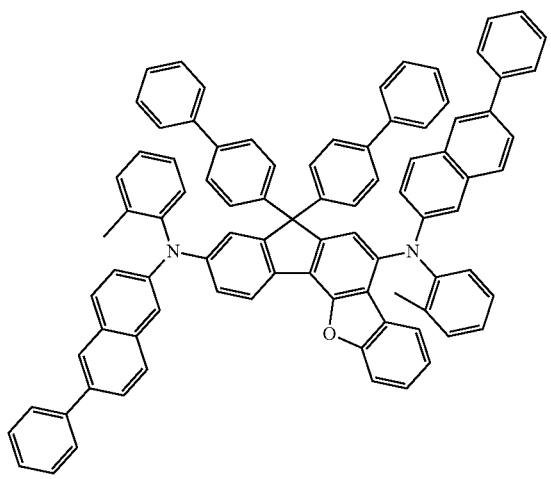
<Chemical Formula 232>
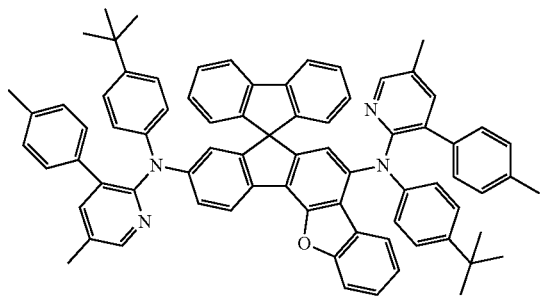
<Chemical Formula 233>
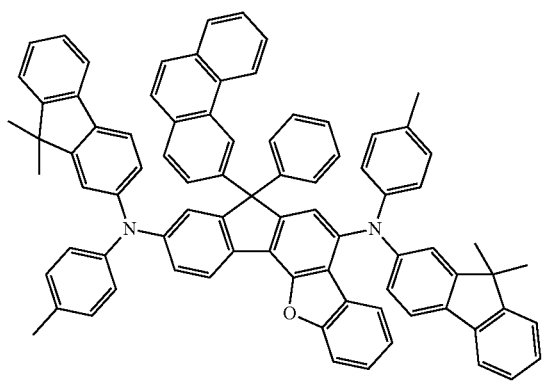
<Chemical Formula 234>
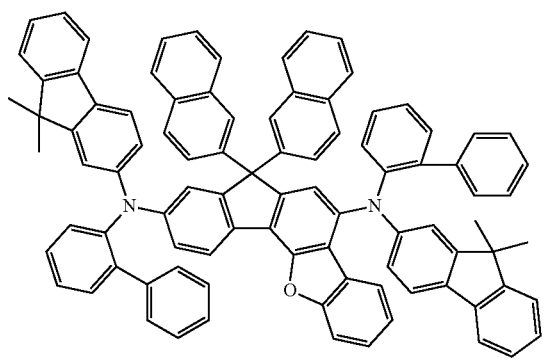
<Chemical Formula 235>
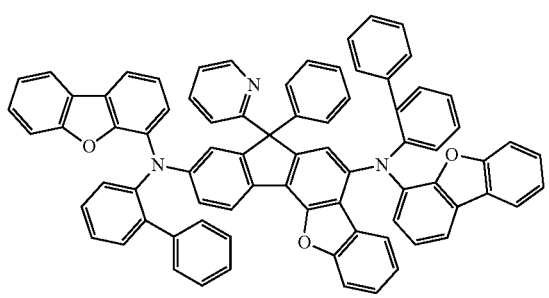
<Chemical Formula 236>
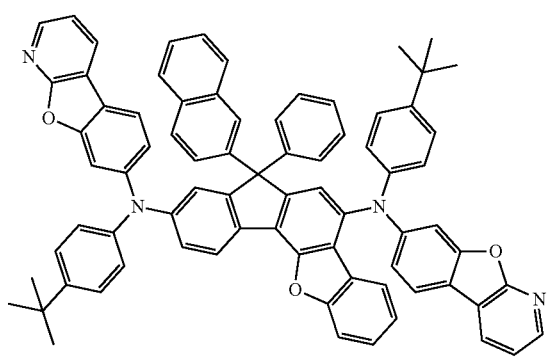

<Chemical Formula 237>
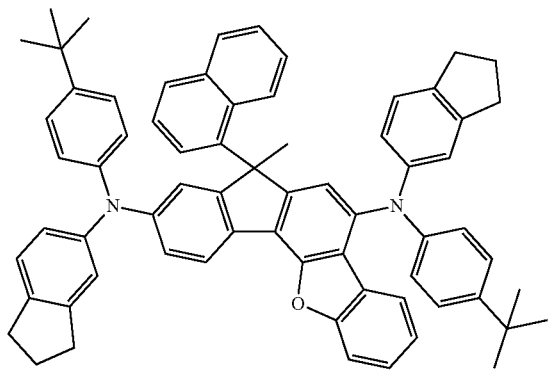
<Chemical Formula 238>
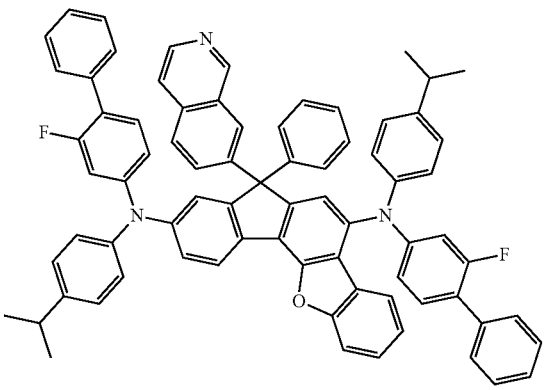
<Chemical Formula 239>
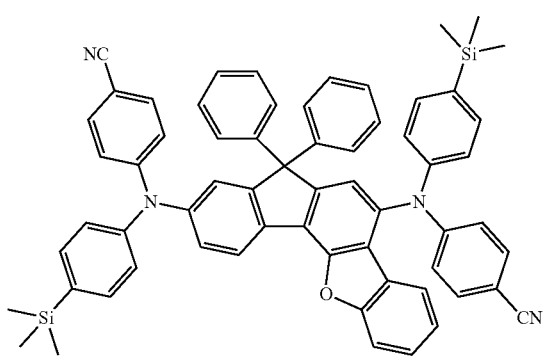
<Chemical Formula 240>
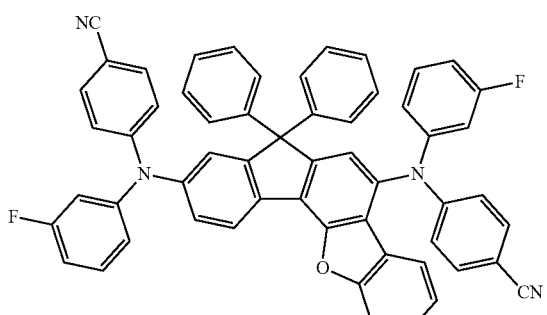
<Chemical Formula 241>
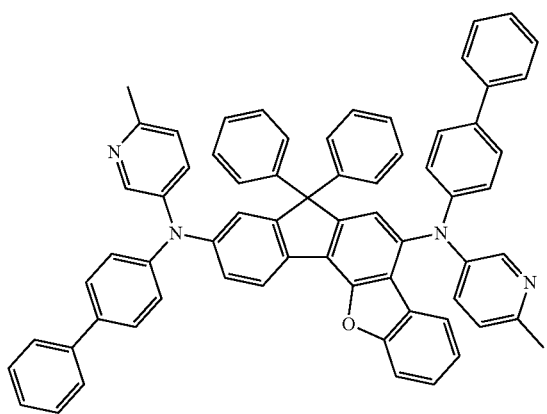
<Chemical Formula 242>
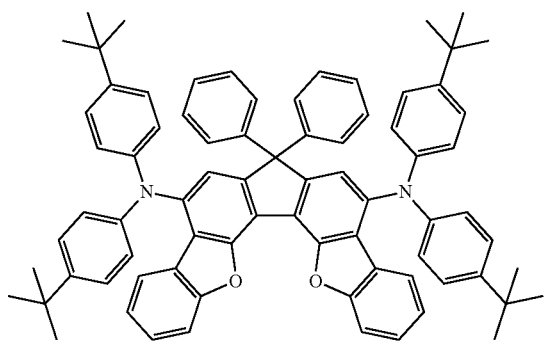

-continued
<Chemical Formula 243>
<Chemical Formula 244>
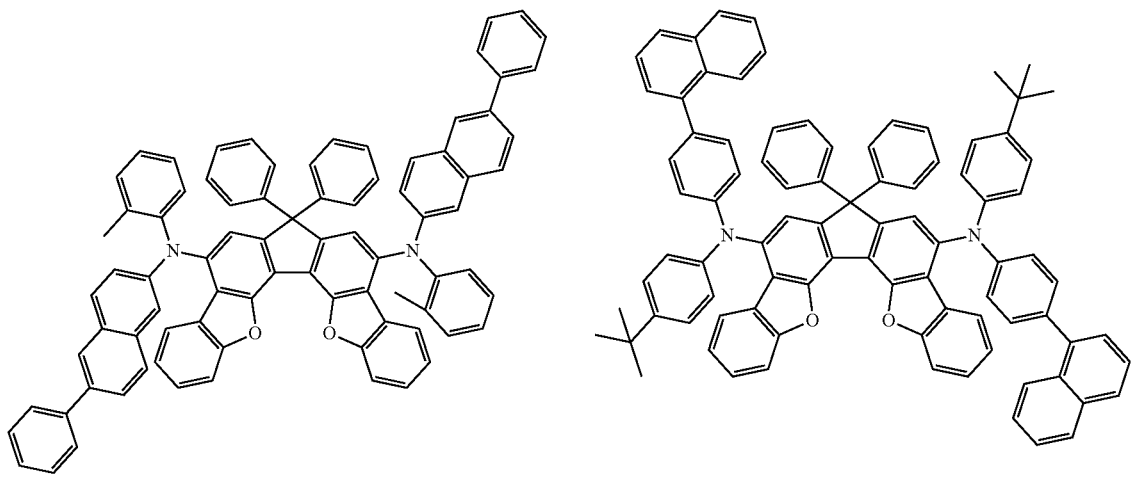
<Chemical Formula 245>
<Chemical Formula 246>
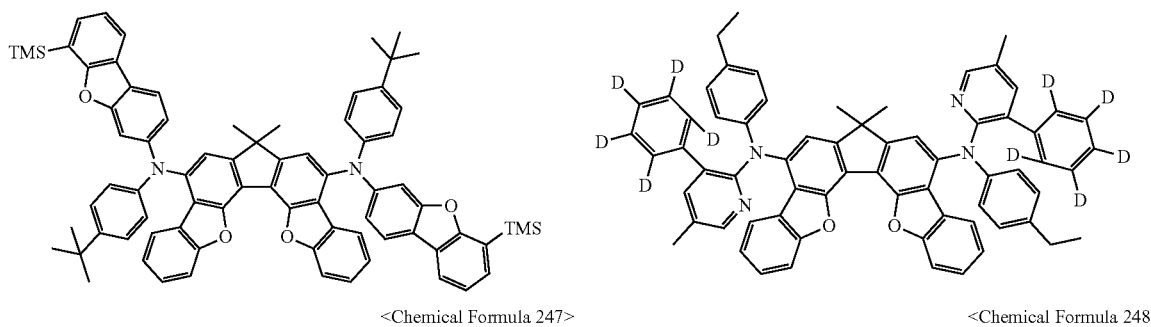
<Chemical Formula 247>
<Chemical Formula 248>
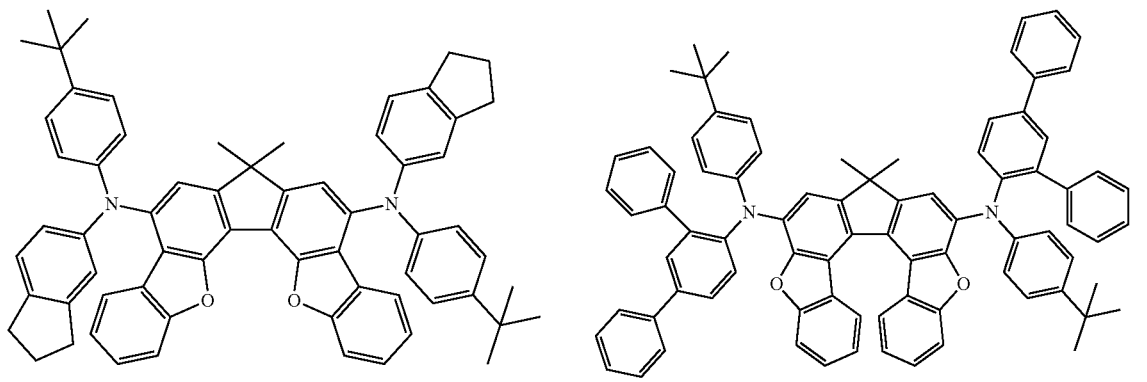
<Chemical Formula 249>
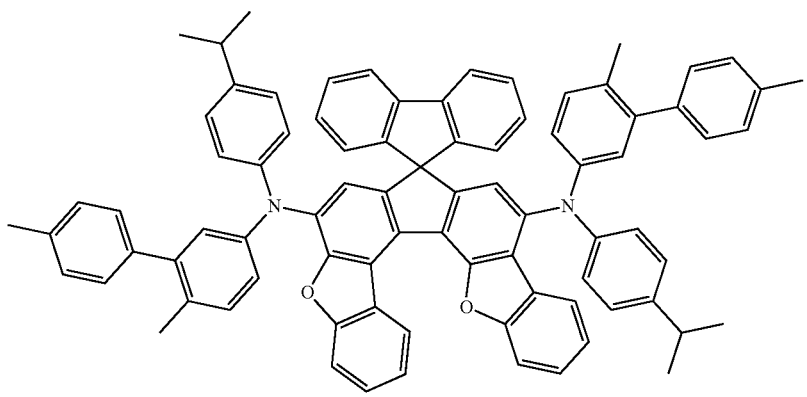

<Chemical Formula 250>
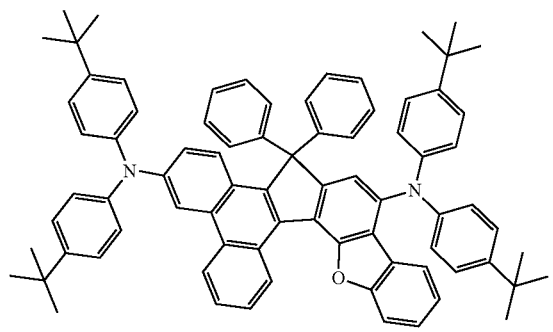
<Chemical Formula 251>
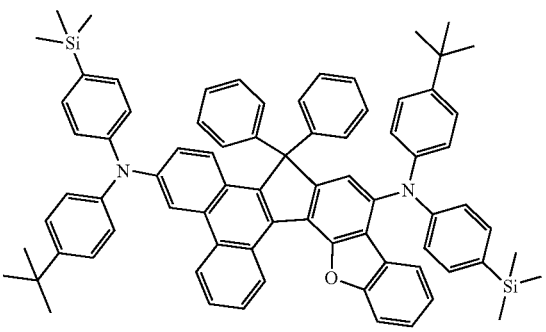
<Chemical Formula 252>
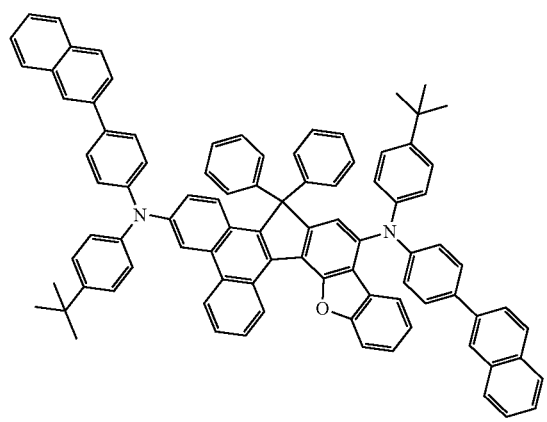
<Chemical Formula 253>
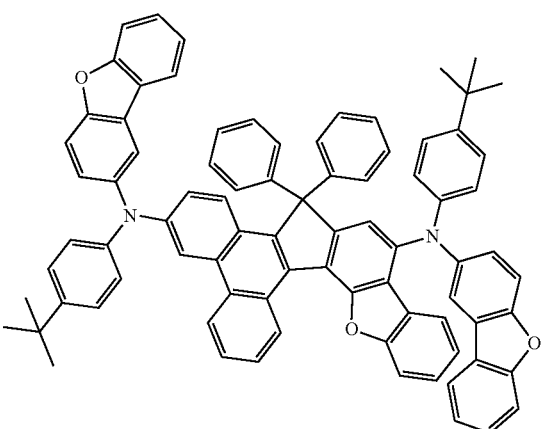
<Chemical Formula 254>
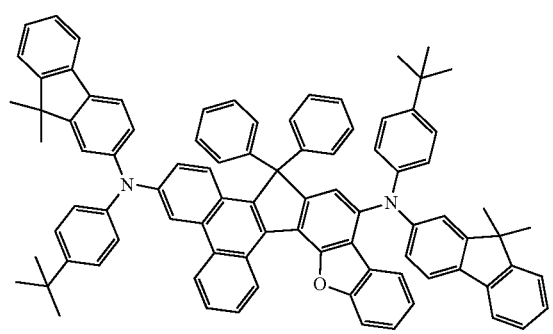
<Chemical Formula 255>
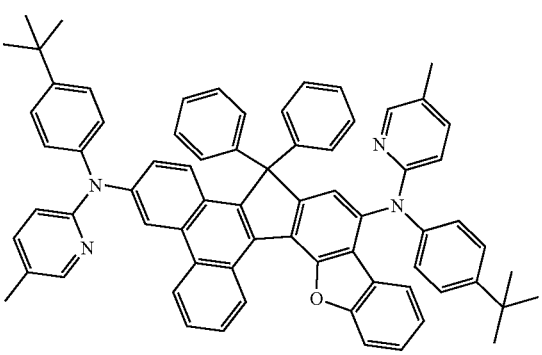
<Chemical Formula 256>
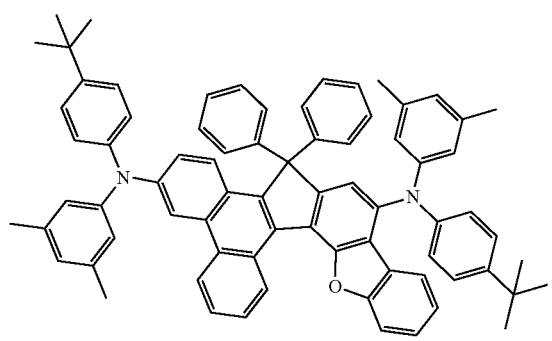
<Chemical Formula 257>
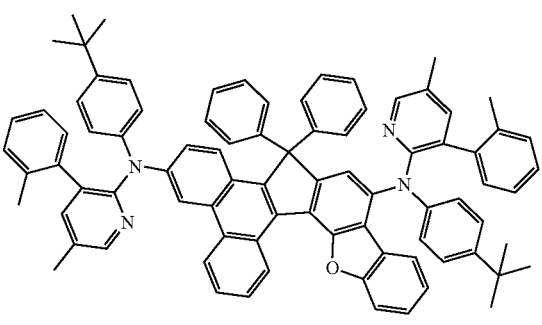

-continued
<Chemical Formula 258>
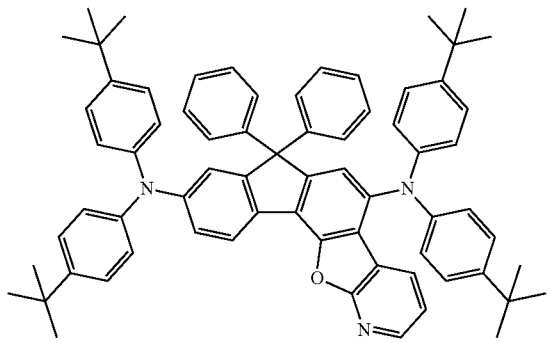
<Chemical Formula 259>
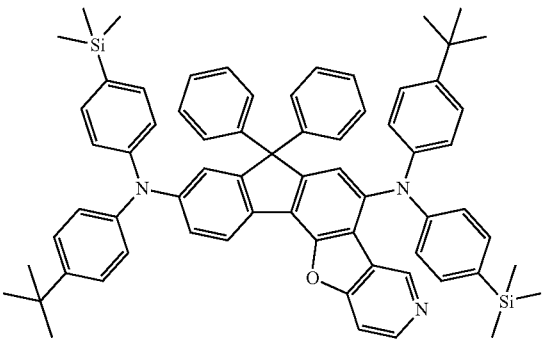
<Chemical Formula 260>
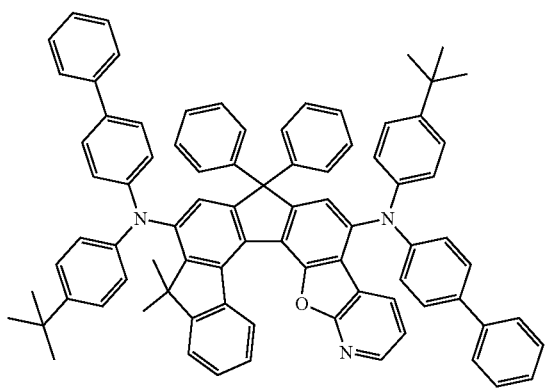
<Chemical Formula 261>
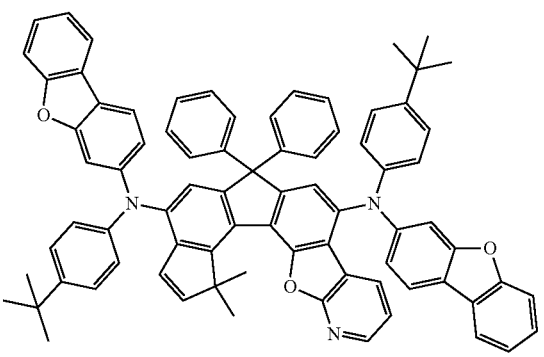
<Chemical Formula 262>
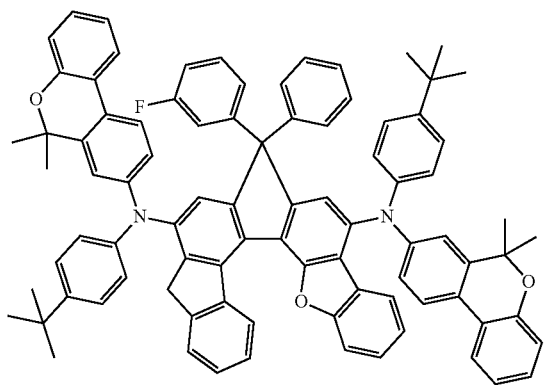
<Chemical Formula 263>
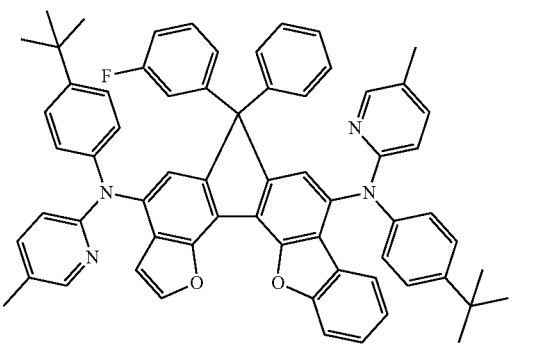
<Chemical Formula 264>
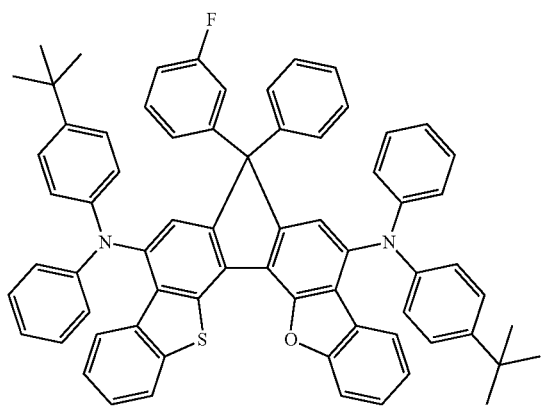
<Chemical Formula 265>
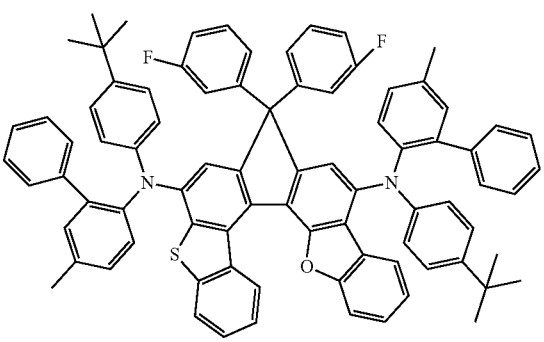

<Chemical Formula 266>
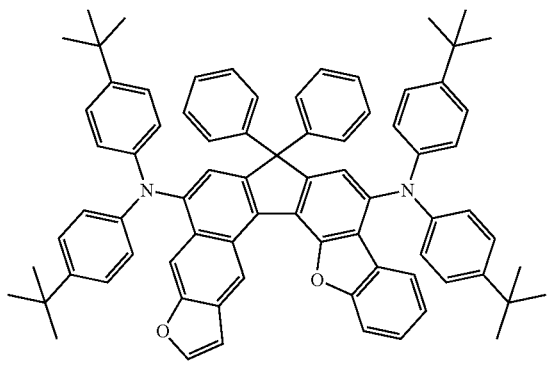
<Chemical Formula 268>
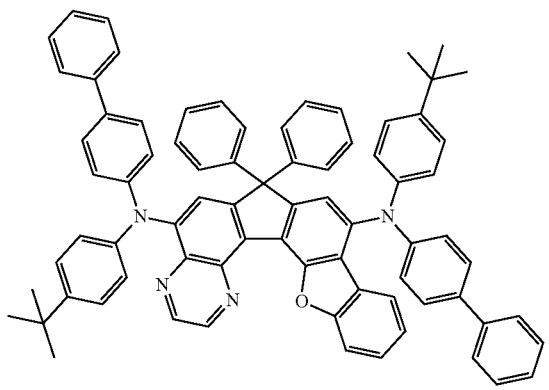
<Chemical Formula 270>
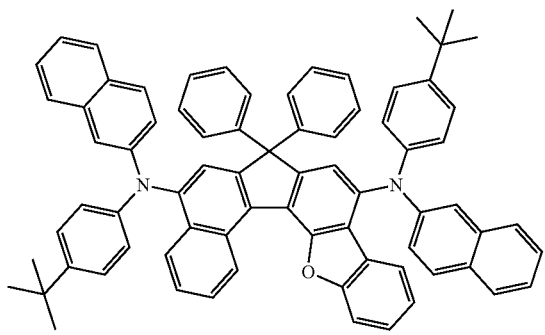
<Chemical Formula 272>
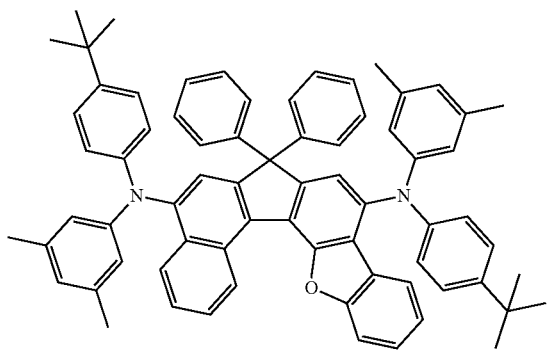
<Chemical Formula 267>
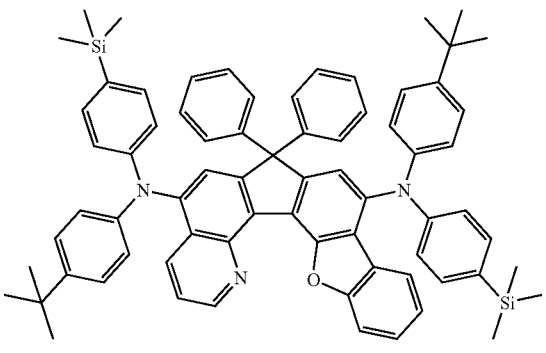
<Chemical Formula 269>
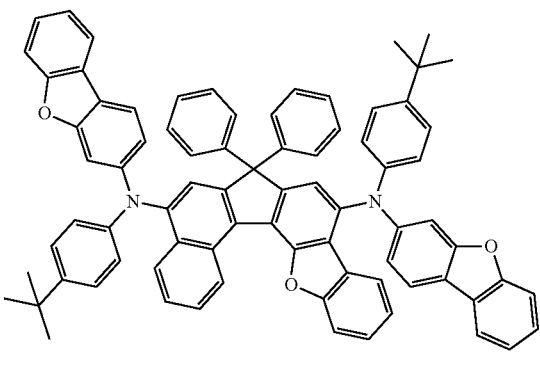
<Chemical Formula 271>
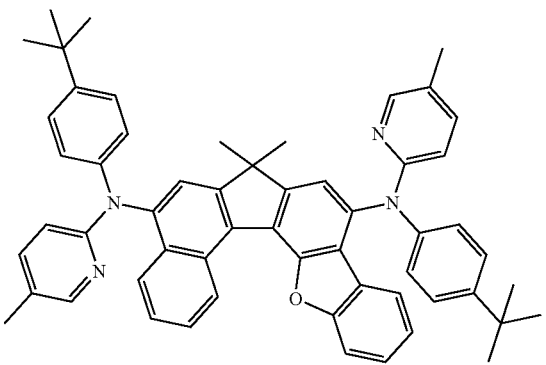
<Chemical Formula 273>
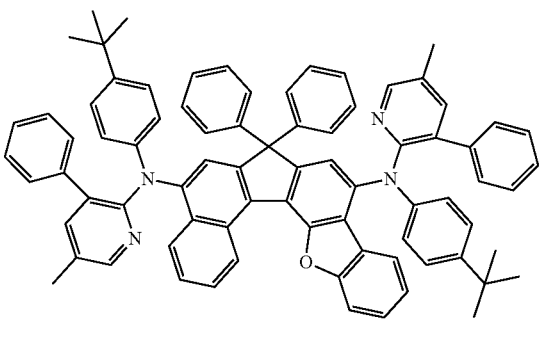

<Chemical Formula 274>
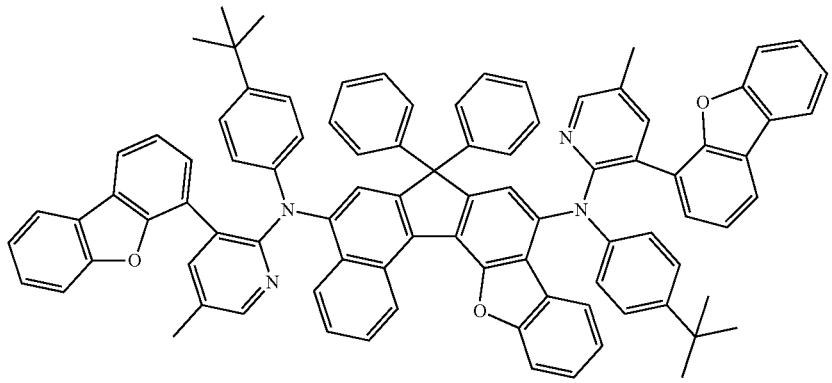
<Chemical Formula 275>
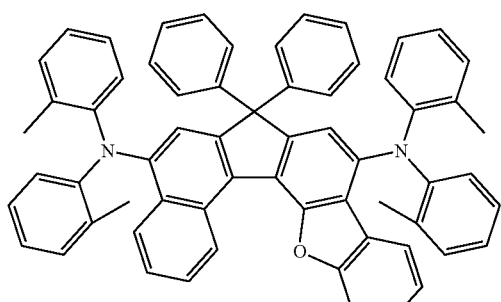
<Chemical Formula 276>
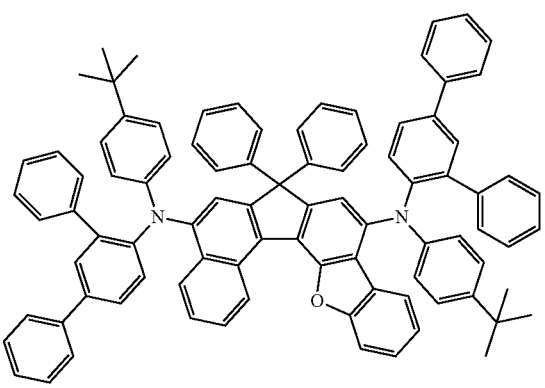
<Chemical Formula 277>
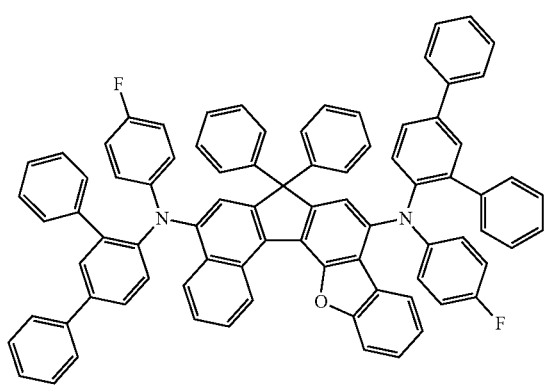
<Chemical Formula 278>
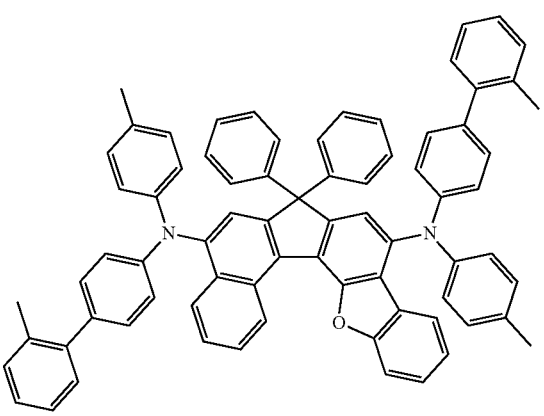
<Chemical Formula 279>
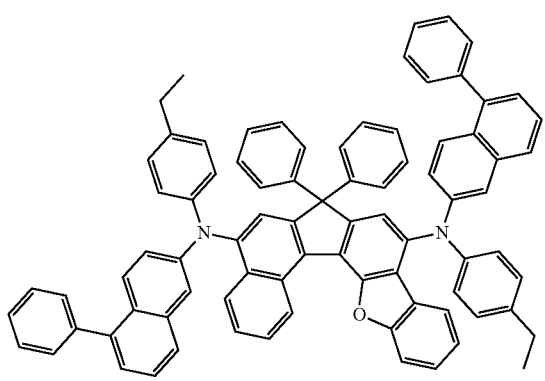
<Chemical Formula 280>
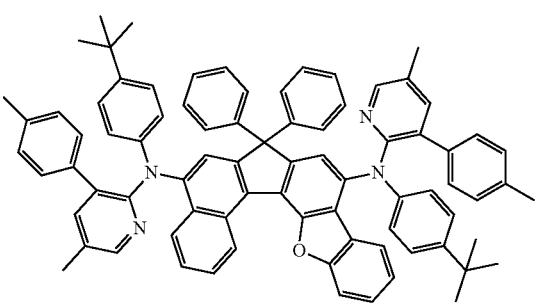

<Chemical Formula 281>
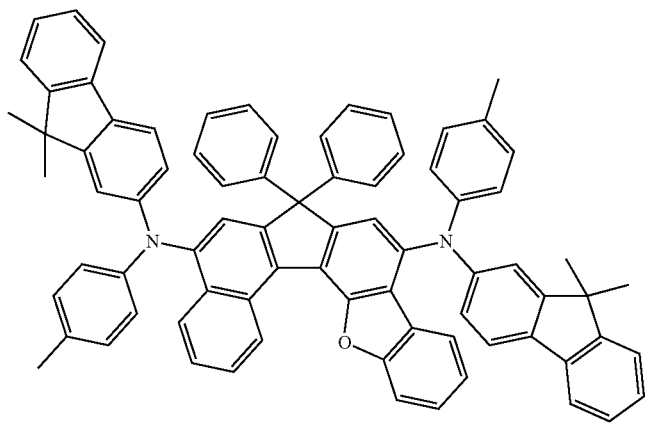
<Chemical Formula 282>
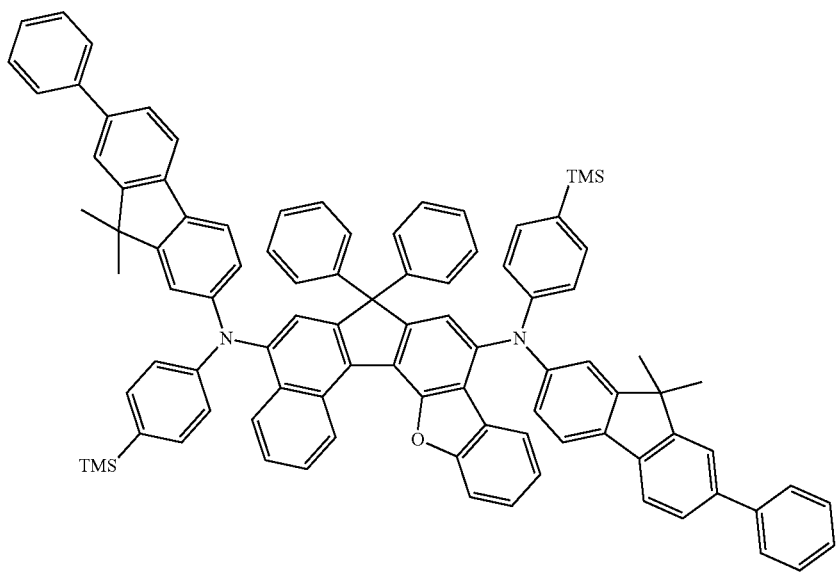
<Chemical Formula 283>
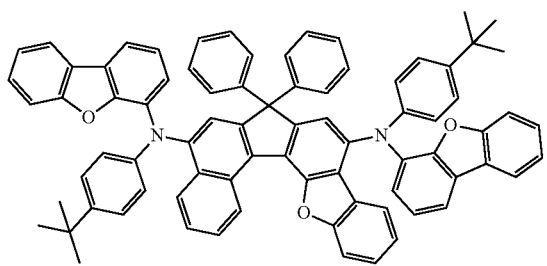
<Chemical Formula 284>
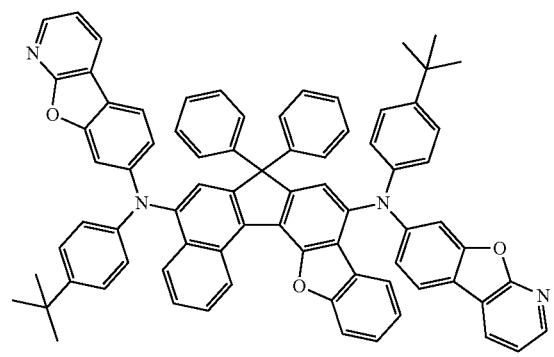

<Chemical Formula 285>
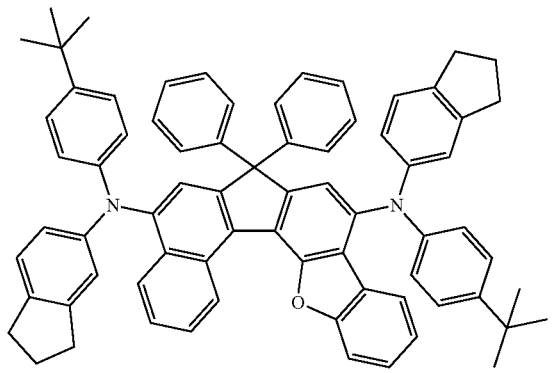
<Chemical Formula 286>
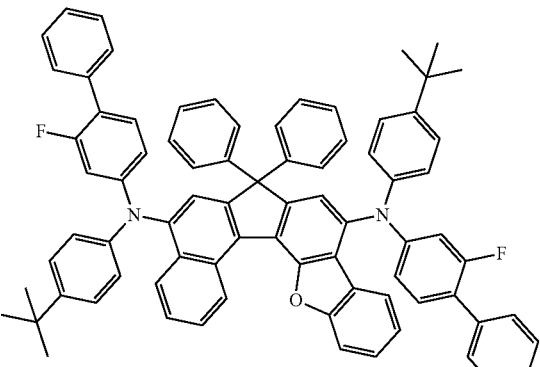
<Chemical Formula 287>
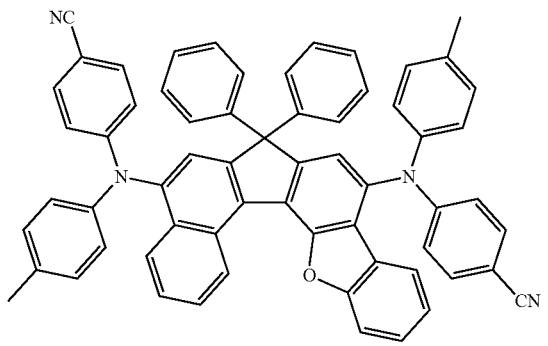
<Chemical Formula 288>
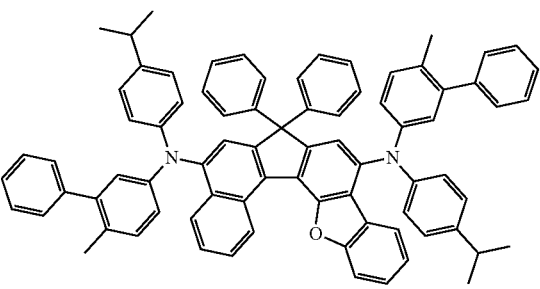
<Chemical Formula 289>
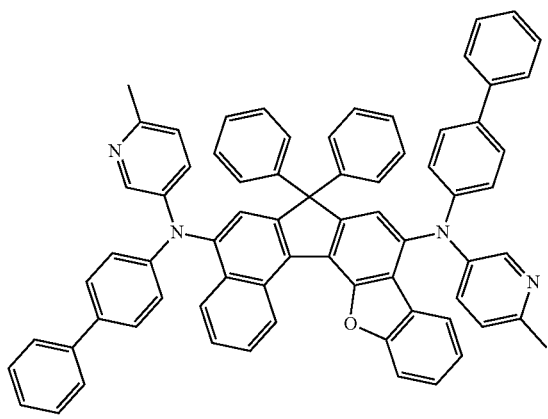
<Chemical Formula 290>
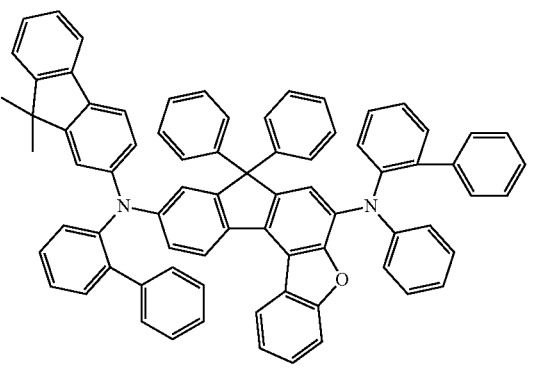
<Chemical Formula 291>
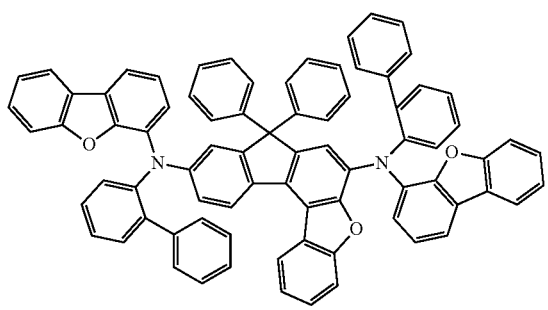
<Chemical Formula 292>
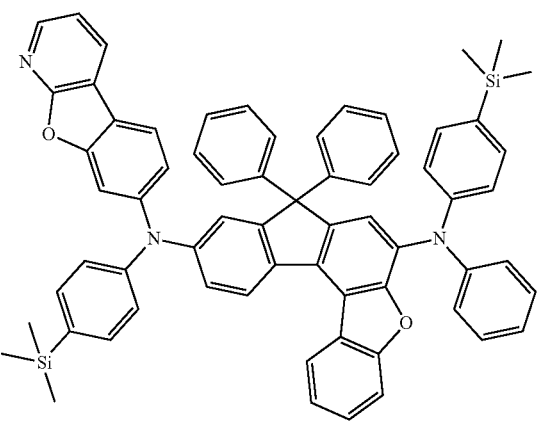

-continued
<Chemical Formula 293>
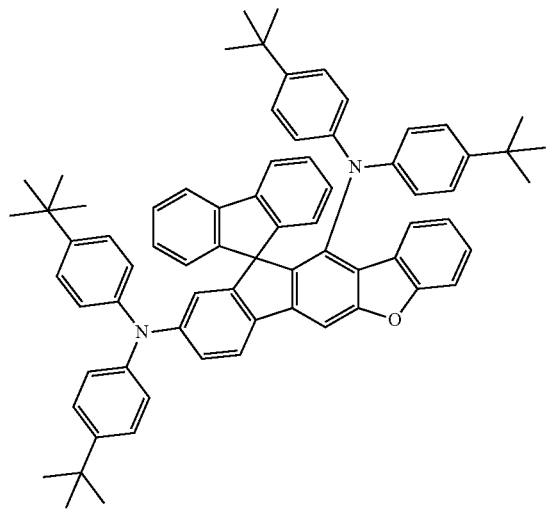
<Chemical Formula 294>
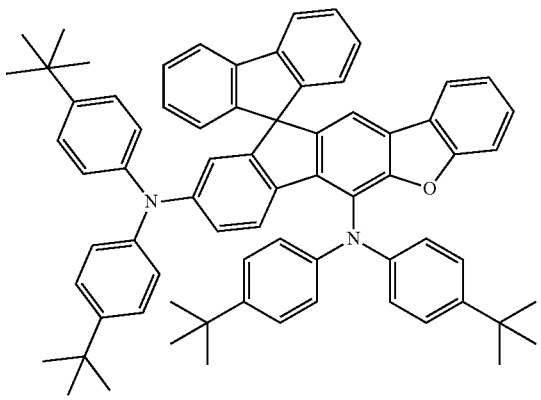
<Chemical Formula 295>
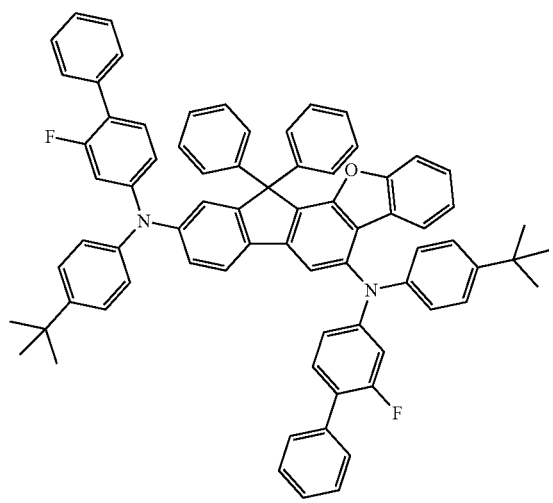
<Chemical Formula 296>
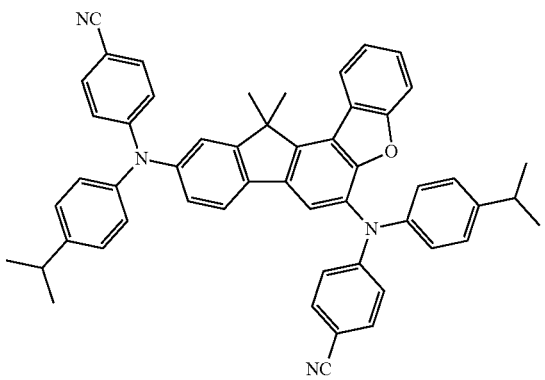
<Chemical Formula 297>
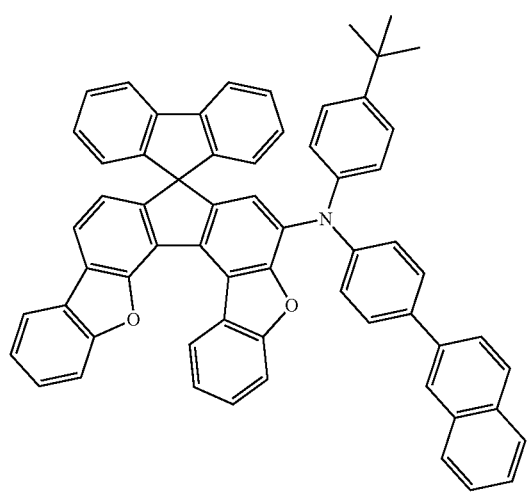
<Chemical Formula 298>
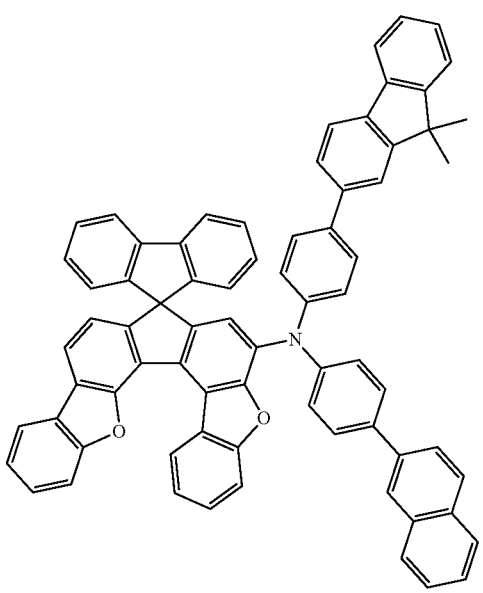

<Chemical Formula 299>
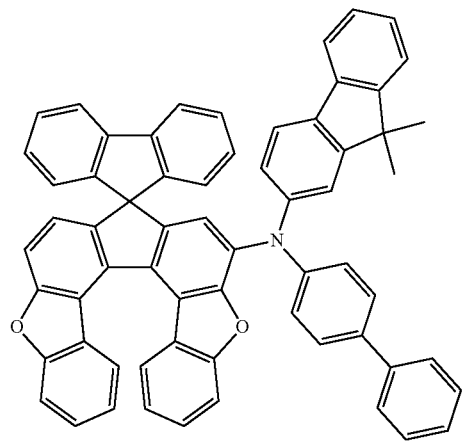
<Chemical Formula 300>
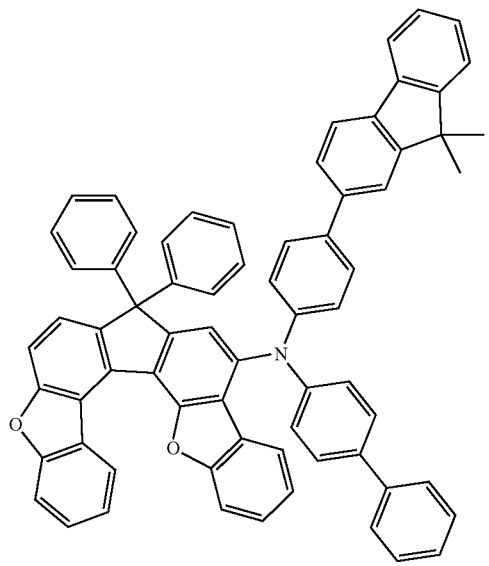
<Chemical Formula 301>
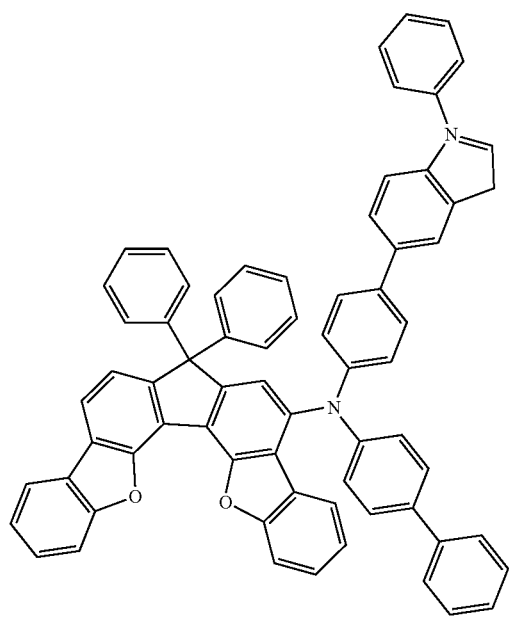
<Chemical Formula 302>
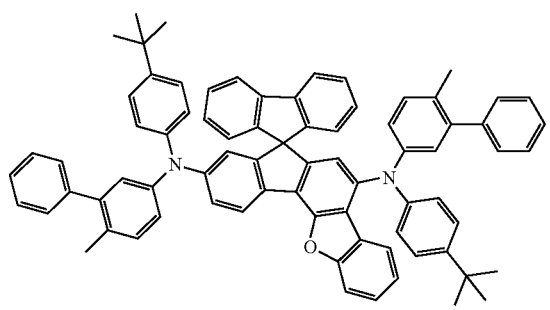

<Chemical Formula 303>
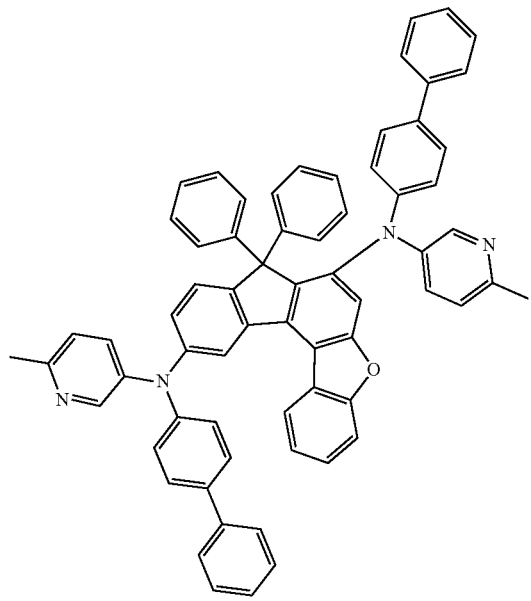
<Chemical Formula 304>
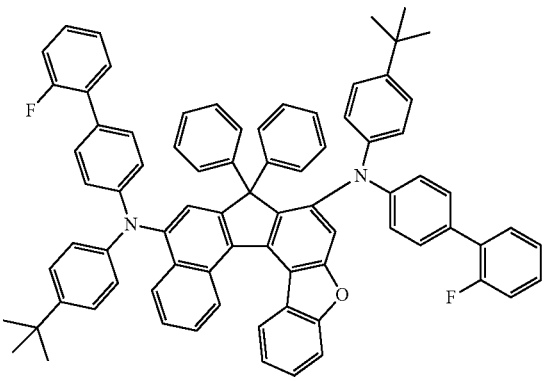
<Chemical Formula 305>
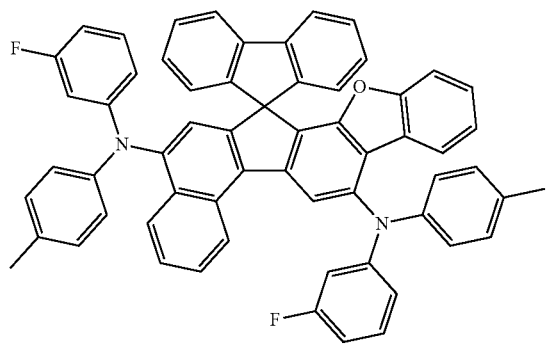
<Chemical Formula 306>
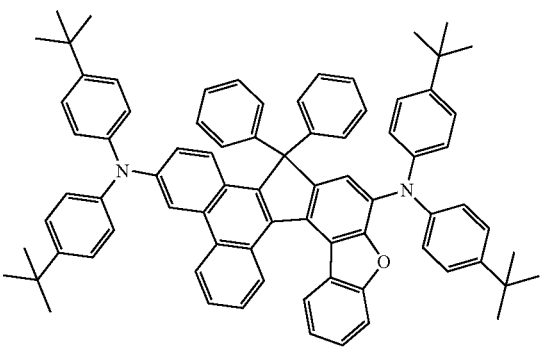
<Chemical Formula 307>
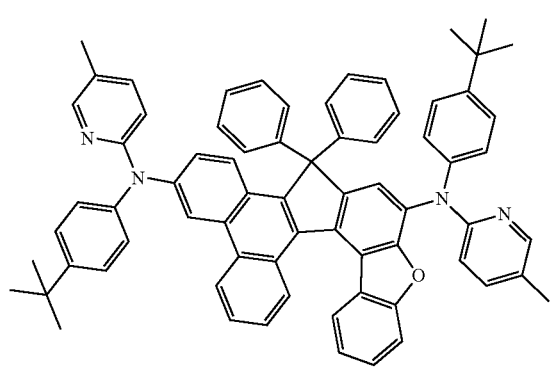

<Chemical Formula 308>
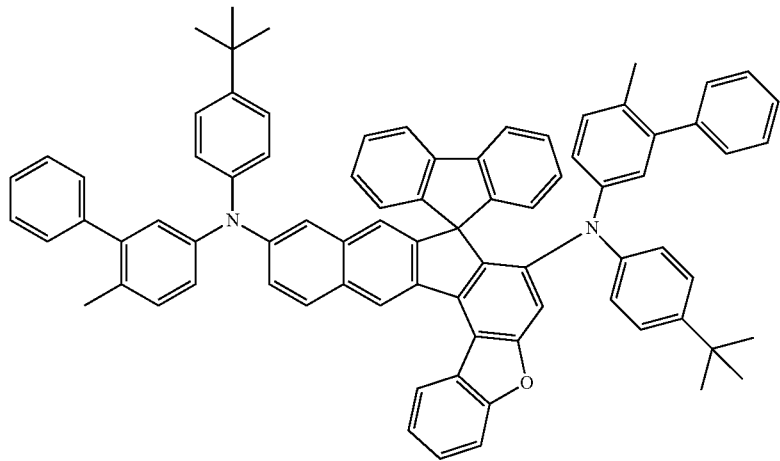
<Chemical Formula 309>
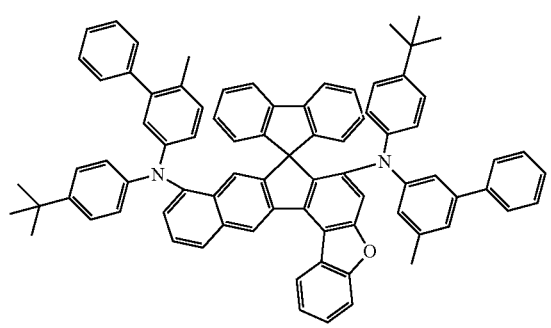
<Chemical Formula 310>
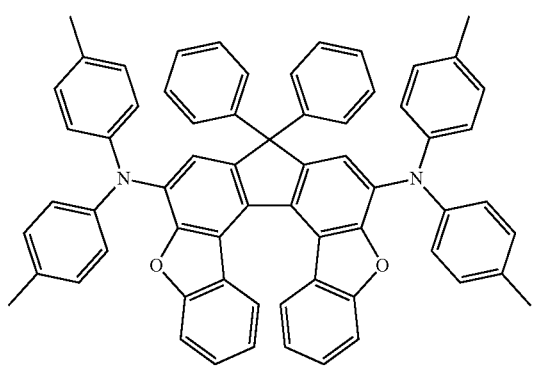
<Chemical Formula 311>
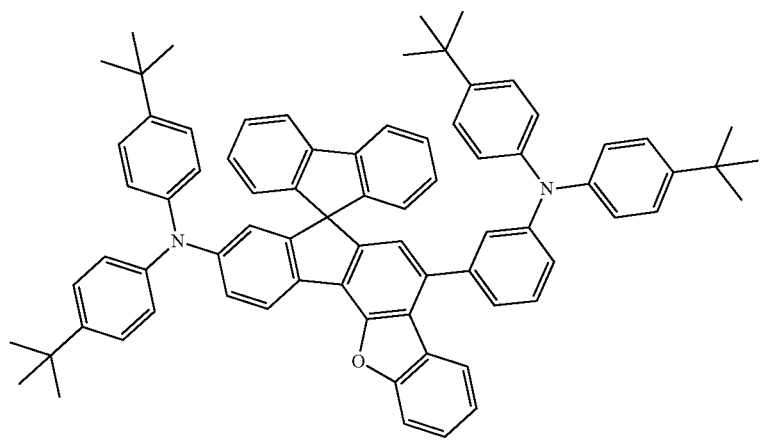

<Chemical Formula 312>
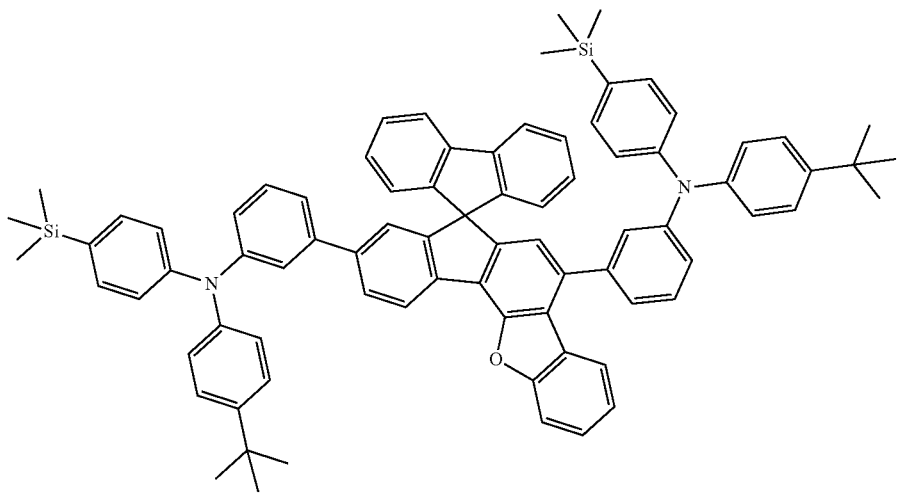
<Chemical Formula 313>
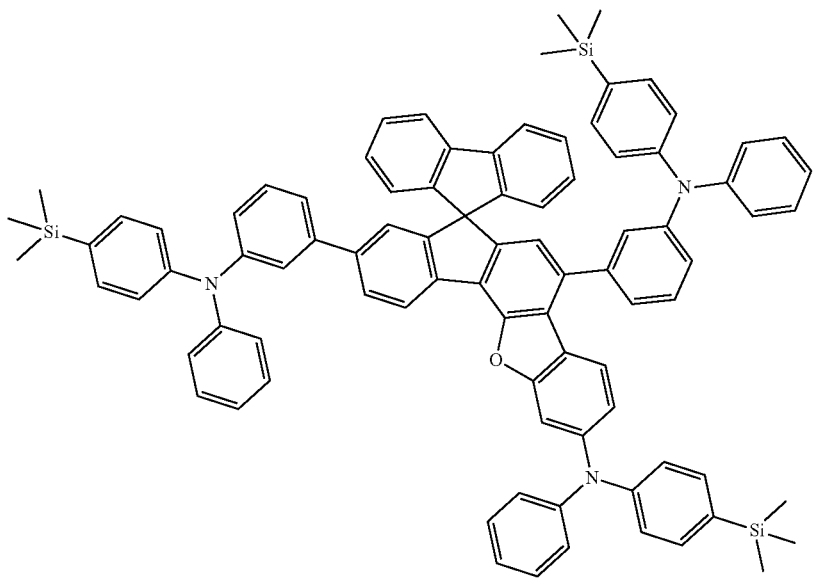
<Chemical Formula 314>
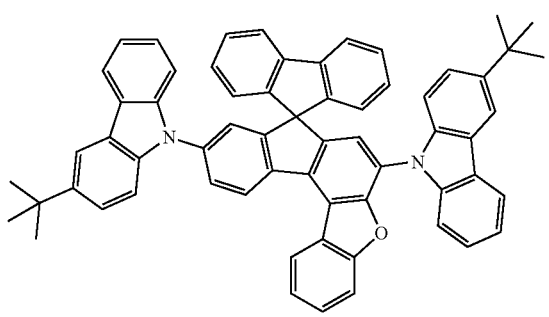
<Chemical Formula 315>
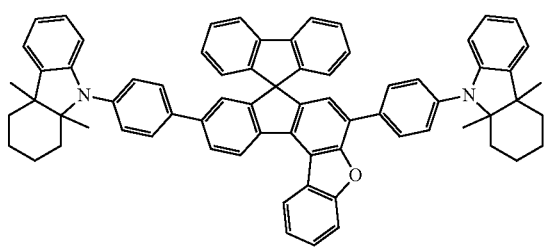

-continued
<Chemical Formula 316>
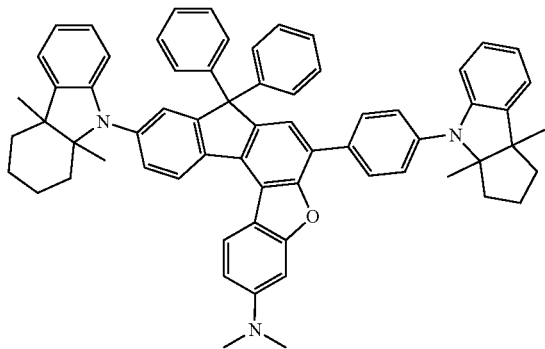
<Chemical Formula 317>
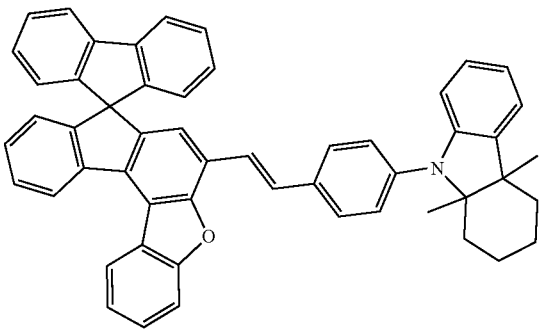
<Chemical Formula 318>
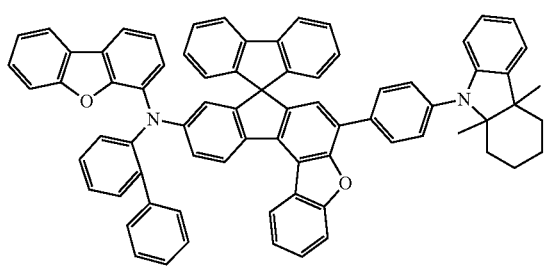
<Chemical Formula 319>
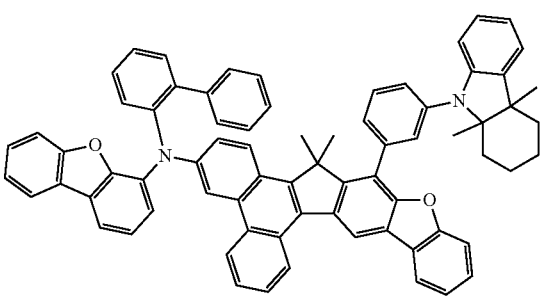
<Chemical Formula 320>
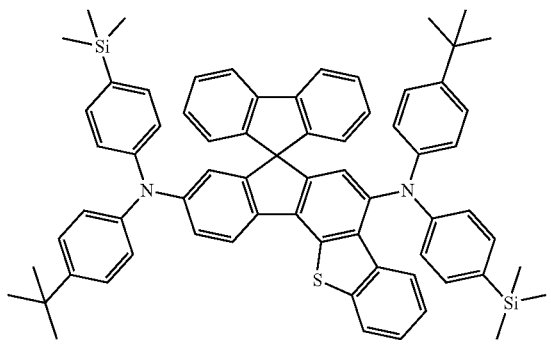
<Chemical Formula 321>
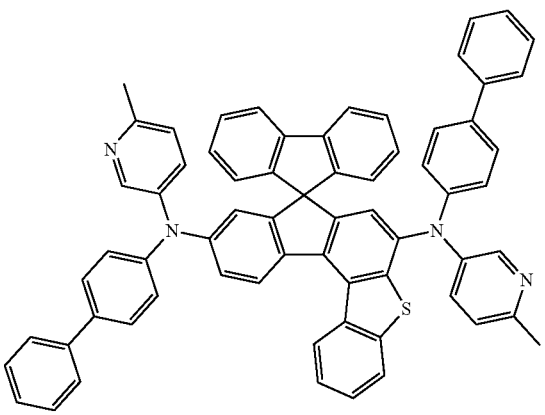
<Chemical Formula 322>
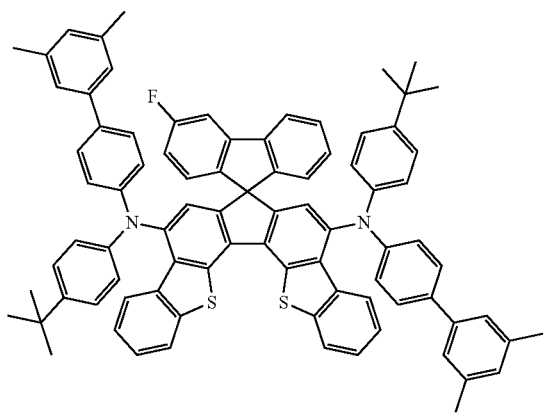
<Chemical Formula 323>
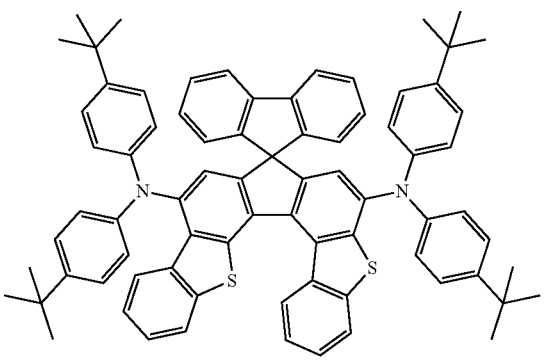

127                                                                          128
-continued
<Chemical Formula 324>
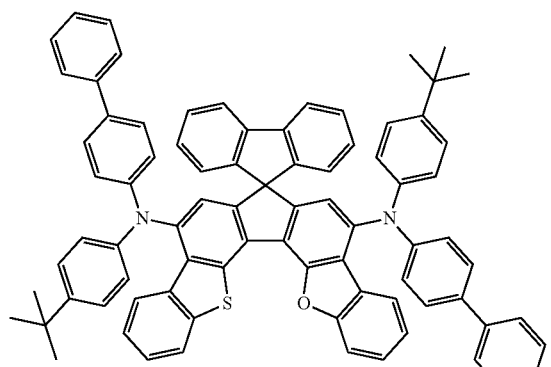
<Chemical Formula 325>
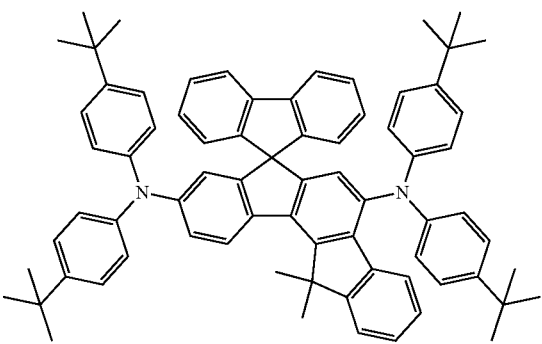
<Chemical Formula 326>
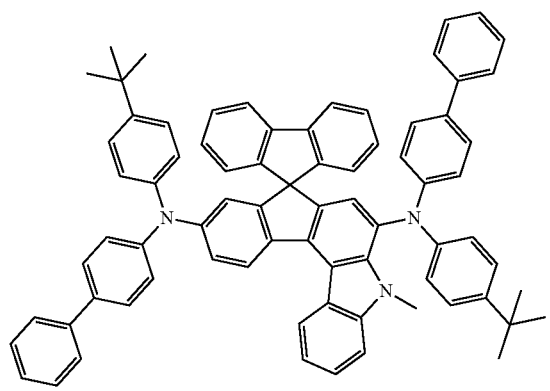
<Chemical Formula 327>
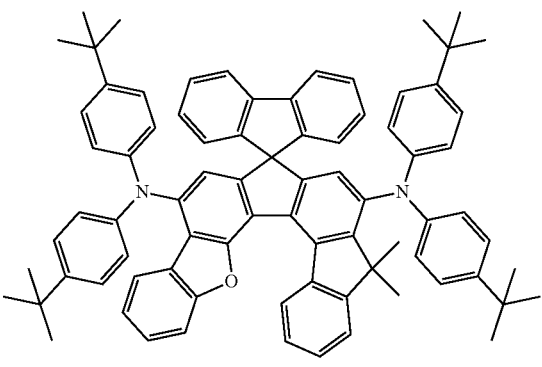
<Chemical Formula 328>
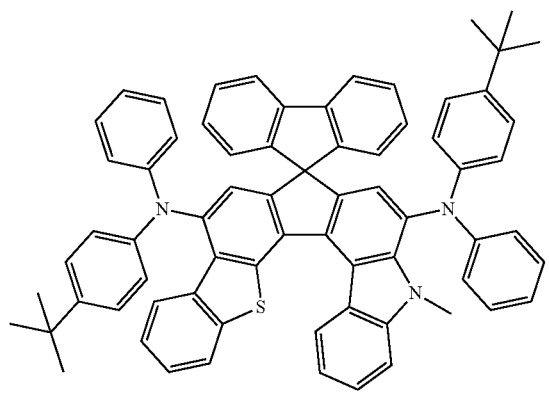
<Chemical Formula 329>
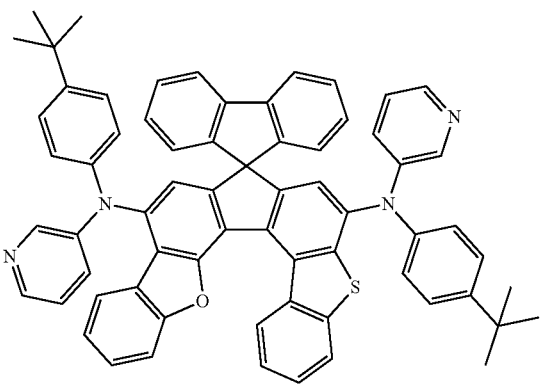
<Chemical Formula 330>
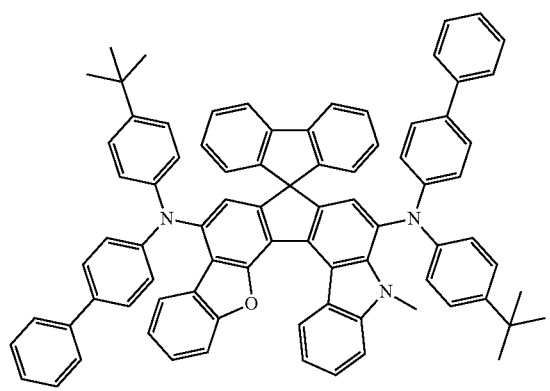
<Chemical Formula 331>
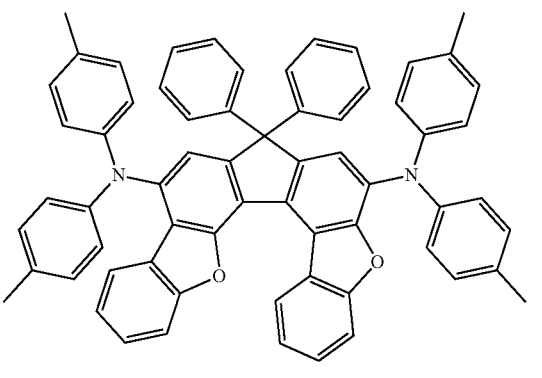

-continued
<Chemical Formula 332>
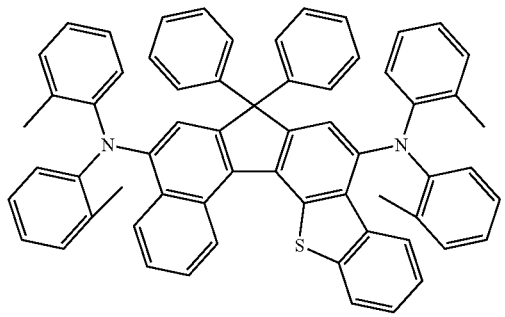
<Chemical Formula 333>
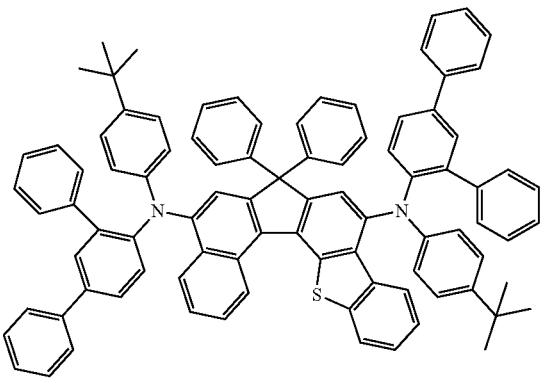
<Chemical Formula 334>
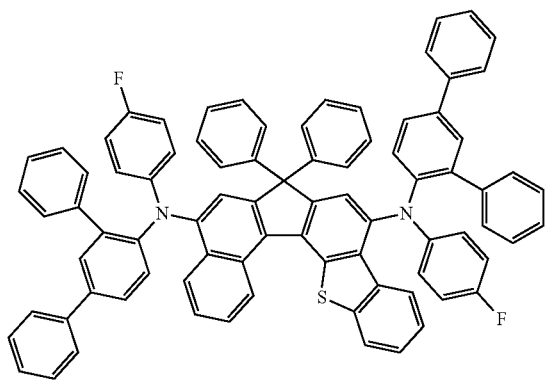
<Chemical Formula 335>
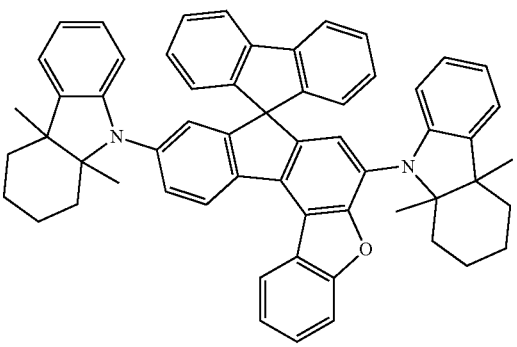
<Chemical Formula 336>
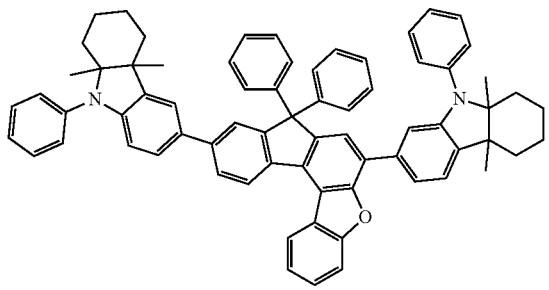
<Chemical Formula 337>
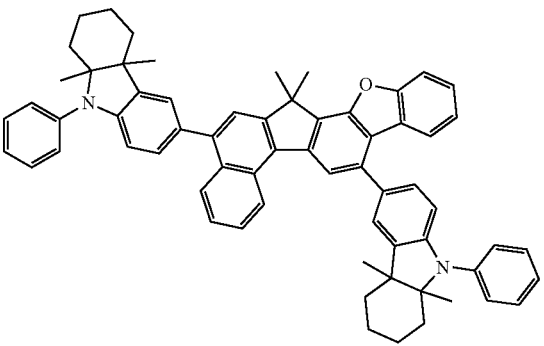
<Chemical Formula 338>
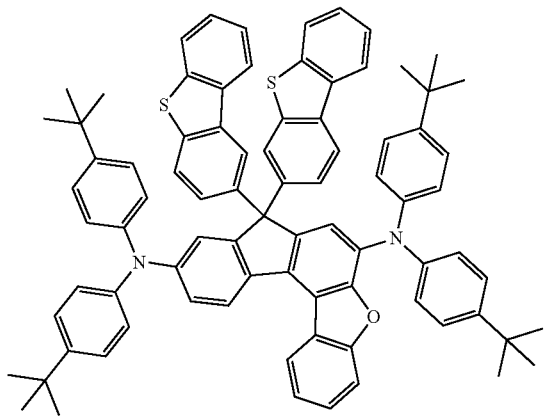
<Chemical Formula 339>
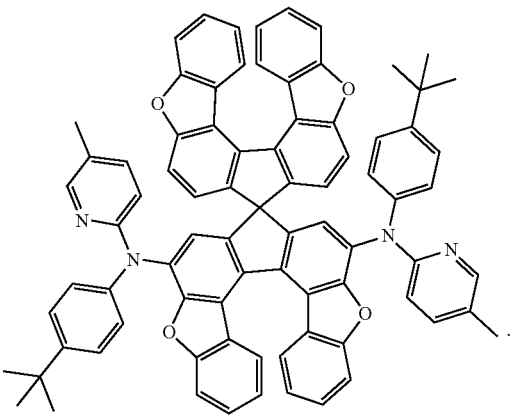

In addition, the amine bonded to the A moiety in Chemical Formulas B, C, D1, and D2 may be represented by one selected from the group consisting of [Substituent 1] to [Substituent 52], but is not limited thereto.
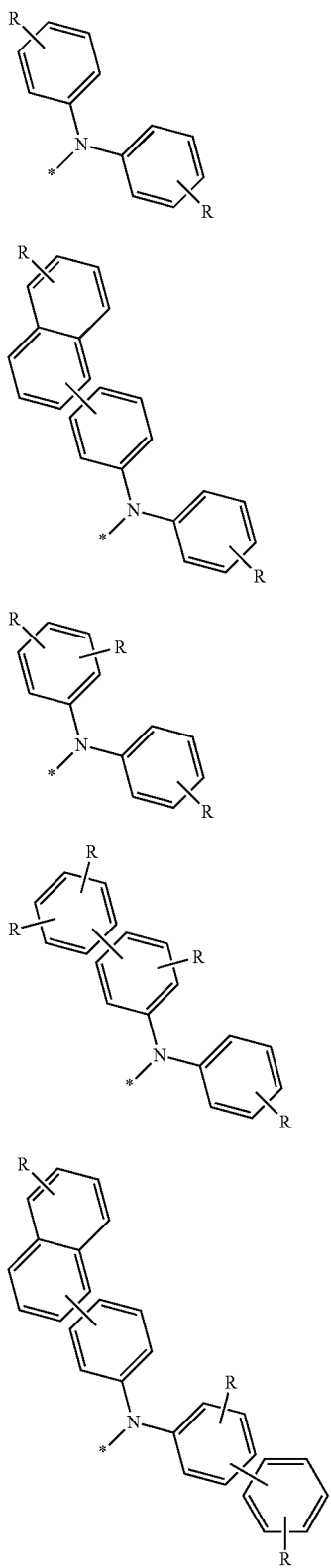
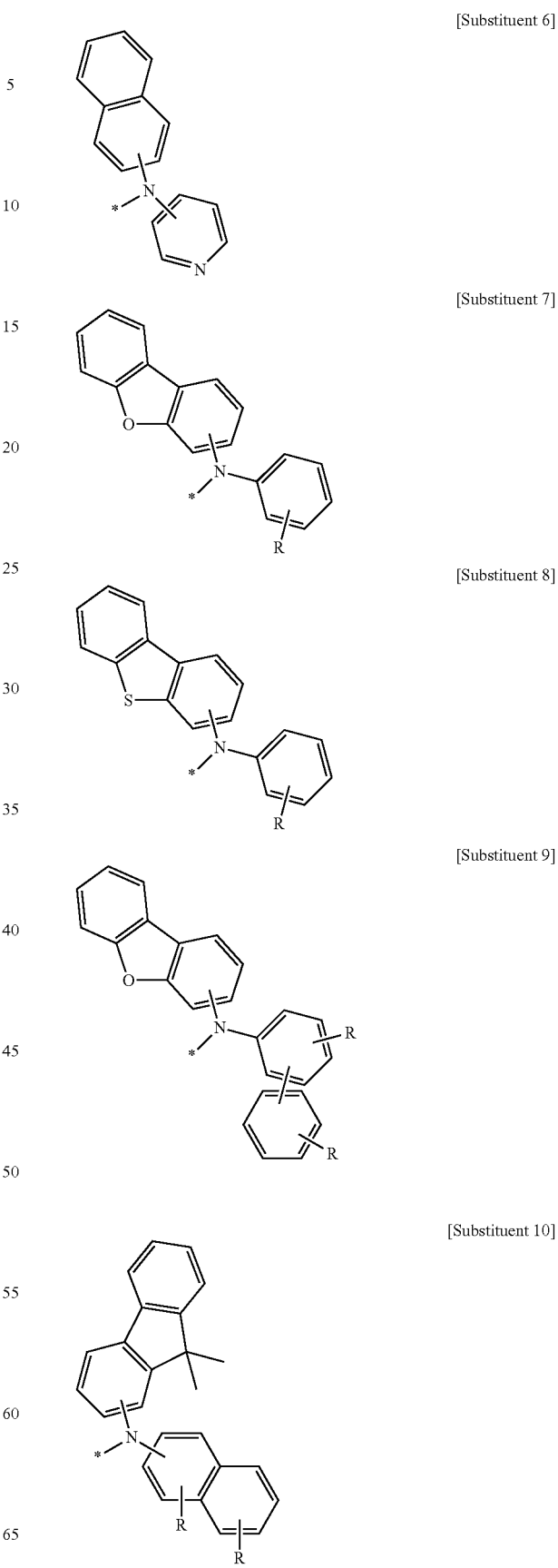

133
-continued
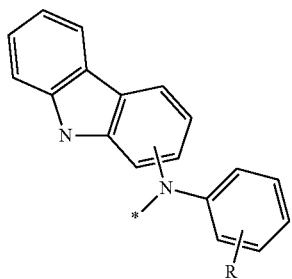
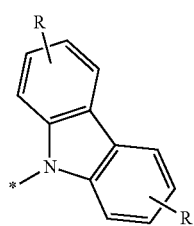
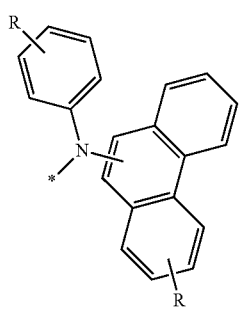
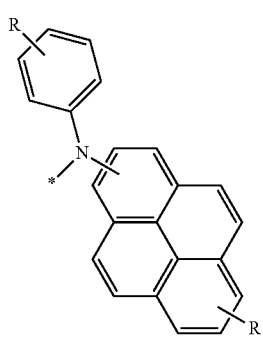
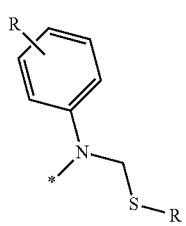
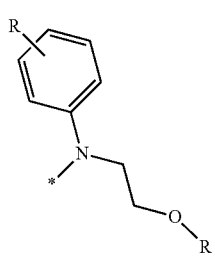
134
-continued
[Substituent 11]
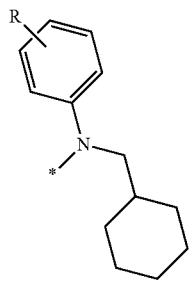
[Substituent 12]
[Substituent 13]
[Substituent 14]
[Substituent 15]
[Substituent 16]
[Substituent 17]
[Substituent 18]
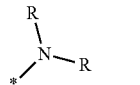
[Substituent 19]
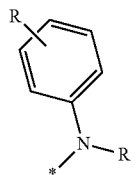
[Substituent 20]
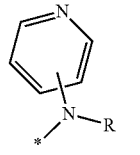
[Substituent 21]
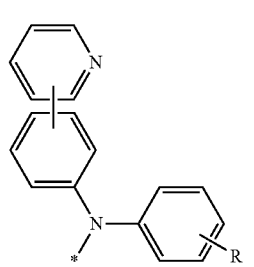
[Substituent 22]
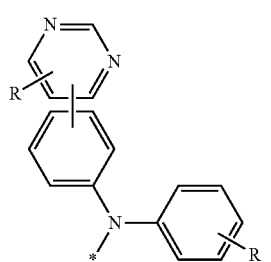
[Substituent 23]
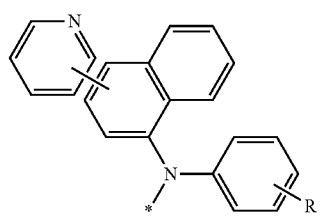

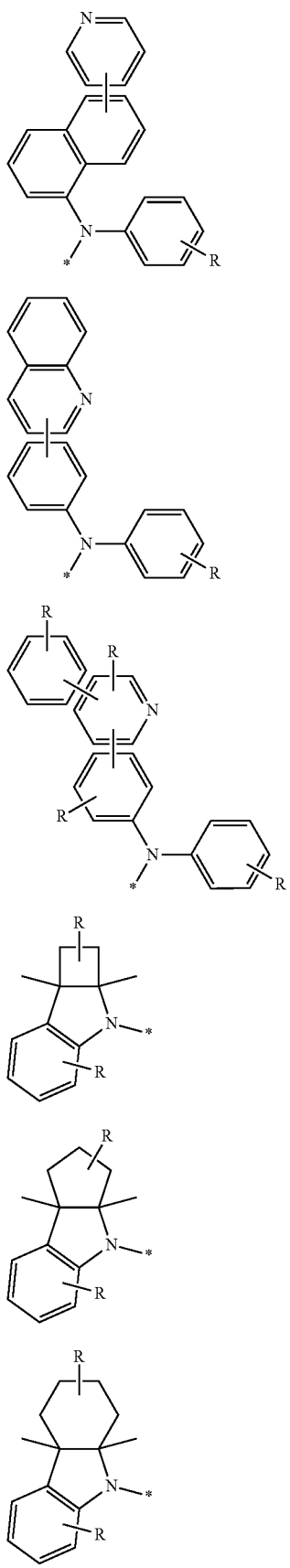

[Substituent 36] 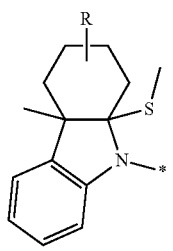
[Substituent 37] 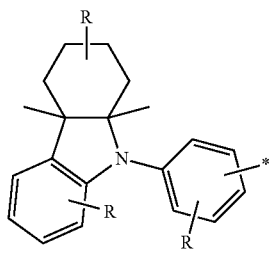
[Substituent 38] 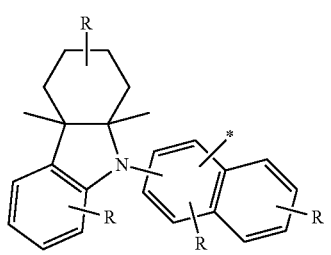
[Substituent 39] 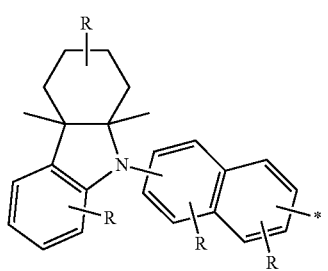
[Substituent 40] 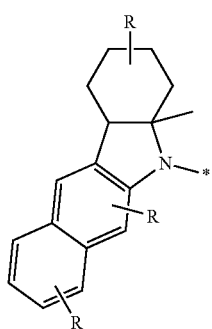
[Substituent 41] 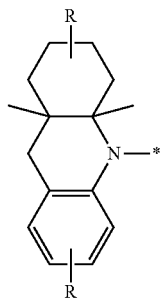
[Substituent 42] 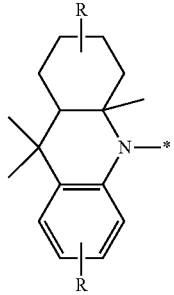
[Substituent 43] 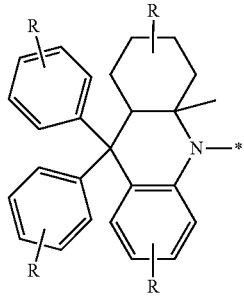
[Substituent 44] 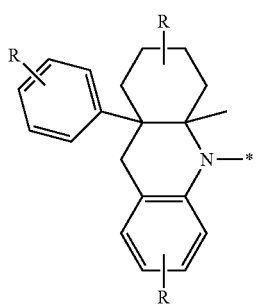
[Substituent 45] 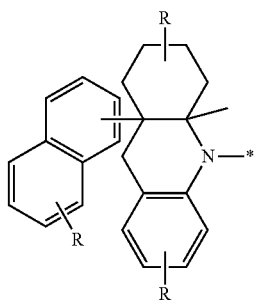

[Substituent 46]

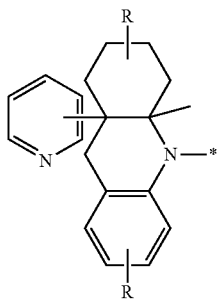

[Substituent 47]

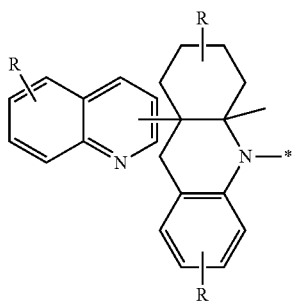

[Substituent 48]

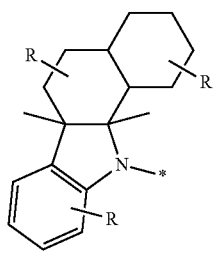

[Substituent 49]

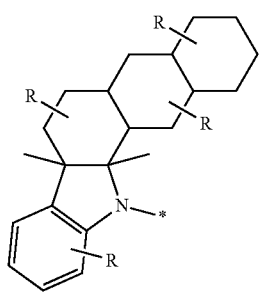

[Substituent 50]

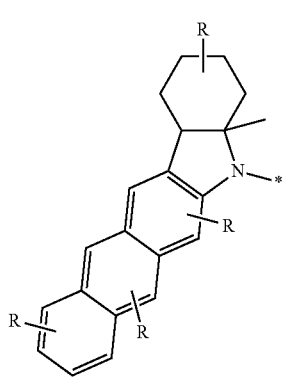

[Substituent 51]

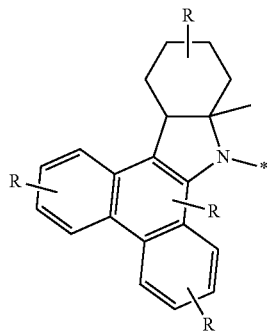

[Substituent 52]

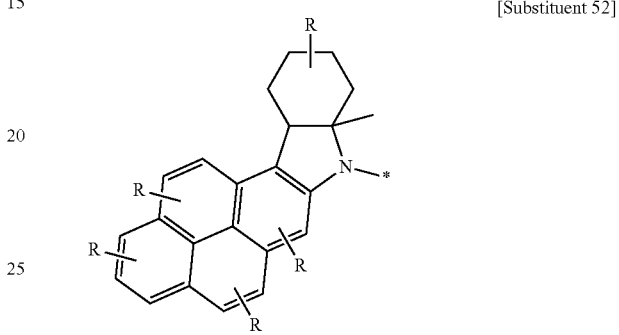

wherein R's, which may be the same or different, are each independently selected from among a hydrogen atom, a deuterium atom, a halogen atom, a hydroxyl, a cyano, a nitro, an amino, an amidino, a hydrazine, a hydrazone, a carboxyl or a salt thereof, a sulfonic acid or a salt thereof, a phosphoric acid or a salt thereof, a substituted or unsubstituted alkyl of 1 to 60 carbon atoms, a substituted or unsubstituted alkenyl of 2 to 60 carbon atoms, a substituted or unsubstituted alkynyl of 2 to 60 carbon atoms, a substituted or unsubstituted alkoxy of 1 to 60 carbon atoms, a substituted or unsubstituted alkylthio of 1 to 60 carbon atoms, a substituted or unsubstituted cycloalkyl of 3 to 60 carbon atoms, a substituted or unsubstituted aryl of 6 to 60 carbon atoms, a substituted or unsubstituted aryloxy of 6 to 60 carbon atoms, a substituted or unsubstituted arylthio of 6 to 60 carbon atoms, a substituted or unsubstituted heteroaryl of 2 to 60 carbon atoms, a substituted or unsubstituted (alkyl)amino of 1 to 60 carbon atoms, a di(substituted or unsubstituted alkyl)amino of 1 to 60 carbon atoms or a (substituted or unsubstituted aryl)amino of 6 to 60 carbon atoms, a di(substituted or unsubstituted aryl)amino of 6 to 60 carbon atoms, a substituted or unsubstituted alkylsilyl of 1 to 40 carbon atoms, a substituted or unsubstituted arylsilyl of 6 to 30 carbon atoms, a germanium, a phosphorus, and a boron and may each have 1 to 12 substituents each of which may form a fused ring with an adjacent radical.

The light-emitting layer may contain other dopants in addition to the aforementioned dopant materials.

In the organic light-emitting diode according to an embodiment of the present disclosure, the first electrode is an anode, the second electrode is a cathode, a hole injection layer is disposed in the anode and the hole transport layer, and an electron transport and an electron injection layer are sequentially arranged between the light-emitting layer and the cathode. In this regard, the organic light-emitting diode comprises a light-emitting layer between the first and the second electrode wherein the light-emitting layer includes a host, a dopant, and a hole assistant material represented by Chemical Formula A.

As used herein, the expression "(the organic layer) . . . comprising at least one organic compound" is construed to mean that the organic layer may comprise one organic compound falling within the scope of the present disclosure or two or more different compounds falling within the scope of the present disclosure.

The hole assistant material is used in an amount of 1 to 30 weight parts, based on 100 weight parts of the host, particularly in an amount of 3 to 25 weight parts, and more particularly in an amount of 5 to 10 weight parts.

When the light-emitting layer contains a host and a dopant, the content of the dopant in the light-emitting layer may range from about 0.01 to 20 parts by weight based on 100 parts by weight of the host, but is not limited thereto.

Furthermore, the hole assistant material may range in content from 0.5 to 4 times that of the dopant (wt/wt).

In the present disclosure, the light-emitting layer is particularly 50-2,000 Å thick, emitting light with a central wavelength ranging from 350 nm to 550 nm.

One or more layers selected from among a hole injection layer, a hole transport layer, a light-emitting layer, an electron transport layer, and an electron injection layer may be deposited using a deposition process or a solution process. Here, the deposition process is a process by which a material is vaporized and deposited in a vacuum or at a low pressure to form a layer, and the solution process is a method in which a material is dissolved in a solvent and applied for the formation of a thin film by means of inkjet printing, roll-to-roll coating, screen printing, spray coating, dip coating, spin coating, etc.

Also, the organic light-emitting diode of the present disclosure may be applied to a device selected from among flat display devices, flexible display devices, monochrome or grayscale flat illumination devices, and monochrome or grayscale flexible illumination devices.

Figure 2:
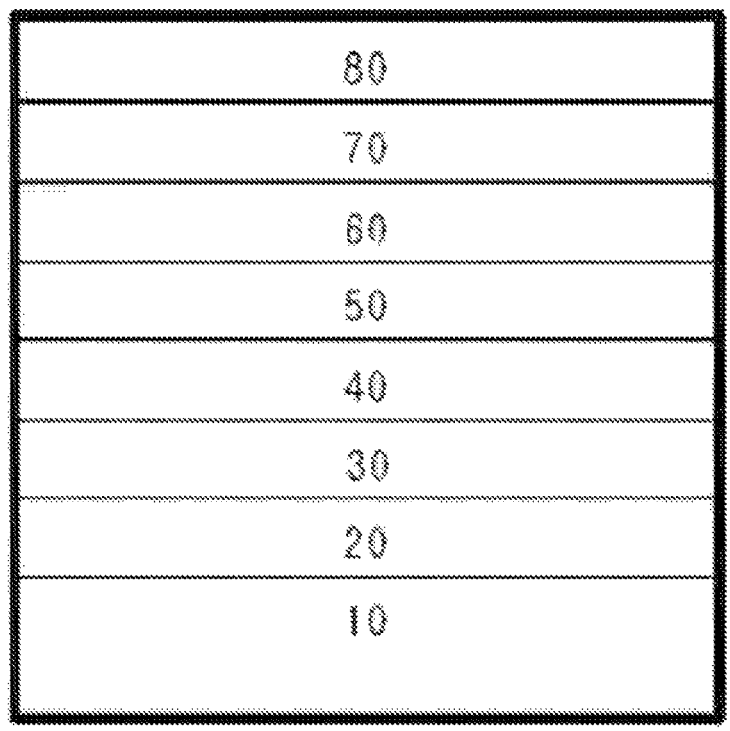
FIG. 2 is a schematic view of an organic light-emitting diode according to an embodiment of the present disclosure.

In FIG. 2, which depicts a structure according to a concrete embodiment of the present disclosure, a hole injection layer and a hole transport layer (HTL) are arranged between the anode and the light-emitting layer while an electron transport layer (ETL) and an electron injection layer are disposed between the cathode and the light-emitting layer.

For use as a material in a hole transport layer, an electron donating molecule having a low ionization potential is suitable. Predominantly, diamine, triamine or tetraamine derivatives having a triphenylamine skeleton are employed, as exemplified by N,N'-bis(3-methylphenyl)-N,N'-diphenyl-[1,1-biphenyl]-4,4'-diamine (TPD) and N,N'-di(naphthalen-1-yl)-N,N'-diphenylbenzidine (a-NPD).

A hole injection layer (HIL) may be further deposited beneath the hole transport layer. No particular limitations are imparted to the hole injection layer material, as long as it is one that is typically used in the art. Examples include CuPc (copper phthalocyanine), and the starburst amines TCTA (4,4',4''-tri(N-carbazolyl)triphenyl-amine), and m-MTDATA (4,4',4''-tris-(3-methylphenylphenyl amino)triphenylamine).

Meanwhile, the electron transport material functions to stably transport electrons injected from the electron injection electrode (cathode) and may be a material well known in the art. Examples of the well-known material include quinoline derivatives, particularly tris(8-quinolinolate)aluminum (Alq3), Liq, TAZ, BAlq, beryllium bis(benzoquinolin-10-olate: Bebq2), BCP, compound 201, compound 202, BCP, and the oxadiazole derivatives PBD, BMD, and BND, but are not limited thereto.

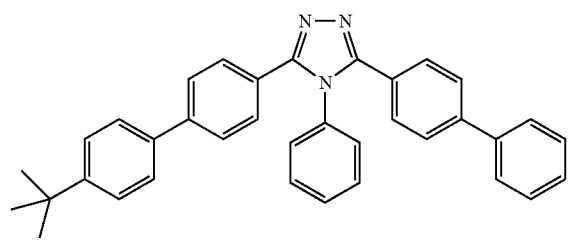

TAZ

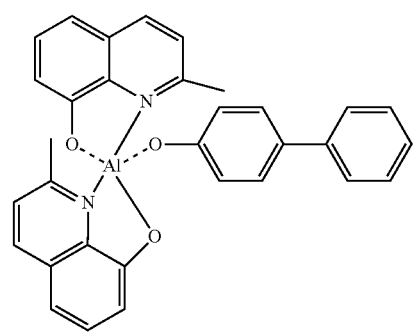

BAlq

<Compound 201>

<Compound 202>

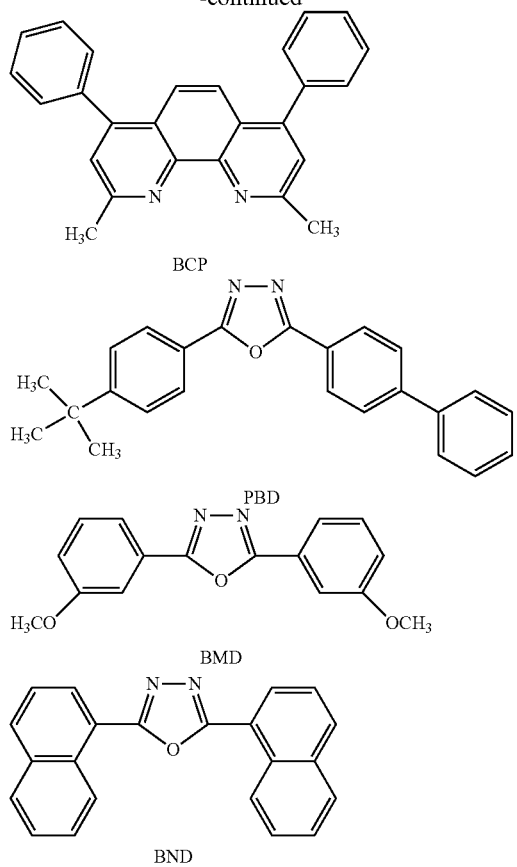

BCP

PBD

BMD

BND

In addition, the organic metal compound represented by Chemical Formula F may be used, either alone or in combination with the aforementioned material, as a compound for an electron transport layer in the present disclosure:

$Y_m$-M-(OA)$_n$  [Chemical Formula F]

wherein,

Y is a ligand that contains two moieties respectively responsible for forming a single bond through a direct bond to M and for forming a coordinate bond with M, each moiety being selected from among C, N, O and S, and which is chelated by the single bond and the coordinate bond; M is an alkali metal, an alkaline earth metal, an aluminum (Al) atom, or a boron (B) atom, with the proviso that:

when M is an alkali metal, m=1 and n=0;

when M is an alkaline earth metal, m=1 and n=1, or m=2 and n=0; or when M is aluminum or a boron, m is an integer of 1 to 3 and n is an integer of 0 to 2, satisfying the relationship m+n=3; and OA is a monodentate ligand capable of forming a single bond or a coordinate bond with M, wherein O is oxygen, and A is selected from among a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, and a substituted or unsubstituted heteroaryl of 2 to 50 carbon atoms bearing O, N, or S as a heteroatom.

In the present disclosure, Y's may be the same or different and may each be one selected from among, but not limited to, the following [Structural Formula C1] to [Structural Formula C39]:

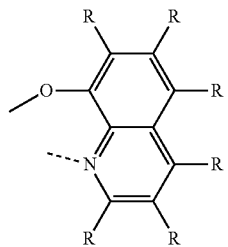

[Structural FormulaC1]

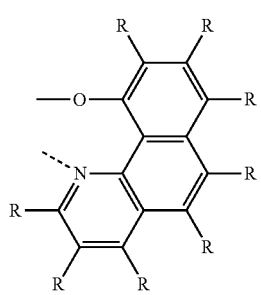

[Structural FormulaC2]

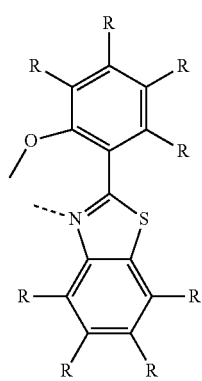

[Structural FormulaC3]

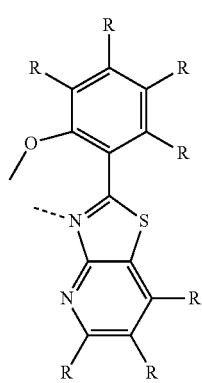

[Structural Formula C4]

[Structural Formula C5]
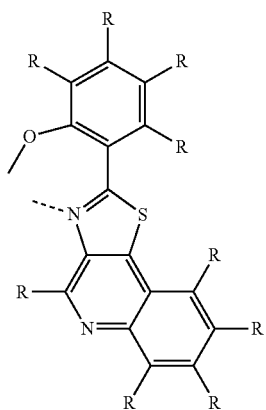
[Structural Formula C6]
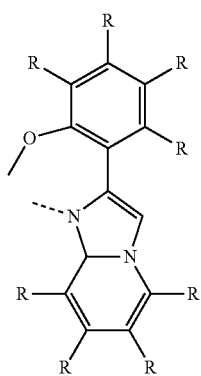
[Structural Formula C7]
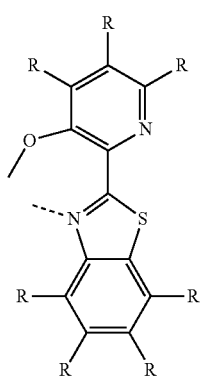
[Structural Formula C8]
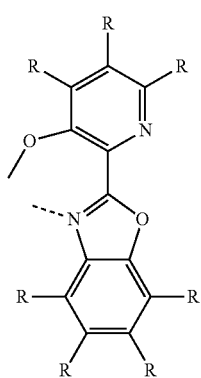
[Structural Formula C9]
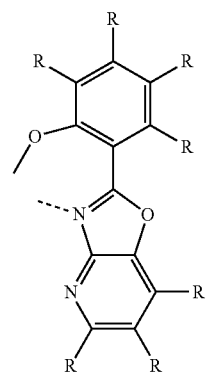
[Structural Formula C10]
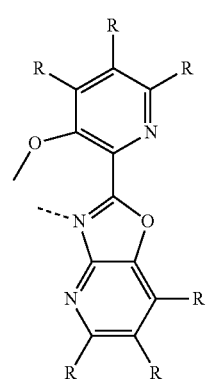
[Structural Formula C11]
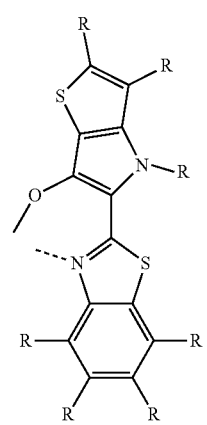
[Structural Formula C12]
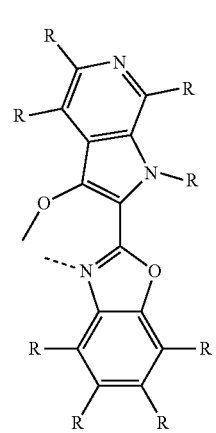

[Structural Formula C13]
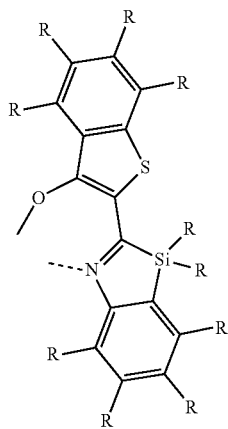
[Structural Formula C14]
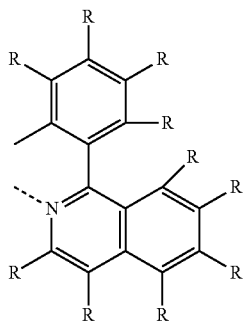
[Structural Formula C15]
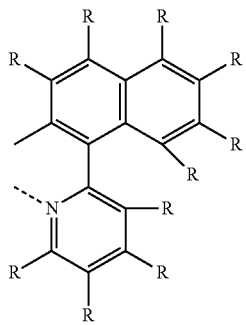
[Structural Formula C16]
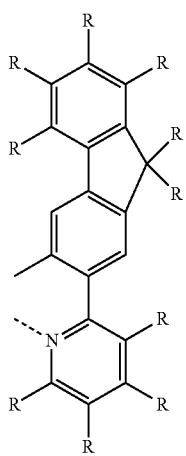
[Structural Formula C17]
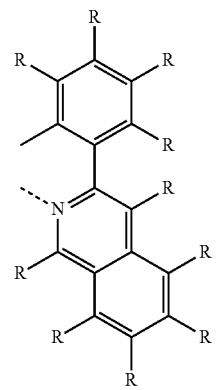
[Structural Formula C18]
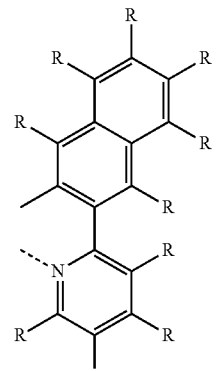
[Structural Formula C19]
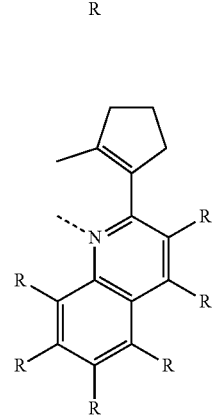
[Structural Formula C20]
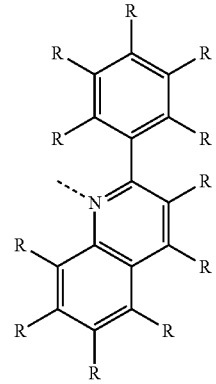

[Structural Formula C21]
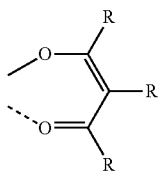
[Structural Formula C22]
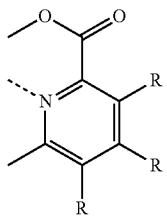
[Structural Formula C23]
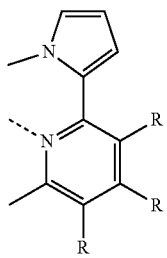
[Structural Formula C24]
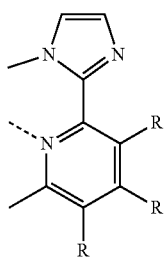
[Structural Formula C25]
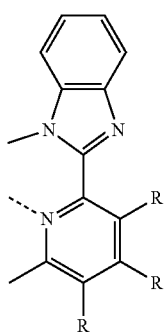
[Structural Formula C26]
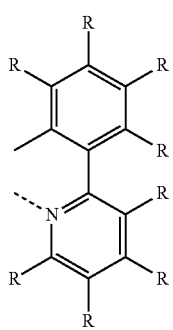
[Structural Formula C27]
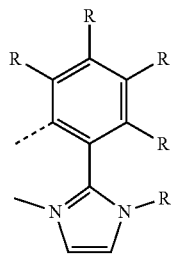
[Structural Formula C28]
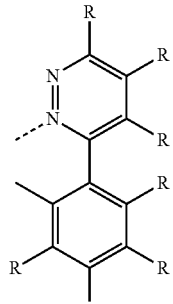
[Structural Formula C29]
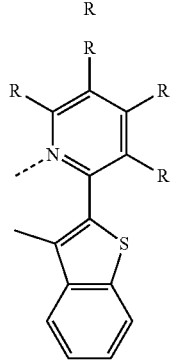
[Structural Formula C30]
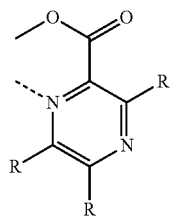
[Structural Formula C31]
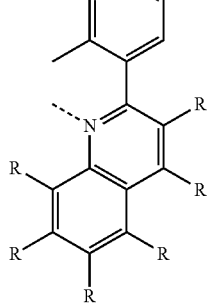

-continued

[Structural Formula C32]

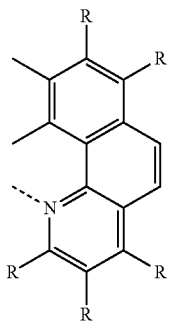

[Structural Formula C33]

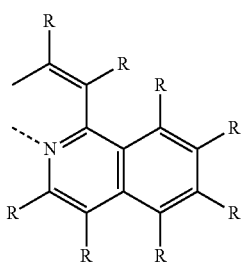

[Structural Formula C34]

[Structural Formula C35]

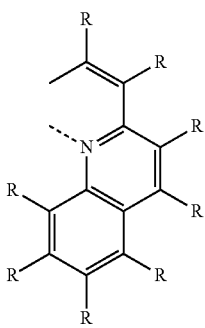

[Structural Formula C36]

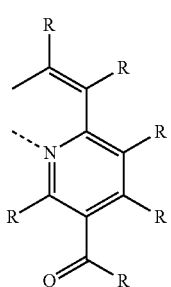

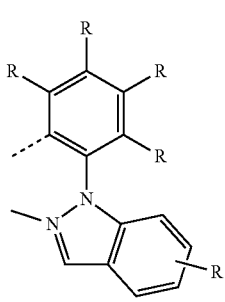

-continued

[Structural Formula C37]

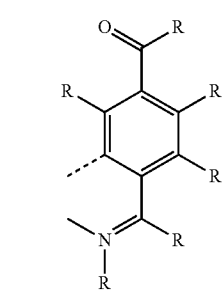

[Structural Formula C38]

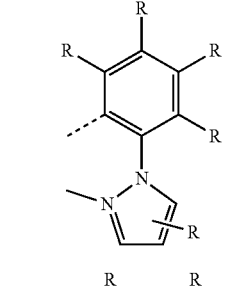

[Structural Formula C39]

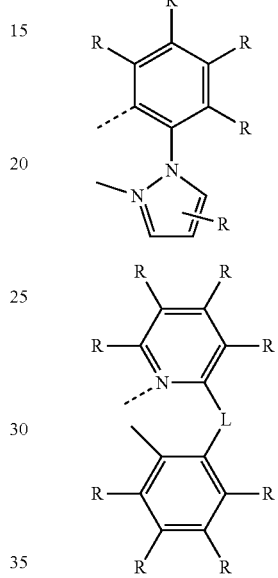

wherein,

R's, which may be the same or different, are each independently selected from among a hydrogen atom, a deuterium atom, a halogen, a cyano, a substituted or unsubstituted alkyl of 1 to 30 carbon atoms, a substituted or unsubstituted aryl of 6 to 30 carbon atoms, a substituted or unsubstituted heteroaryl of 3 to 30 carbon atoms, a substituted or unsubstituted alkoxy of 1 to 30 carbon atoms, a substituted or unsubstituted cycloalkyl of 3 to 30 carbon atoms, a substituted or unsubstituted alkenyl of 2 to 30 carbon atoms, a substituted or unsubstituted alkylamino of 1 to 30 carbon atoms, a substituted or unsubstituted alkylsilyl of 1 to 30 carbon atoms, a substituted or unsubstituted arylamino of 6 to 30 carbon atoms, and a substituted or unsubstituted arylsilyl of 6 to 30 carbon atoms, and may form a spiro or fused ring with an adjacent substituent via an alkylene or alkenylene linker. Here, the term "substituted" in the expression "substituted or unsubstituted" means having at least one substituent selected from the group consisting of a deuterium atom, a cyano, a halogen, a hydroxy, a nitro, an alkyl, an alkoxy, an alkylamino, an arylamino, a heteroarylamino, an alkylsilyl, an arylsilyl, an aryloxy, an aryl, a heteroaryl, a germanium, a phosphorus, and a boron.

An electron injection layer (EIL) that functions to facilitate electron injection from the cathode, thus improving the power efficiency of the diode, may be further deposited on the electron transport layer. So long as it is conventionally used in the art, any material can be available for the electron injection layer without particular limitations. Examples include LiF, NaCl, CsF, $Li_2O$, and BaO.

The electron injection layer may range in thickness from about 1 Å to about 100 Å, and particularly from about 3 Å to about 90 Å. Given the thickness range for the electron injection layer, the diode can exhibit satisfactory electron injection properties without actually elevating a driving voltage.

Below, the organic light-emitting diode of the present disclosure is explained with reference to FIG. 2.

FIG. 2 is a schematic cross-sectional view of the structure of an organic light-emitting diode according to some embodiments of the present disclosure. The organic light-emitting diode includes an anode 20, a hole transport layer 40, an organic light-emitting layer 50, an electron transport layer 60, and a cathode 80, and optionally a hole injection layer 30 or an electron injection layer 70. In addition, one or two intermediate layers may be further formed in the organic light-emitting diode.

Reference is made to FIG. 2 with regard to the organic light-emitting diode of the present disclosure and the fabrication thereof. First, a substrate 10 is coated with an anode electrode material to form an anode 20. So long as it is used in a typical organic EL device, any substrate may be used as the substrate 10. Preferable is an organic substrate or transparent plastic substrate that exhibits excellent transparency, surface smoothness, ease of handling, and waterproofness. As the anode electrode material, indium tin oxide (ITO), indium zinc oxide (IZO), tin oxide ($SnO_2$), or zinc oxide (ZnO), which are transparent and superior in terms of conductivity, may be used.

A hole injection layer material is applied on the anode electrode 20 by thermal deposition in a vacuum or by spin coating to form a hole injection layer 30. Subsequently, using thermal deposition in a vacuum or spin coating, a hole transport layer material is applied to the hole injection layer 30 to form a hole transport layer 40.

Then, an organic light-emitting layer 50 is deposited on the hole transport layer 40, optionally followed by the formation of a hole barrier layer (not shown) on the organic light-emitting layer 50 by deposition in a vacuum or by spin coating. When holes traverse the organic light-emitting layer and are introduced into the cathode, the efficiency and lifespan of the diode are deteriorated. Formed of a material with a low HOMO (Highest Occupied Molecular Orbital) level, the hole barrier layer serves to prevent the introduction of holes into the cathode. Any material that has a higher ionization potential than the light-emitting compound and which is also able to carry electrons may be used for the hole barrier layer without limitations. Representative among hole barrier materials are BAlq, BCP, and TPBI.

Using a vacuum deposition method or a spin-coating method, an electron transport layer 60 may be deposited on the hole barrier layer and may then be overlaid with an electron injection layer 70. A cathode metal is deposited on the electron injection layer 70 by thermal deposition in a vacuum to form a cathode 80, thus obtaining an organic EL diode. Here, the cathode may be made of lithium (Li), magnesium (Mg), aluminum (Al), aluminum-lithium (Al—Li), calcium (Ca), magnesium-indium (Mg—In), or magnesium-silver (Mg—Ag). For a top-emitting OLED, a transparent cathode made of ITO or IZO may be employed.

A better understanding of the light-emitting diode according to the present disclosure may be obtained through the following examples which are set forth to illustrate, but are not to be construed as limiting the present disclosure.

Preparation of Dopant Compound

Synthesis Example 1: Synthesis of Compound of Chemical Formula 101

Synthesis Example 1-(1): Synthesis of [Intermediate 1-a]

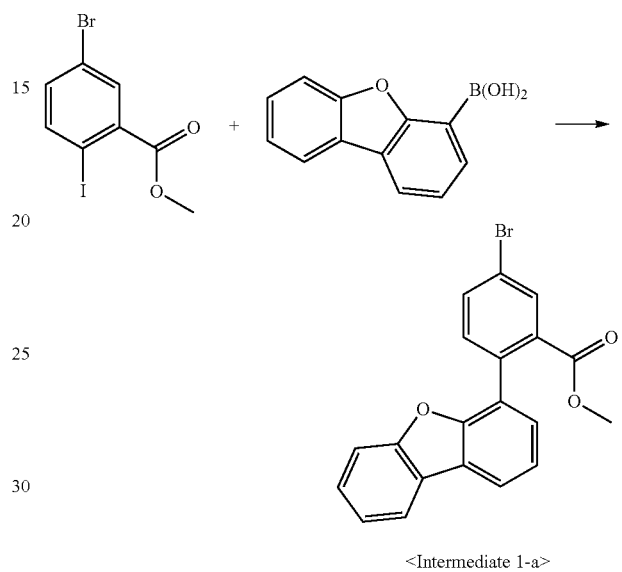

<Intermediate 1-a>

In a 500-mL round-bottom flask reactor, methyl 5-bromo-2-iodobenzoate (25.0 g, 73 mmol), 4-dibenzofuran boronic acid (18.7 g, 88 mmol), tetrakis(triphenylphosphine)palladium (1.7 g, 0.15 mmol), and potassium carbonate (20.2 g, 146.7 mmol) were stirred together with toluene (125 mL), tetrahydrofuran (125 mL), and water (50 mL) for 10 hrs at 80° C. After completion of the reaction, the reaction mixture was cooled to room temperature and extracted with ethyl acetate. The organic layer thus formed was separated, concentrated in a vacuum, and purified by column chromatography to afford <Intermediate 1-a>. (75.0 g, 60.1%).

Synthesis Example 1-(2): Synthesis of [Intermediate 1-b]

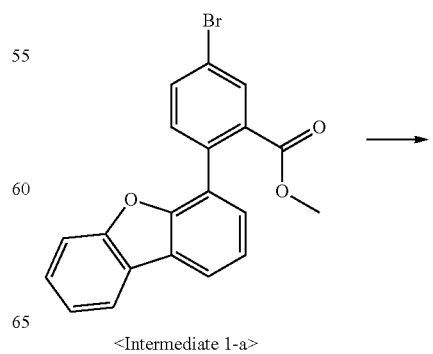

<Intermediate 1-a>

-continued

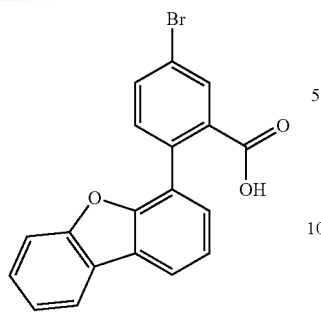

<Intermediate 1-b>

In a 500-mL round-bottom flask reactor, <Intermediate 1-a> (17.0 g, 45 mmol), sodium hydroxide (2.14 g, 54 mmol) and ethanol (170 ml) were stirred together for 48 hrs under reflux. After the completion of the reaction was confirmed using thin-layer chromatography, the reaction mixture was cooled to room temperature. The chilled solution was acidified with drops of 2-N HCl, followed by stirring for 30 min. The solid thus formed was filtered and then recrystallized in dichloromethane and n-hexane to afford <Intermediate 1-b>. (14.5 g, 88.6%)

Synthesis Example 1-(3): Synthesis of [Intermediate 1-c]

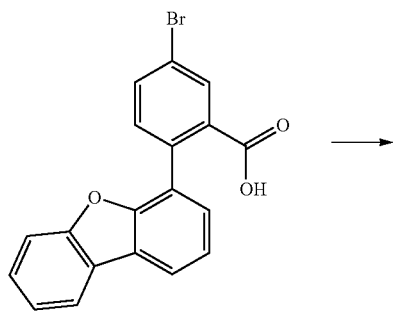

<Intermediate 1-b>

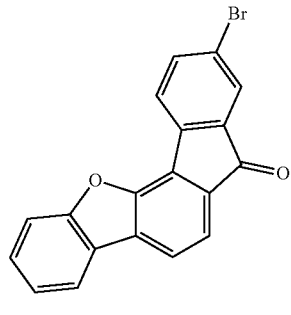

<Intermediate 1-c>

In a 250-mL round-bottom flask reactor, <Intermediate 1-b> (14.5 g, 39 mmol) and methanesulfonic acid (145 ml) were stirred together for 3 hrs at 80° C. After the completion of the reaction was confirmed using thin-layer chromatography, the reaction mixture was cooled to room temperature and dropwise added to ice water (150 ml). After stirring for 30 min, the solid thus formed was filtered and washed with water and methanol to afford <Intermediate 1-c>. (11.50 g, 83.4%)

Synthesis Example 1-(4): Synthesis of [Intermediate 1-d]

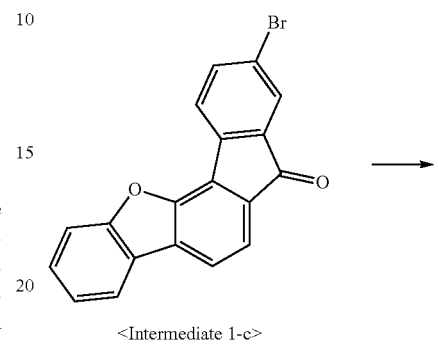

<Intermediate 1-c>

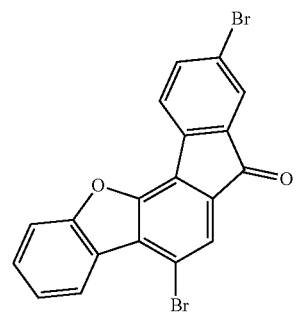

<Intermediate 1-d>

In a 1-L round-bottom flask reactor, <Intermediate 1-c> (11.5 g, 33 mmol> and dichloromethane (300 ml) were stirred together at room temperature. A dilution of bromine (3.4 ml, 66 mmol) in dichloromethane (50 ml) was dropwise added, followed by stirring at room temperature for 8 hrs. After completion of the reaction, the reaction mixture was stirred together with acetone (100 ml). The solid thus formed was filtered and washed with acetone. Recrystallization in monochlorobenzene afforded <Intermediate 1-d>. (11.0 g, 78%)

Synthesis Example 1-(5): Synthesis of [Intermediate 1-e]

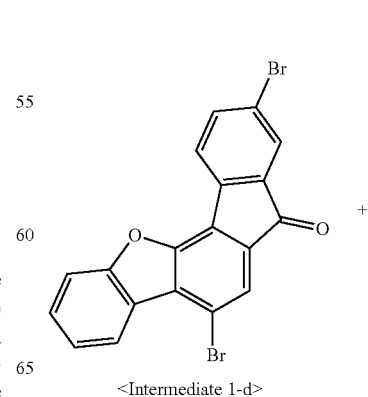

<Intermediate 1-d>

-continued

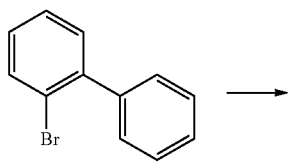

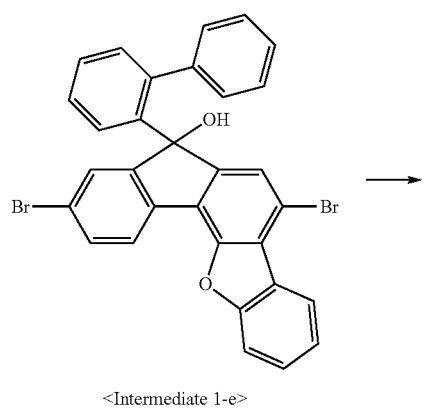

<Intermediate 1-e>

In a 250-ml round-bottom flask reactor, 2-bromobiphenyl (8.4 g, 0.036 mol) and tetrahydrofuran (110 ml) were chilled at −78° C. in a nitrogen atmosphere. At the same temperature, n-butyl lithium (19.3 ml, 0.031 mol) was dropwise added to the chilled reaction solution, which was then stirred for 2 hrs. Thereafter, <Intermediate 1-d> (11.0 g, 0.026 mol) was added little by little to the reaction solution and stirred at room temperature. When the reaction mixture started to change color, the reaction was monitored via TLC. After the reaction was stopped with H₂O (50 ml), extraction was conducted with ethyl acetate and water. The organic layer was separated, concentrated in a vacuum, and recrystallized in acetonirile to afford <Intermediate 1-e> as a solid. (12.2 g, 81.5%)

Synthesis Example 1-(6): Synthesis of [Intermediate 1-f]

-continued

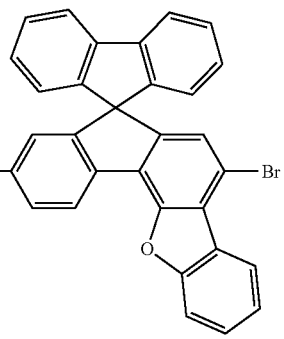

<Intermediate 1-f>

In a 250-ml round-bottom flask reactor, a mixture of <Intermediate 1-e> (12.0 g, 0.021 mol), acetic acid (120 ml), and sulfuric acid (2 ml) was stirred for 5 hrs under reflux. When a precipitate was formed, the completion of the reaction was monitored using thin-layer chromatography. The reaction mixture was then cooled to room temperature and filtered. The filtrate was washed with H₂O and methanol and dissolved in monochlorobenzene. Following silica gel chromatography, the fraction was concentrated and cooled to room temperature to give <Intermediate 1-f>. (10.7 g, 90%>

Synthesis Example 1-(7): [Chemical Formula 101]

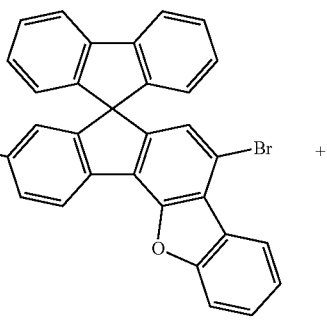

<Intermediate 1-f>

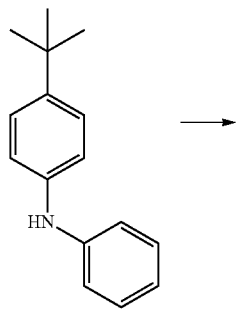

-continued

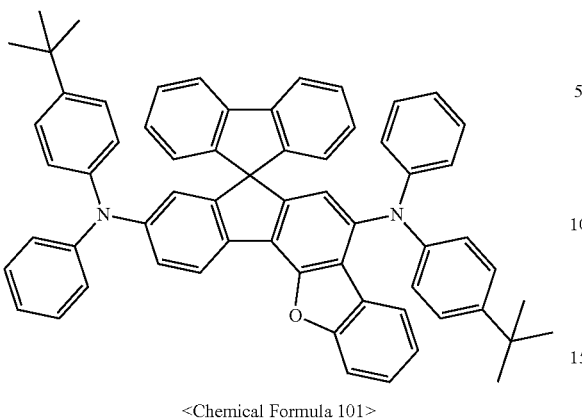

<Chemical Formula 101>

In a 250-ml round-bottom flask reactor, a mixture of <Intermediate 1-f> (5.0 g, 0.009 mol), (4-tert-butylphenyl)-phenylamine (4.7 g, 0.021 mol), palladium (II) acetate (0.08 g, 0.4 mmol), sodium tert-butoxide (3.4 g, 0.035 mol), tri-tert-butyl phosphine (0.07 g, 0.4 mmol), and toluene (60 ml) was stirred for 2 hrs under reflux. After completion of the reaction, the reaction mixture was cooled to room temperature and then extracted with dichloromethane and water. The organic layer thus formed was separated, dried over magnesium sulfate, and concentrated in a vacuum. The concentrate was purified by column chromatography and recrystallized in dichloromethane and acetone to yield the compound of Chemical Formula 101 as a solid (2.9 g, 38%).

MS (MALDI-TOF): m/z 852.41 [Mt]

Synthesis Example 2: Synthesis of Compound of Chemical Formula 198

Synthesis Example 2-(1): Synthesis of Intermediate 2-a

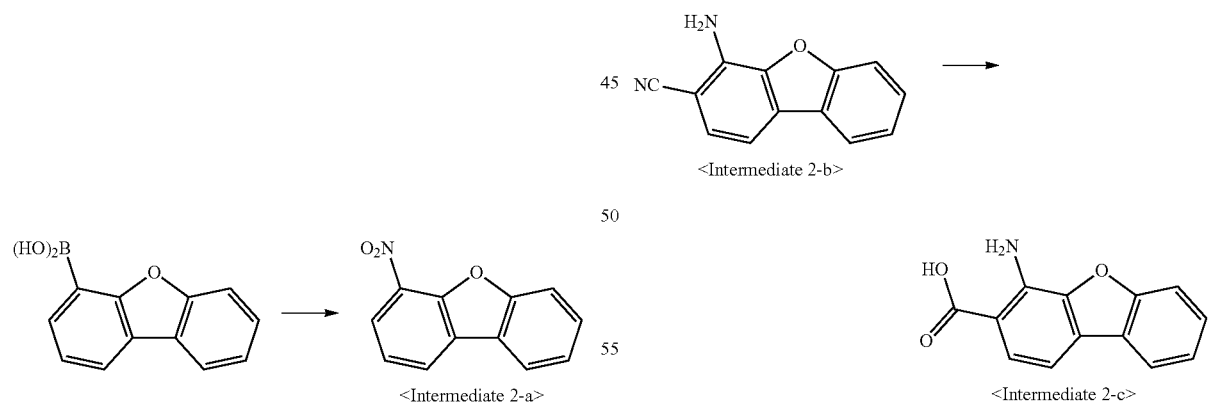

<Intermediate 2-a>

In a 1-L round-bottom flask reactor, dibenzofuran-4-bronic acid (85.0 g, 0.401 mol), bismuth (III) nitrate pentahydrate (99.2 g, 0.200 mol), and toluene (400 ml) were reacted at 70° C. for 3 hrs under a nitrogen atmosphere while stirring. After completion of the reaction, the reaction mixture was cooled to room temperature and washed with toluene. Filtration afforded <Intermediate 2-a> as a solid (61.5 g, 72%).

Synthesis Example 2-(2): Synthesis of Intermediate 2-b

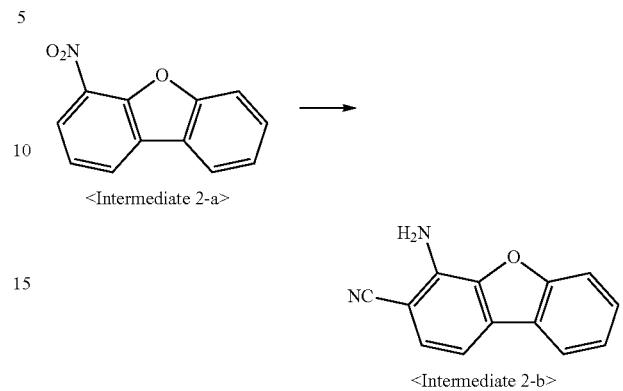

In a 2-L round-bottom flask reactor, ethylcyanoacetate (202.9 g, 1.794 mol), and dimethylformamide (500 ml) were added with potassium hydroxide (67.1 g, 1.196 mol), potassium cyanide (38.95 g, 0.598 mol), and dimethylformamide (200 ml), followed by stirring at room temperature. To this reaction solution, <Intermediate 2-a> (127.5 g, 0.737 mol) was slowly added while stirring at 50° C. for 72 hrs. After completion of the reaction, an aqueous sodium hydroxide solution (25%, 200 ml) was added, and stirred for 3 hrs under reflux. Subsequently, the reaction mixture was cooled to room temperature, followed by extraction with ethyl acetate and water. The organic layer was separated and concentrated. Purification by column chromatography afforded <Intermediate 2-b> (20.0 g, 16%).

Synthesis Example 2-(3): Synthesis of Intermediate 2-c

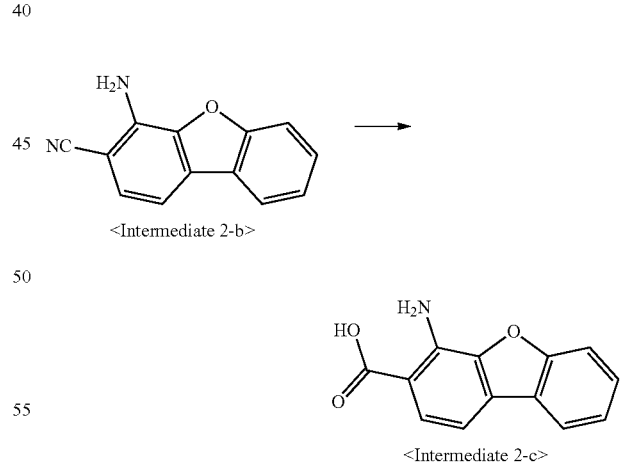

In a 2-L round-bottom flask reactor, a mixture of <Intermediate 2-b> (20.0 g, 0.096 mol), ethanol (600 ml), and potassium hydroxide (170 ml, 142.26 g, 2.53 mol) was stirred for 12 hrs under reflux. After completion of the reaction mixture was cooled to room temperature, and then acidified with 6 N HCl (400 ml). Stirring for 20 min was followed by filtration. The solid thus obtained was washed with ethanol to afford <Intermediate 2-c> (17.0 g, 88.5%).

Synthesis Example 2-(4): Synthesis of Intermediate 2-d

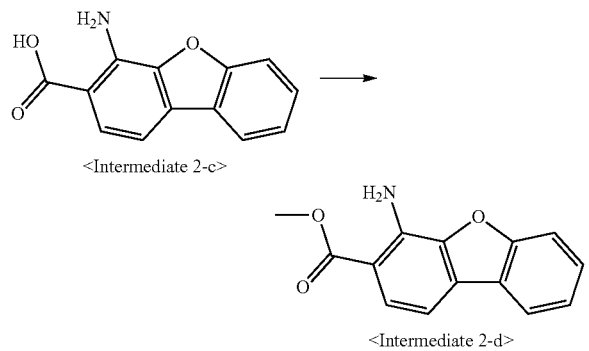

In a 2-L round-bottom flask reactor, a mixture of <Intermediate 2-c> (17.0 g, 0.075 mol) and sulfuric acid (15 ml) was stirred for 72 hrs under reflux. After completion of the reaction, the reaction mixture was extracted with ethyl acetate and water. The organic layer was separated and washed with an aqueous sodium hydrogen carbonate solution. An excess of methanol was added during the vacuum concentration of the organic layer, followed by filtration to afford <Intermediate 2-d>. (14.0 g, 77.6%)

Synthesis Example 2-(5): Synthesis of Intermediate 2-e

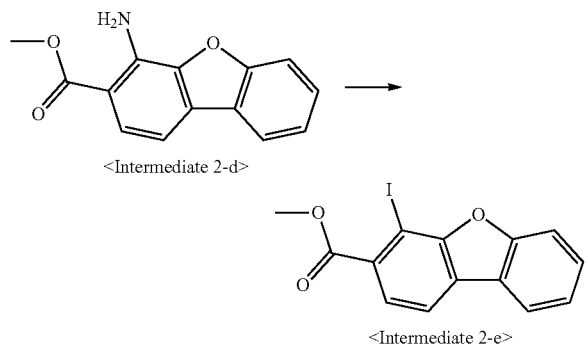

In a 500-mL round-bottom flask reaction, <Intermediate 2-d> (14.0 g, 0.058 mol), HCl (20 ml), and water (100 ml) were stirred together for 1 hr at 0° C. At the same temperature, an aqueous solution (50 ml) of sodium nitrite (7.4 g, 0.116 mol) was dropwise added to the reaction mixture and then stirred for 1 hr. An aqueous solution (100 ml) of potassium iodide (30.0 g, 0.180 mol) was dropwise added with care not to increase the temperature of the reaction solution above 5° C. Stirring was continued for 5 hrs at room temperature, and after completion of the reaction, the reaction mixture was washed with an aqueous sodium thiosulfate solution, and extracted with ethyl acetate and water. The organic layer was separated and concentrated in a vacuum. Purification through column chromatography gave <Intermediate 2-e>. (9.1 g, 48%) Synthesis Example 2-(6): Synthesis of Intermediate 2-f

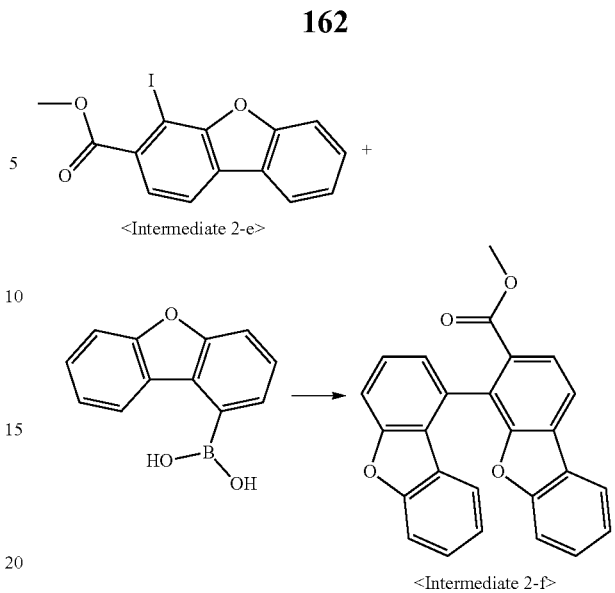

In a 500-mL round-bottom flask reactor, <Intermediate 2-e> (9.3 g, 25 mmol), 1-dibenzofuran boronic acid (8.3 g, 28 mmol), tetrakis(triphenylphosphine)palladium (0.6 g, 0.05 mmol), and potassium carbonate (6.7 g, 50 mmol) were stirred together with toluene (50 mL), tetrahydrofuran (50 mL), and water (20 mL) for 10 hrs at 80° C. After completion of the reaction, the reaction mixture was cooled to room temperature and extracted with ethyl acetate. The organic layer thus formed was separated, concentrated in a vacuum, and purified by column chromatography to afford <Intermediate 2-f> (5.3 g, 52.3%).

Synthesis Example 2-(7): Synthesis of Intermediate 2-g

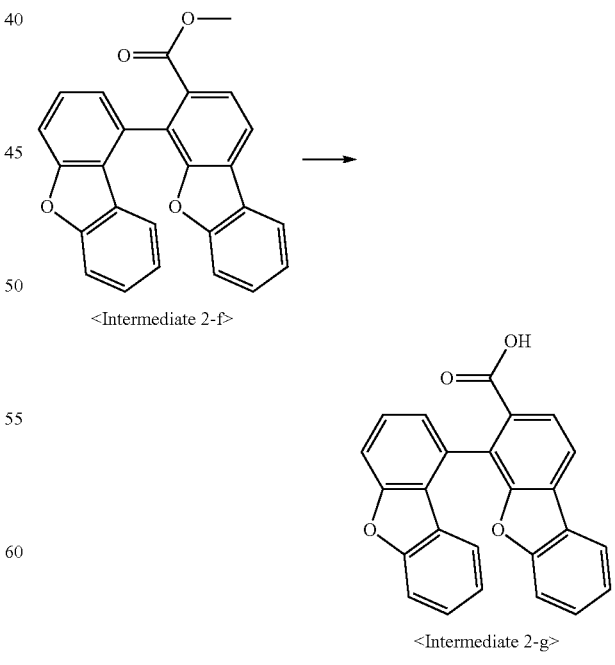

In a 100-mL round-bottom flask reactor, <Intermediate 2-f> (5.3 g, 15 mmol), sodium hydroxide (0.7 g, 17 mmol)

and ethanol (50 ml) were stirred together for 48 hrs under reflux. After the completion of the reaction was confirmed using thin-layer chromatography, the reaction mixture was cooled to room temperature. The chilled solution was acidified with drops of 2-N HCl, followed by stirring for 30 min. The solid thus formed was filtered and then recrystallized in dichloromethane and n-hexane to afford <Intermediate 2-g>. (4.5 g, 88.0%) Synthesis Example 2-(8): Synthesis of Intermediate 2-h

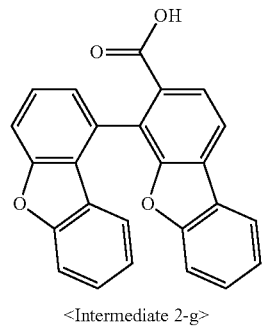

<Intermediate 2-g>

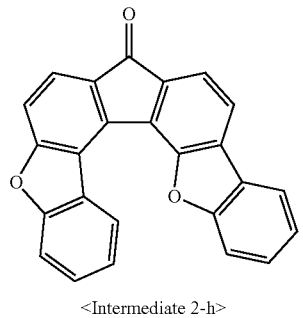

<Intermediate 2-h>

In a 100-mL round-bottom flask reactor, <Intermediate 2-g> (4.5 g, 12 mmol) and methanesulfonic acid (30 ml) were stirred together for 3 hrs at 80° C. After the completion of the reaction was confirmed using thin-layer chromatography, the reaction mixture was cooled to room temperature and dropwise added to ice water (50 ml). After stirring for 30 min, the solid thus formed was filtered and washed with water and methanol to afford <Intermediate 2-h> (3.8 g, 88.8%). Synthesis Example 2-(9): Synthesis of Intermediate 2-i

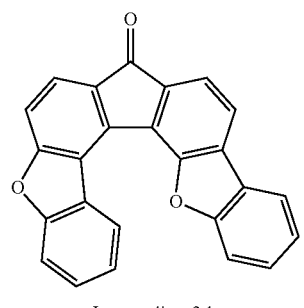

<Intermediate 2-h>

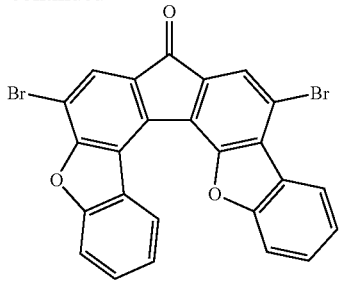

<Intermediate 2-i>

In a 100-mL round-bottom flask reactor, <Intermediate 2-h> (3.8 g, 11 mmol) and dichloromethane (40 ml) were stirred together at room temperature. A dilution of bromine (1.1 ml, 22 mmol) in dichloromethane (10 ml) was dropwise added, followed by stirring at room temperature for 8 hrs. After completion of the reaction, the reaction mixture was stirred together with acetone (20 ml). The solid thus formed was filtered and washed with acetone. Recrystallization in monochlorobenzene afforded <Intermediate 2-i> (3.0 g, 55%).

Synthesis Example 2-(10): Synthesis of Intermediate 2-j

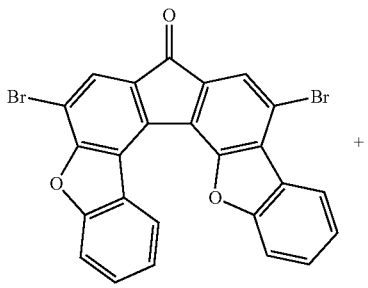

<Intermediate 2-i>

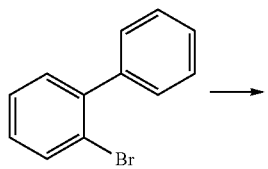

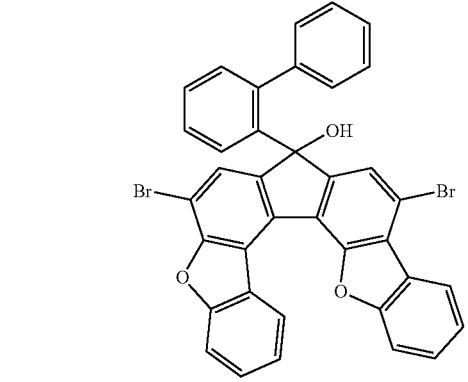

<Intermediate 2-j>

In a 100-ml round-bottom flask reactor, 2-bromobiphenyl (2.1 g, 0.009 mol) and tetrahydrofuran (30 ml) were chilled at −78° C. in a nitrogen atmosphere. At the same temperature, n-butyl lithium (4.8 ml, 0.008 mol) was dropwise added to the reaction solution, which was then stirred for 2 hrs. Thereafter, <Intermediate 2-i> (3.0 g, 0.006 mol) was added little by little to the reaction solution and stirred at room temperature. After the reaction was stopped with $H_2O$ (10 ml), extraction was conducted with ethyl acetate and water. The organic layer was separated, concentrated in a vacuum, and recrystallized in acetonirile to afford <Intermediate 2-j> as a solid (2.5 g, 64%).

Synthesis Example 2-(11): Synthesis of Intermediate 2-k

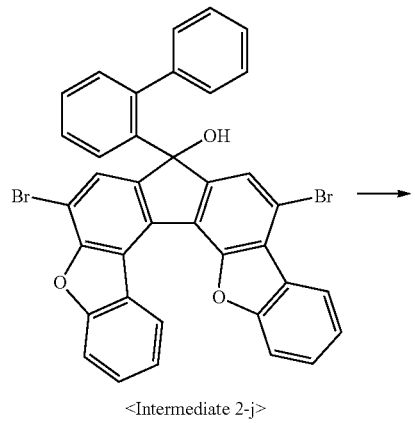

<Intermediate 2-j>

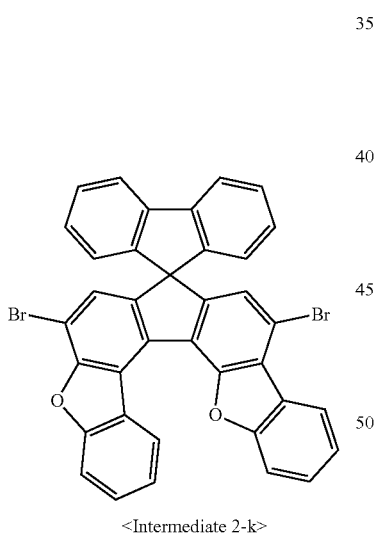

<Intermediate 2-k>

In a 100-ml round-bottom flask reactor, a mixture of <Intermediate 2-j> (2.5 g, 0.04 mol), acetic acid (25 ml), and sulfuric acid (0.5 ml) was stirred for 5 hrs under reflux. When a precipitate was formed, the completion of the reaction was monitored using thin-layer chromatography. The reaction mixture was then cooled to room temperature and filtered. The filtrate was washed with $H_2O$ and methanol and dissolved in monochlorobenzene. Following silica gel chromatography, the fraction was concentrated and cooled to room temperature to give <Intermediate 2-k> (2.2 g, 90%).

Synthesis Example 2-(12): Synthesis of Compound of Chemical Formula 198

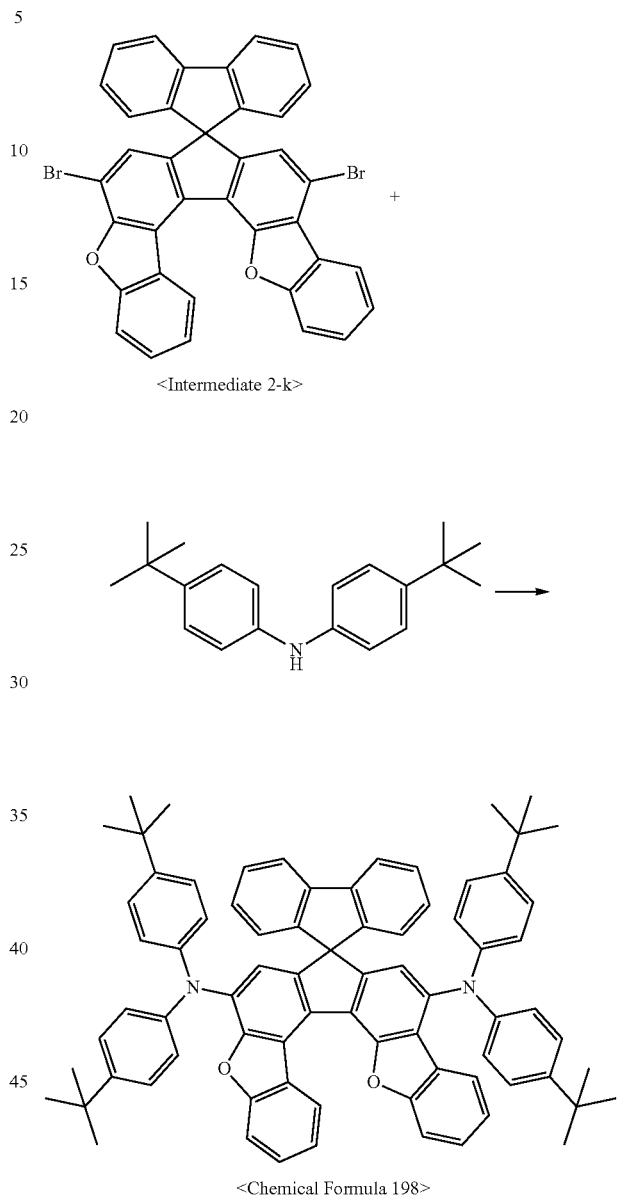

<Chemical Formula 198>

In a 100-ml round-bottom flask reactor, a mixture of <Intermediate 2-k> (2.2 g, 0.003 mol), bis(4-tert-butylphenyl)amine (2.3 g, 0.008 mol), palladium (II) acetate (0.04 g, 0.2 mmol), sodium tert-butoxide (1.6 g, 0.016 mol), tri-tert-butyl phosphine (0.04 g, 0.2 mmol), and toluene (30 ml) was stirred for 2 hrs under reflux. After completion of the reaction, the reaction mixture was cooled to room temperature and then extracted with dichloromethane and water. The organic layer thus formed was separated, dried over magnesium sulfate, and concentrated in a vacuum. The concentrate was purified by column chromatography and recrystallized in dichloromethane and acetone to yield the compound of Chemical Formula 198 as a solid (1.4 g, 43%)).

MS (MALDI-TOF): m/z 1054.54 [Mt]

Synthesis Example 3: Synthesis of Compound of Chemical Formula 331

Synthesis Example 3-(1): Synthesis of Intermediate 3-a

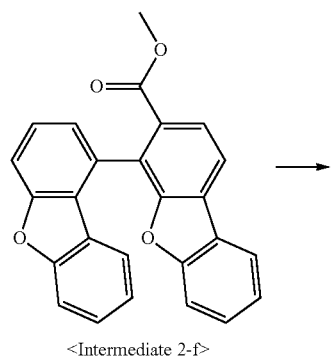

<Intermediate 2-f>

In a 500-ml round-bottom flask reactor, a mixture of bromobenzene (25.5 g, 0.163 mol) and tetrahydrofuran (170 ml) was cooled to −78° C. under a nitrogen atmosphere. At the same temperature, n-butyl lithium (1.6 M) (95.6 ml, 0.153 mol) was dropwise added to the mixture, and stirred for 1 hrs. Then, <Intermediate 2-f> (20.0 g, 0.051 mol) was added and stirred at room temperature for 3 hrs. After completion of the reaction, water (50 ml) was added to the reaction mixture that was then stirred for 30 min. The reaction mixture was extracted with ethyl acetate and water, and the organic layer was separated and concentrated in a vacuum. The concentrate was mixed with acetic acid (200 ml) and HCl (1 ml) and stirred at 80° C. When the reaction was completed, the reaction mixture was cooled to room temperature, and filtered. The filtrate was washed with methanol to afford <Intermediate 3-a> as a solid (20.0 g, 78%).

Synthesis Example 3-(2): Synthesis of Intermediate 3-b

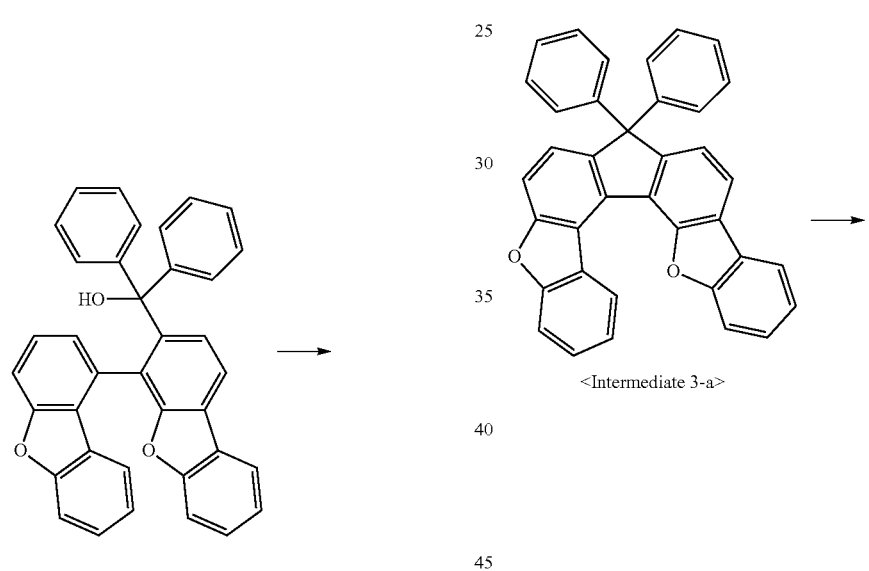

<Intermediate 3-a>

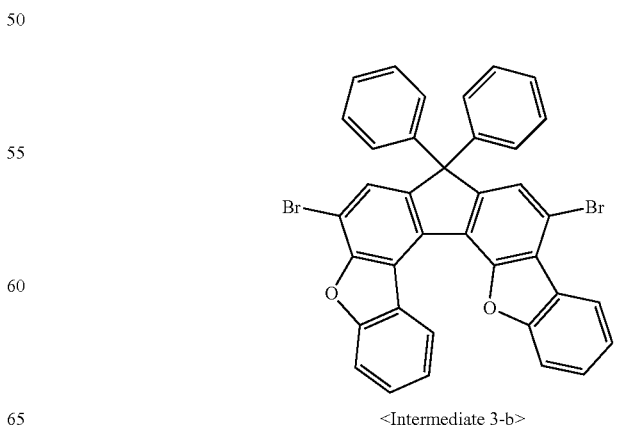

<Intermediate 3-b>

In a 100-mL round-bottom flask reactor, <Intermediate 3-a> (20 g, 58 mmol) was stirred together with dichloromethane (40 ml) at room temperature, and then a dilution of bromine (5.8 ml, 116 mmol) in dichloromethane (10 ml) was dropwise added, followed by stirring at room temperature for 8 hrs. After completion of the reaction, acetone (20 ml) was added to the reactor and stirred. The precipitate thus formed was filtered, and washed with acetone. Recrystallization in monochlorobenzene gave <Intermediate 3-b> as a solid (15.8 g, 55%).

Synthesis Example 3-(3): Synthesis of Compound of Chemical Formula 331

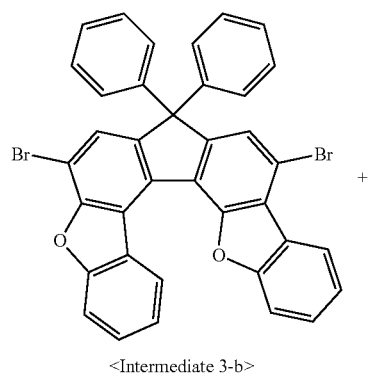

<Intermediate 3-b>

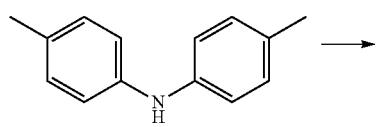

In a 100-ml round-bottom flask reactor, <Intermediate 3-b> (4.0 g, 0.006 mol), di-p-tolyl amine (3.2 g, 0.016 mol), palladium (II) acetate (0.08 g, 0.4 mmol), sodium tert-butoxide (3.2 g, 0.032 mol), and tri-tert-butyl phosphine (0.08 g, 0.4 mmol) were stirred together with 30 ml of toluene for 2 hrs under reflux. After completion of the reaction, the reaction mixture was cooled to room temperature, and extracted with dichloromethane and water. The organic layer thus formed was separated, dried over magnesium sulfate, and concentrated in a vacuum. The concentrate was purified by column chromatography and recrystallized in dichloromethane and acetone to afford the compound of <Chemical Formula 331> (2.1 g, 41%).

MS (MALDI-TOF): m/z 888.37 [Mt]

Evaluation Example of Organic Light-Emitting Diode

Respective Compounds for use as the host, the hole assistant compound, and the dopant according to the present disclosure are well known in the art and explanations of the preparation thereof are thus omitted.

The HOMO energy levels of the host and the hole assistant compound were measured using PYS-202 in a single thin layer of each compound on a quartz substrate.

In addition, the host and the hole assistant compounds were measured for hole mobility, using time of flight (TOF) spectrometry in a 4-μm-thick single layer of each compound on a glass substrate having an ITO electrode formed thereon.

Figure 3:
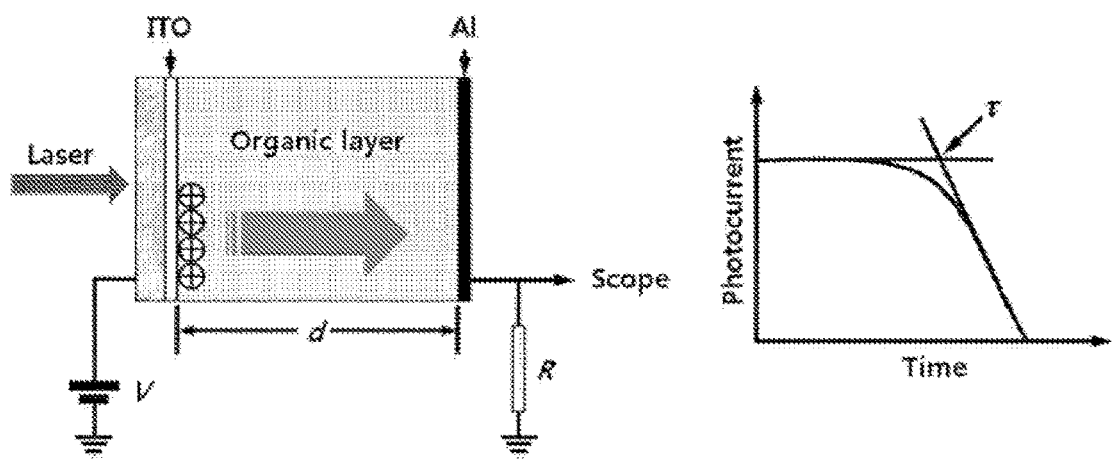
FIG. 3 shows a schematic view of a time-of-flight spectrometer for measuring hole mobility (p) and a view illustrating the measurement of hole mobility according to an embodiment of the present disclosure.

FIG. 3 illustrate a TOF spectrometer, and hole mobility was measured using the following equation. In the equation, d, T, and V refers to a thickness of a film formed of an organic compound, a retention time of carrier, and a voltage applied to a diode, respectively.

$$\mu = \frac{d^2}{\tau \cdot V}$$

Example 1

An ITO glass substrate was patterned to have a luminescent area of 2 mm×2 mm and cleansed. The substrate was mounted in a vacuum chamber, which was then set to have a base pressure of 1×10$^{-7}$ torr. On the ITO glass substrate, films of DNTPD (400 Å), a-NPD (200 Å), a mixture of Chemical Formula 4, Compound 101, and BD (weight ratio 90:7:3) for a light-emitting layer, [Chemical Formula E-1] (300 Å), [Chemical Formula E-2] (5 Å), and Al for a cathode formed in that order to fabricate an organic electroluminescent diode. The organic light-emitting diode was measured at 10 mA/cm² for luminescence properties.

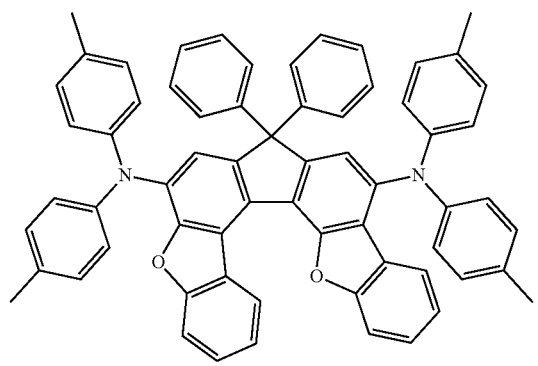

<Chemical Formula 331>

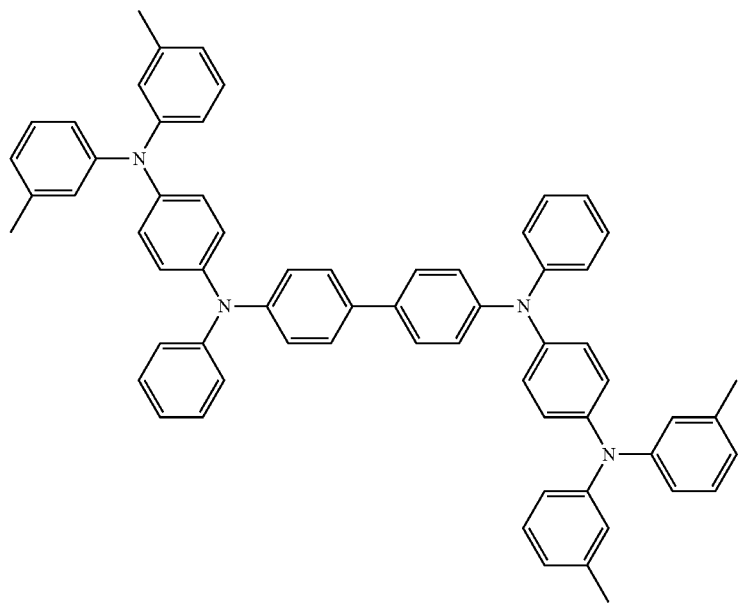
[DNTPD]
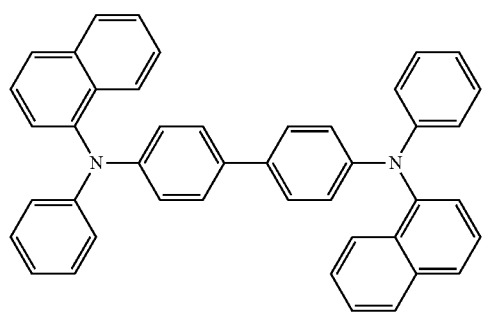
[α-NPD]
[Chemical Formula E-1]
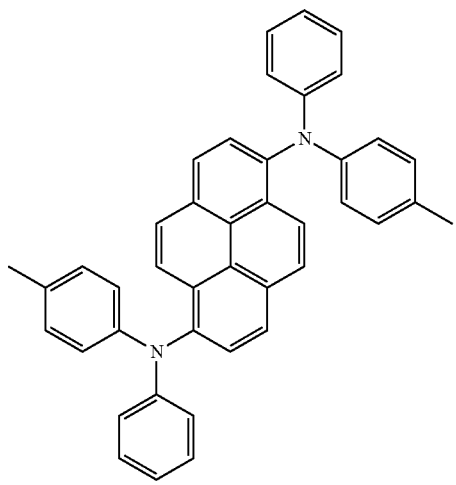
[BD]
[Chemical Formula E-2]
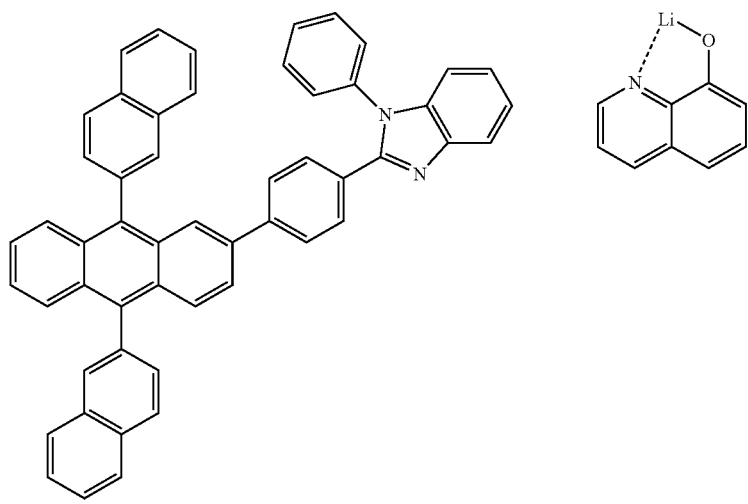

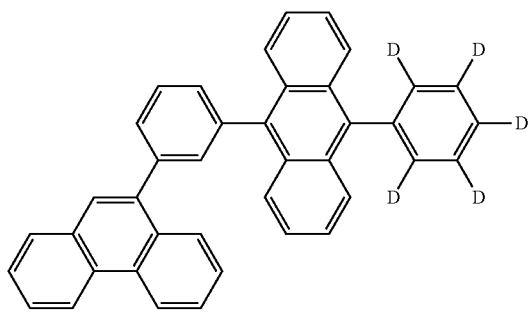
<Chemical Formula 4>
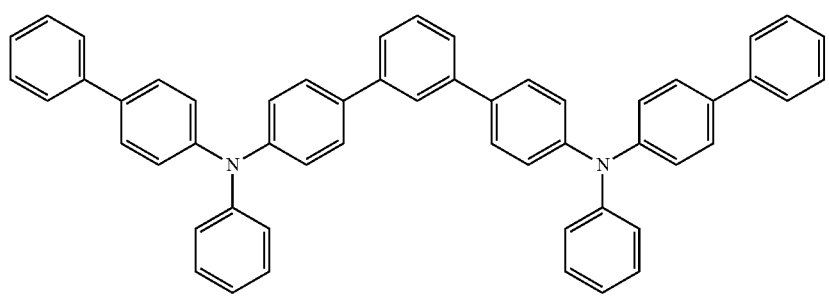
[Compound 101]
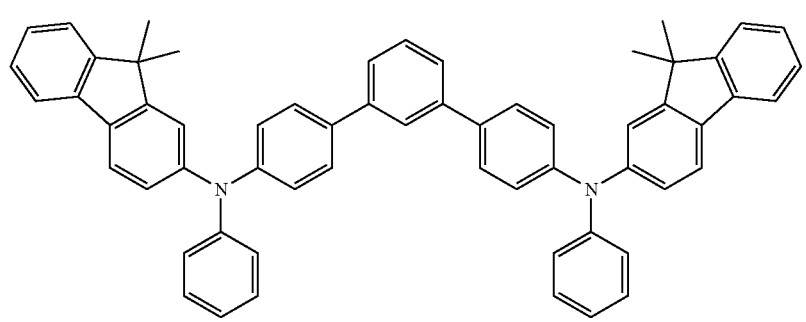
[Compound 122]
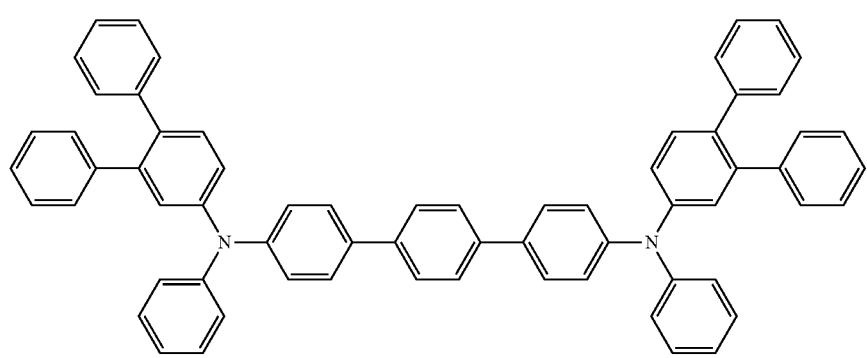
[Compound 138]

-continued

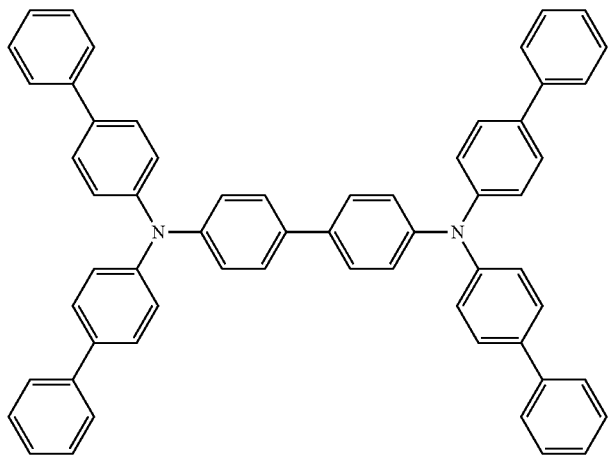

[Compound 142]

Example 2

An organic light-emitting diode was fabricated in the same manner as in Example 1, with the exception of using Compound 122 instead of Compound 101, and measured at 10 mA/cm² for luminescence properties.

Example 3

An organic light-emitting diode was fabricated in the same manner as in Example 1, with the exception of using Compound 138 instead of Compound 101, and measured at 10 mA/cm² for luminescence properties.

Example 4

An organic light-emitting diode was fabricated in the same manner as in Example 1, with the exception of using Compound 142 instead of Compound 101, and measured at 10 mA/cm² for luminescence properties.

Example 5

An organic light-emitting diode was fabricated in the same manner as in Example 1, with the exception of using [Chemical Formula 101] instead of [BD], and measured at 10 mA/cm² for luminescence properties.

Example 6

An organic light-emitting diode was fabricated in the same manner as in Example 1, with the exception of using [Chemical Formula 198] instead of [BD], and measured at 10 mA/cm² for luminescence properties.

Example 7

An organic light-emitting diode was fabricated in the same manner as in Example 1, with the exception of using [Chemical Formula 331] instead of [BD], and measured at 10 mA/cm² for luminescence properties.

Example 8

An organic light-emitting diode was fabricated in the same manner as in Example 4, with the exception of using [Chemical Formula 10] and [Chemical Formula 198] instead of [Chemical Formula 4] and [BD], respectively, and measured at 10 mA/cm² for luminescence properties.

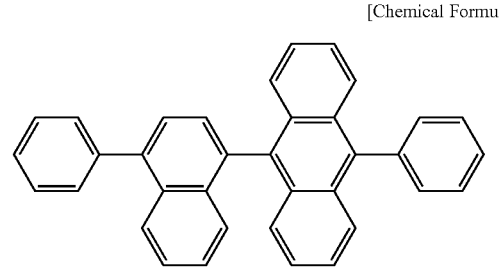

[Chemical Formula 10]

Example 9

An organic light-emitting diode was fabricated in the same manner as in Example 1, with the exception of using [Chemical Formula 10] and [Chemical Formula 331] instead of [Chemical Formula 4] and [BD], respectively, and measured at 10 mA/cm² for luminescence properties.

Example 10

An organic light-emitting diode was fabricated in the same manner as in Example 2, with the exception of using [Chemical Formula 10] and [Chemical Formula 198] instead of [Chemical Formula 4] and [BD], respectively, and measured at 10 mA/cm² for luminescence properties.

Comparative Example 1

An organic light-emitting diode was fabricated in the same manner as in Example 1, with the exception of not doping the light-emitting layer of the organic EL diode with the hole assistant compound, and measured at 10 mA/cm² for luminescence properties.

Comparative Example 2

An organic light-emitting diode was fabricated in the same manner as in Example 10, with the exception of not doping the light-emitting layer of the organic EL diode with the hole assistant compound, and measured at 10 mA/cm² for luminescence properties.

HOMO energy levels and hole mobility of the host and hole assistant compounds are summarized in Table 1, below.

TABLE 1

|  | HOMO Energy Level (eV) | Hole Mobility (cm²/Vs) |
|---|---|---|
| Host (Chemical Formula 4) | −6.05 | $10^{-5}$ |
| Compound 101 | −5.75 | $10^{-3}$ |
| Compound 122 | −5.65 | $10^{-3}$ |
| Compound 138 | −5.67 | $10^{-4}$ |
| Compound 142 | −5.53 | $10^{-3}$ |

The evaluation results in Table 1 indicate that the hole assistant compounds of the present disclosure is smaller in HOMO energy level and greater in hole motility than the host compound.

In addition, properties of the organic light-emitting diodes fabricated in the Examples and the Comparative Examples are given in Table 2, below. In Table 2, the lifespan refers to a time taken for luminance to decrease to 90% of the initial luminance (2000 cd/m²).

TABLE 2

|  | Hole Assistant | Host Cpd. | Dopant Cpd. | Driving Volt. | CIEx | CIEy | Photo-luminescence Peak | Lifespan (hr) |
|---|---|---|---|---|---|---|---|---|
| Ex. 1 | Cpd. 101 | Cpd. 101 | BD | 3.84 | 0.135 | 0.119 | 459 | 270 |
| Ex. 2 | Cpd. 122 | Cpd. 101 | BD | 3.82 | 0.135 | 0.118 | 459 | 300 |
| Ex. 3 | Cpd. 138 | Cpd. 101 | BD | 3.81 | 0.135 | 0.119 | 459 | 390 |
| Ex. 4 | Cpd. 142 | Cpd. 101 | BD | 3.80 | 0.134 | 0.120 | 460 | 345 |
| C. Ex. 1 | — | Cpd. 101 | BD | 3.90 | 0.135 | 0.119 | 460 | 195 |
| Ex. 5 | Cpd. 101 | Chemical Formula 4 | Chemical Formula 101 | — | 0.136 | 0.111 | 458 | 500 |
| Ex. 6 | Cpd. 122 | Chemical Formula 4 | Chemical Formula 198 | — | 0.135 | 0.110 | 457 | 520 |
| Ex. 7 | Cpd. 138 | Chemical Formula 4 | Chemical Formula 331 | — | 0.135 | 0.109 | 456 | 510 |
| Ex. 8 | Cpd. 142 | Chemical Formula 10 | Chemical Formula 198 | — | 0.135 | 0.109 | 457 | 570 |
| Ex. 9 | Cpd. 101 | Chemical Formula 10 | Chemical Formula 331 | — | 0.135 | 0.109 | 457 | 535 |
| Ex. 10 | Cpd. 122 | Chemical Formula 10 | Chemical Formula 198 | — | 0.135 | 0.108 | 457 | 550 |
| C. Ex. 2 | — | Chemical Formula 10 | Chemical Formula 198 | — | 0.136 | 0.110 | 457 | 290 |

As is understood from the evaluation data of Table 2, the organic light-emitting diode of the present invention which employs the compound represented by Chemical Formula A as a hole assistant was found to have a longer lifespan and a somewhat lower driving voltage than that fabricated according to the Comparative Examples.

INDUSTRIAL APPLICABILITY

Designed to facilitate the hole mobility of a host compound, the organic light-emitting diode according to the present disclosure exhibits more improved device properties including a long lifespan and a low driving voltage and thus is industrially applicable.

The invention claimed is:

1. An organic light-emitting diode: comprising a first electrode; a second electrode facing the first electrode; and a hole transport layer and a light-emitting layer disposed in that order between the first and the second electrode, wherein the light-emitting layer includes a hole assistant material represented by the following Chemical Formula A, an anthracene-based host represented by the following Chemical Formula H, and an amine compound represented by the following Chemical Formula B or C as a dopant, wherein the hole assistant material having a highest occupied molecular orbital (HOMO) energy level lower in absolute value than a highest occupied molecular orbital (HOMO) energy level of the anthracene-based host

[Chemical Formula A]

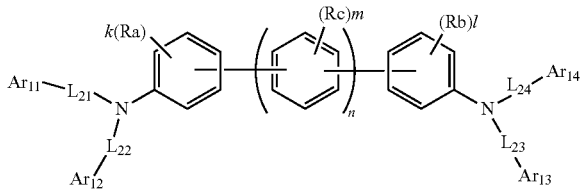

wherein,
substituents $Ar_{11}$ to $Ar_{14}$ may be the same or different and are each independently a substituted or unsubstituted aryl of 6 to 50 carbon atoms, or a substituted or unsubstituted heteroaryl of 2 to 50 carbon atoms, linkers $L_{21}$ to $L_{24}$ may be the same or different and are each independently a single bond or a substituted or unsubstituted arylene of 6 to 50 carbon atoms, Ra, Rb, and Rc may be the same or different and are each independently one selected from among a hydrogen atom, a deuterium atom, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted aryl of 6 to 50 carbon atoms, a substituted or unsubstituted heteroaryl of 2 to 50 carbon atoms bearing O, N, or S as a heteroatom, a cyano, a nitro, a halogen, and a substituted or unsubstituted silyl of 1 to 30 carbon atoms, k, l, and m may be the same or different and are each an integer of 1 to 4, with the proviso that when k, l, and m are each an integer of 2 or greater, the corresponding plural Ra's Rb's, or Rc's may be the same or different, n is 0; and

[Chemical Formula H]

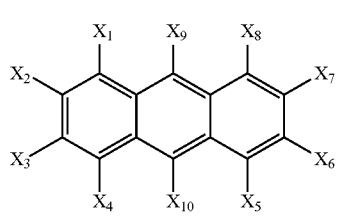

wherein, $X_1$ to $X_{10}$ may be the same or different and are each independently one selected from the group consisting of a hydrogen atom, a deuterium atom, a substituted or unsubstituted alkyl of 1 to 30 carbon atoms, a substituted or unsubstituted alkenyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted aryl of 6 to 50 carbon atoms, a substituted or unsubstituted heteroaryl of 2 to 50 carbon atoms bearing O, N, or S as a heteroatom, a substituted or unsubstituted silicon, a substituted or unsubstituted boron, a substituted or unsubstituted silane, a carbonyl, a phosphoryl, an amino, a nitrile, a hydroxyl, a nitro, a halogen, an amide, and an ester, with the proviso that adjacent radicals may form an aliphatic, aromatic, heteroaliphatic, or heteroaromatic fused ring, wherein the term "substituted" in the expression "substituted or unsubstituted" used for Chemical Formulas A and H means having at least one substituent selected from the group consisting of a deuterium atom, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a heteroarylamino of 1 to 24 carbon atoms, an alkylsilyl of 1 to 24 carbon atoms, an arylsilyl of 6 to 24 carbon atoms, and an aryloxy of 6 to 24 carbon atoms, wherein the light-emitting layer includes a dopant, which is an amine compound represented by the following Chemical Formula B or C,

[Chemical Formula B]

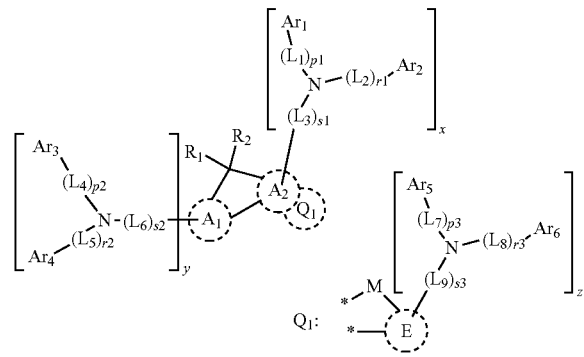

[Chemical Formula C]

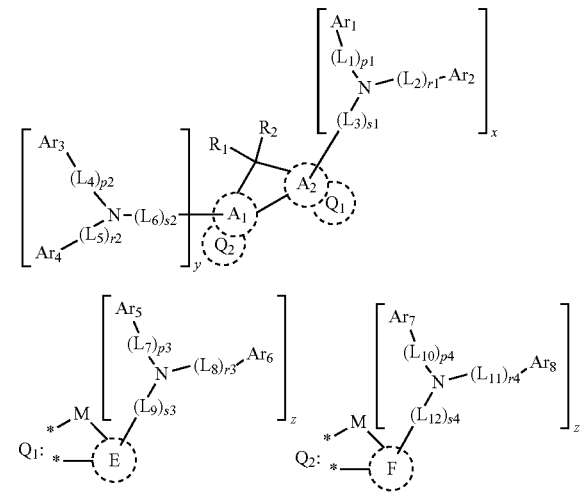

wherein, $A_1, A_2, E,$ and F may be the same or different and are each independently a substituted or unsubstituted aromatic hydrocarbon ring of 6 to 50 carbon atoms or a substituted or unsubstituted heteroaromatic ring of 2 to 40 carbon atoms wherein two adjacent carbon atoms of the ring $A_1$ and two adjacent carbon atoms of the ring $A_2$ form a 5-membered fused ring with a carbon atom connected to both substituents $R_1$ and $R_2$;

linkers $L_1$ to $L_{12}$ may be the same or different, and are each independently selected from among a direct bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

M is any one selected from among N-$R_3$, $CR_4R_5$, $SiR_6R_7$, $GeR_8R_9$, O, S, and Se;

$R_1$ to $R_9$, and $Ar_1$ to $Ar_8$ may be the same or different, and are each independently any one selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a substituted or unsubstituted alkylgermanium of 1 to 30 carbon atoms, a substituted or unsubstituted arylgermanium of 6 to 30 carbon atoms, a cyano, a nitro, and a halogen, with the proviso that $R_1$ and $R_2$ may be bonded to each other to form a mono- or polycyclic aliphatic or aromatic ring, which may be a heterocyclic ring containing a heteroatom selected from among N, O, P, Si, S, Ge, Se, and Te as a ring member;

p1 to p4, $r_1$ to $r_4$, and s1 to s4 are each independently an integer of 1 to 3, with the proviso that when any of them is 2 or greater, the corresponding linkers L1's and L12's may be individually the same or different, x is an integer of 1 or 2, and y and z may be the same or different and are each independently an integer of 0 to 3; and a ring may be formed between $Ar_1$ and $Ar_2$, between $Ar_3$ and $Ar_4$, between $Ar_5$ and $Ar_6$, and between $Ar_7$ and $Ar_8$, two adjacent carbon atoms of the $A_2$ ring of Chemical Formula B may occupy respective positions * of Structural Formula $Q_1$ to form a fused ring, and two adjacent carbon atoms of the $A_1$ ring of Chemical Formula C may occupy respective positions * of structural Formula $Q_2$ to form a fused ring, and two adjacent carbon atoms of the $A_2$ ring of Chemical Formula C may occupy respective positions * of Structural Formula $Q_1$ to form a fused ring, wherein the term 'substituted' in the expression 'substituted or unsubstituted' used in Chemical Formulas B and C means having at least one substituent selected from the group consisting of a deuterium atom, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 6 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a heteroarylamino of 1 to 24 carbon atoms, an alkylsilyl of 1 to 24 carbon atoms, an arylsilyl of 6 to 24 carbon atoms, and an aryloxy of 6 to 24 carbon atoms.

2. The organic light-emitting diode of claim 1, wherein Ra, Rb, and Rc may be the same or different and are each independently selected among a hydrogen atom, a deuterium atom, a substituted or unsubstituted alkyl of 1 to 10 carbon atoms, and a substituted or unsubstituted aryl of 6 to 20 carbon atoms, and linkers $L_{21}$ to $L_{24}$ may be the same or different and are each independently selected from among a single bond and a substituted or unsubstituted aryl of 6 to 20 carbon atoms.

3. The organic light-emitting diode of claim 1, wherein the hole assistant material is used in an amount of 1 to 30 weight parts, based on 100 weight parts of the anthracene-based host.

4. The organic light-emitting diode of claim 1, wherein a hole mobility of the hole assistant material is larger than a hole mobility of the anthracene-based host.

5. The organic light-emitting diode of claim 1, wherein wt % of the hole assistant material in the light-emitting layer ranges from 0.5 to 4 times wt % of the dopant.

6. The organic light-emitting diode of claim 1, wherein the substituents $Ar_{11}$ to $Ar_{14}$ may be the same or different and are each independently a substituted or unsubstituted aryl of 6 to 50 carbon atoms in Chemical Formula A.

7. The organic light-emitting diode of claim 1, wherein the hole assistant material is one selected from the group consisting of [Compound 140] to [Compound 142]:

<Compound 140>

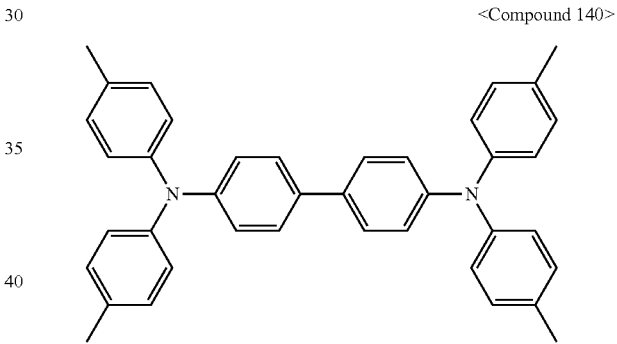

<Compound 141>

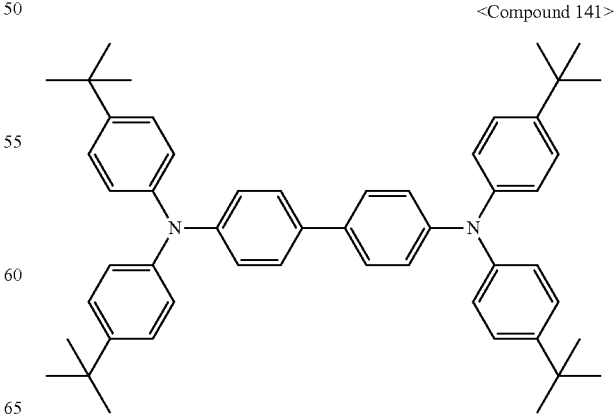

-continued

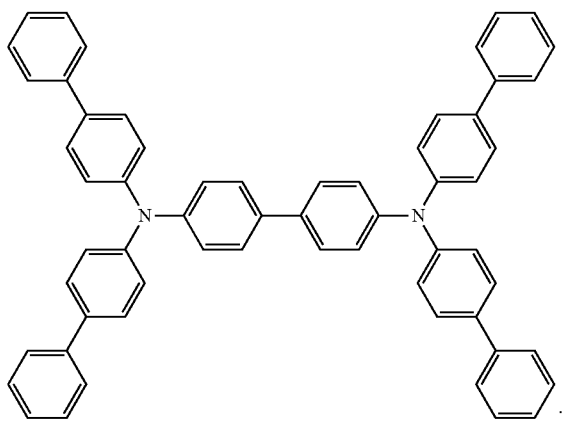

<Compound 142>

8. The organic light-emitting diode of claim 1, wherein $A_1$, $A_2$, E, and F ring moieties in Chemical Formula B or C may be the same or different and are each independently substituted or unsubstituted aromatic hydrocarbon rings of 6 to 50 carbon atoms.

9. The organic light-emitting diode of claim 1, wherein in which y is 1 and z is zero in Chemical Formula B or C.

10. The organic light-emitting diode of claim 1, wherein the first electrode is an anode, the second electrode is a cathode, a hole injection layer is disposed in the anode and the hole transport layer, and an electron transport layer and an electron injection layer are sequentially arranged between the light-emitting layer and the cathode.

11. The organic light-emitting diode of claim 1, wherein the light-emitting layer emits light with a central wavelength ranging from 350 nm to 550 nm.

12. The organic light-emitting diode of claim 10, wherein at least one selected from among the hole injection layer, the hole transport layer, the electron transport layer, the electron injection layer, and the light-emitting layer is deposited using a deposition process or a solution process.

13. The organic light-emitting diode of claim 1, wherein the organic light-emitting diode is used for a device selected from among a flat display device; a flexible display device; a monochrome or grayscale flat illumination device; and a monochrome or grayscale flexible illumination device.

* * * * *